US012667585B2

(12) United States Patent
Zhao et al.

(10) Patent No.: US 12,667,585 B2
(45) Date of Patent: Jun. 30, 2026

(54) IMMUNOTHERAPEUTIC NANOPARTICLES AND METHODS RELATING THERETO

(71) Applicant: Wake Forest University Health Sciences, Winston-Salem, NC (US)

(72) Inventors: Dawen Zhao, Winston-Salem, NC (US); Yang Liu, Winston-Salem, NC (US); Neil William Crowe, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 779 days.

(21) Appl. No.: 17/601,178

(22) PCT Filed: Apr. 8, 2020

(86) PCT No.: PCT/US2020/027213
§ 371 (c)(1),
(2) Date: Oct. 4, 2021

(87) PCT Pub. No.: WO2020/210317
PCT Pub. Date: Oct. 15, 2020

(65) Prior Publication Data
US 2022/0193108 A1 Jun. 23, 2022

Related U.S. Application Data

(60) Provisional application No. 62/832,106, filed on Apr. 10, 2019.

(51) Int. Cl.
A61K 31/7084 (2006.01)
A61K 9/00 (2006.01)
(Continued)

(52) U.S. Cl.
CPC ........ A61K 31/7084 (2013.01); A61K 9/0073 (2013.01); A61K 9/127 (2013.01); A61K 39/3955 (2013.01)

(58) Field of Classification Search
CPC .. A61K 31/7084; A61K 9/0073; A61K 9/127; A61K 39/3955; A61K 9/0078; A61P 35/00
See application file for complete search history.

(56) References Cited

U.S. PATENT DOCUMENTS 6,962,151 B1 11/2005 Knoch et al.
7,592,326 B2 9/2009 Karaolis
(Continued)

FOREIGN PATENT DOCUMENTS

WO 2017165506 A1 9/2017
WO 2018053508 A1 3/2018
(Continued)

OTHER PUBLICATIONS

Tang et al, "Preparation of optimized lipid-coated calcium phosphate nanoparticles for enhanced in vitro gene delivery to breast cancer cells", J. Mater. Chem. B, 2015, 3, 6805-6812. (Year: 2015).*

(Continued)

*Primary Examiner* — Sahana S Kaup
*Assistant Examiner* — Joshua A Atkinson
(74) *Attorney, Agent, or Firm* — Kilpatrick Townsend & Stockton LLP

(57) ABSTRACT

Compositions containing lipid nanoparticles and nucleic acid therapeutic agents are disclosed. For example, calcium phosphate nanoparticles having a lipid coating are provided, wherein the calcium phosphate nanoparticles include a cyclic dinucleotide and the lipid coating includes phosphatidylserine. The compositions can be formulated for administration to the lungs of a subject via inhalation, or for administration via injection. Methods for the treatment of lung cancer and other cancers are also described. Targeted delivery of therapeutic agents such as cyclic dinucleotides to (Continued)

antigen presenting immune cells via the disclosed methods can elicit beneficial antitumor immunity.

15 Claims, 33 Drawing Sheets

(51) Int. Cl.
　　*A61K 9/127*　　　　(2025.01)
　　*A61K 39/395*　　　(2006.01)

(56) References Cited

U.S. PATENT DOCUMENTS

| | | | |
|---|---|---|---|
| 7,624,968 | B2 | 12/2009 | Lu |
| 7,709,458 | B2 | 5/2010 | Karaolis et al. |
| 8,367,716 | B2 | 2/2013 | Karaolis |
| 9,724,408 | B2 | 8/2017 | Dubensky, Jr. et al. |
| 9,757,528 | B2 | 9/2017 | Rubin |
| 10,029,055 | B2 | 7/2018 | Naoum |
| 2010/0092425 | A1 | 4/2010 | von Andrian et al. |
| 2016/0333355 | A1* | 11/2016 | Deng ................. A61K 41/0038 |

FOREIGN PATENT DOCUMENTS

| | | | |
|---|---|---|---|
| WO | 2018118665 | A1 | 6/2018 |
| WO | 2018172206 | A1 | 9/2018 |
| WO | 2018198076 | A1 | 11/2018 |

OTHER PUBLICATIONS

Shah et al, "Enhancement of macrophage uptake via phosphatidylserine-coated acelated dextran nanoparticles", J. Drug Del. Sci. Tech., Jan. 2019, 50, 57-65. (Year: 2019).*

Wu et al, "Phosphatidylserine-Containing Liposomes Inhibit the Differentiation of Osteoclasts and Trabecular Bone Loss", J. Immunol., 2010, 184 (6), 3191-3201. (Year: 2010).*

Drechsler et al, "Preparation of Asymmetric Liposomes Using a Phosphatidylserine Decarboxylase", Biophys. J., 2018, 115, 1509-1517. (Year: 2018).*

Koshy et al, "Liposomal Delivery Enhances Immune Activation by STING Agonists for Cancer Immunotherapy", Adv. Biosys. 2017, 1, 1600013, pp. 1-12. (Year: 2017).*

Avanti, "16:0-18:1 PS (POPS)", retrieved 2024 from: https://avantilipids.com/product/840034 (Year: 2024).*

Lee et al, "Inhalation of nanoparticle-based drug for lung cancer treatment: Advantages and challenges", Asian Jour Pharm Sci, 2015, 10, 6, pp. 481-489 (Year: 2015).*

Conner et al, "Cell morphology best predicts tumorigenicity and metastasis in vivo across multiple TNBC cell lines of different metastatic potential", Breast Cancer Res., 2024, 26:43, pp. 1-16 (Year: 2024).*

Shevtsov et al, "Novel Approaches to Improve the Efficacy of Immuno-Radiotherapy", Frontiers in Oncology, 2019, vol. 9, article 156, pp. 1-16 (Year: 2019).*

Ramana et al, "Development of a liposomal nanodelivery system for nevirapine", J. Biomed. Sci., 2010, 17:57, pp. 1-9 (Year: 2010).*

Wodlej et al, "Interaction of two antitumor peptides with membrane lipids—Influence of phosphatidylserine and cholesterol on specificity for melanoma cells", PloS ONE, 2019, 14(1), pp. 1-37 (Year: 2019).*

Gu et al, "Devising new lipid-coated calcium phosphate/carbonate hybrid nanoparticles for controlled release in endosomes for efficient gene delivery", J. Mater. Chem. B, 2017, 5, 7194-7203 (Year: 2017).*

PCT Application No. PCT/US2020/027213, International Search Report and Written Opinion, mailed on Aug. 31, 2020, 13 pages.

"Liposome Drug Products: Chemistry, Manufacturing, and Controls; Human Pharmacokinetics and Bioavailability; and Labeling Documentation, Guidance for Industry", Food and Drug Administration, Center for Drug Evaluation and Research (CDER), Apr. 2018, 18 pages.

Allen et al., "Liposomal Drug Delivery Systems: From Concept to Clinical Applications", Advanced Drug Delivery Reviews, vol. 65, No. 1, Jan. 2013, pp. 36-48.

Allen Jr., "The Art, Science, and Technology of Pharmaceutical Compounding, Third Edition", American Journal of Pharmaceutical Education, vol. 73, No. 3, Article 39, May 27, 2009, 3 pages.

Au et al., "Folate-Targeted pH-Responsive Calcium Zoledronate Nanoscale Metal-Organic Frameworks: Turning a Bone Antiresorptive Agent Into an Anticancer Therapeutic", Biomaterials, vol. 82, Mar. 2016, pp. 178-193.

Baird et al., "Radiotherapy Combined with Novel STING-Targeting Oligonucleotides Results in Regression of Established Tumors", Cancer Research, vol. 76, No. 1, Jan. 1, 2016, pp. 50-61.

Barber, "STING: Infection, Inflammation and Cancer", Nature Reviews Immunology, vol. 15, No. 12, Dec. 2015, pp. 760-770.

Brody et al., "In Situ Vaccination with a TLR9 Agonist Induces Systemic Lymphoma Regression: a Phase I/II Study", Journal of Clinical Oncology, vol. 28, No. 28, Oct. 1, 2010, pp. 4324-4332.

Cannon, "Goodman and Gilman's The Pharmacological Basis of Therapeutics. 11th Edition Edited by Laurence Brunton, John Lazo, and Keith Parker. McGraw Hill, New York. 2005. xxiii + 2021 pp. 21 x 26 cm. ISBN 0-07-142280-3. $149.95.", Journal of Medicinal Chemistry, vol. 49, No. 3, Jan. 11, 2006.

Cheng et al., "A Nanoparticle-Incorporated STING Activator Enhances Antitumor Immunity in PD-L1-Insensitive Models of Triple-Negative Breast Cancer", JCI Insight, vol. 3, No. 22, Nov. 15, 2018, pp. 1-20.

Chiba et al., "Tumor-Infiltrating DCs Suppress Nucleic Acid-Mediated Innate Immune Responses through Interactions between the Receptor TIM-3 and the Alarmin HMGB1", Nature Immunology, vol. 13, No. 9, Sep. 2012, pp. 832-842.

Demaria et al., "Radiotherapy: Changing the Game in Immunotherapy", Trends in Cancer, vol. 2, No. 6, Jun. 2016, pp. 286-294.

Deng et al., "STING-Dependent Cytosolic DNA Sensing Promotes Radiation-Induced Type I Interferon-Dependent Antitumor Immunity in Immunogenic Tumors", Immunity, vol. 41, No. 5, Nov. 20, 2014, pp. 843-852.

Dewan et al., "Fractionated but not Single-Dose Radiotherapy Induces an Immune-Mediated Abscopal Effect when Combined with Anti-CTLA-4 Antibody", Clinical Cancer Research, vol. 15, No. 17, Sep. 1, 2009, pp. 5379-5388.

Diamond et al., "Type I Interferon is Selectively Required by Dendritic Cells for Immune Rejection of Tumors", Journal of Experimental Medicine, vol. 208, No. 10, Sep. 26, 2011, pp. 1989-2003.

Dovedi et al., "Antitumor Efficacy of Radiation plus Immunotherapy Depends upon Dendritic Cell Activation of Effector CD8+ T Cells", Cancer Immunology Research, vol. 4, No. 7, Jul. 2016, pp. 621-630.

Du et al., "Regulating the Surface Poly(Ethylene Glycol) Density of Polymeric Nanoparticles and Evaluating Its Role in Drug Delivery in Vivo", Biomaterials, vol. 69, Nov. 2015, pp. 1-11.

Engblom et al., "The Role of Myeloid Cells in Cancer Therapies", Nature Reviews Cancer, vol. 16, No. 7, Jun. 24, 2016, pp. 447-462.

Esposti et al., "Calcium Phosphate-Based Nanosystems for Advanced Targeted Nanomedicine", Drug Development and Industrial Pharmacy, vol. 44, No. 8, Mar. 9, 2018, pp. 1223-1238.

Fuertes et al., "Host type I IFN Signals are Required for Antitumor CD8+ T Cell Responses through CD8{alpha}+ Dendritic Cells", Journal of Experimental Medicine, vol. 208, No. 10, Sep. 26, 2011, pp. 2005-2016.

Huang et al., "Characterization of Calcium Phosphate Nanoparticles Based on a PEGylated Chelator for Gene Delivery", ACS Applied Materials & Interfaces, vol. 9, No. 12, Mar. 7, 2017, pp. 10435-10445.

Huang, "Lipid-Coated Calcium Phosphate Nanoparticle and Beyond: A Versatile Platform for Drug Delivery", Journal of Drug Targeting, vol. 26, No. 5-6, Jun.-Jul. 2018, pp. 398-406.

Irvine et al., "Synthetic Nanoparticles for Vaccines and Immunotherapy", Chemical reviews, vol. 115, No. 19, Oct. 14, 2015, pp. 11109-11146.

(56)                    References Cited

OTHER PUBLICATIONS

Janco et al., "Tumor-Infiltrating Dendritic Cells in Cancer Pathogenesis", The Journal of Immunology, vol. 194, No. 7, Apr. 1, 2015, pp. 2985-2991.

Kachikwu et al., "Radiation Enhances Regulatory T Cell Representation", International Journal of Radiation Oncology, Biology, Physics, vol. 81,No. 4, Nov. 15, 2011, pp. 1128-1135.

Keating et al., "Cytosolic DNA Sensors Regulating Type I Interferon Induction", Trends in Immunology: Cell Press, vol. 32, No. 12, Dec. 1, 2011, pp. 574-581.

Knight et al., "Anticancer Effect of 9-nitrocamptothecin Liposome Aerosol on Human Cancer Xenografts in Nude Mice", Cancer Chemotherapy and Pharmacology, vol. 44, Jul. 1999, pp. 177-186.

Kraft et al., "Emerging Research and Clinical Development Trends of Liposome and Lipid Nanoparticle Drug Delivery Systems", Journal of Pharmaceutical Sciences, 103, No. 1, Jan. 2014, pp. 29-52.

Li et al., "Calcium Phosphate Nanoparticles with an Asymmetric Lipid Bilayer Coating for siRNA Delivery to the Tumor", Journal of Controlled Release, vol. 158, No. 1, Feb. 28, 2012, pp. 108-114.

Mangal et al., "Pulmonary Delivery of Nanoparticle Chemotherapy for the Treatment of Lung Cancers: Challenges and Opportunities", Acta Pharmacologica Sinic, 38, No. 6, Jun. 2017, pp. 782-797.

Mason et al., "Targeting Toll-like Receptor 9 with CpG Oligodeoxynucleotides Enhances Tumor Response to Fractionated Radiotherapy", Clinical Cancer Research, vol. 11, No. 1, Jan. 1, 2005, pp. 361-369.

Norian et al., "Tumor-Infiltrating Regulatory Dendritic Cells Inhibit CD8+ T Cell Function via I-Arginine Metabolism", Cancer Research, vol. 69, No. 7, Apr. 1, 2009, pp. 3086-3094.

Pardoll, "The Blockade of Immune Checkpoints in Cancer Immunotherapy", Nature Reviews Cancer, vol. 12, No. 4, Mar. 22, 2012, pp. 252-264.

Park et al., "Extended Release of Perioperative Immunotherapy Prevents Tumor Recurrence and Eliminates Metastases", Science Translational Medicine, vol. 10, No. 433, Mar. 21, 2018.

Perret et al., "Adjuvants that Improve the Ratio of Antigen-Specific Effector to Regulatory T Cells Enhance Tumor Immunity", Cancer Research, Microenvironment and Immunology, vol. 73, No. 22, Nov. 15, 2013, pp. 6597-6608.

Reits et al., "Radiation Modulates the Peptide Repertoire, Enhances MHC Class I Expression, and Induces Successful Antitumor Immunotherapy", Journal of Experimental Medicine, vol. 203, No. 5, May 15, 2006, pp. 1259-1271.

Sagiv-Barfi et al., "Eradication of Spontaneous Malignancy by Local Immunotherapy", Science Translational Medicine, vol. 10, No. 426, Jan. 31, 2018, 26 pages.

Sharabi et al., "Stereotactic Radiation Therapy Augments Antigen-Specific PD-1-Mediated Antitumor Immune Responses via Cross-Presentation of Tumor Antigen", Cancer Immunology Research, vol. 3, No. 4, Apr. 2015, pp. 345-355.

Spranger et al., "Tumor-Residing Batf3 Dendritic Cells Are Required for Effector T Cell Trafficking and Adoptive T Cell Therapy", Cancer Cell, vol. 31, No. 15, May 8, 2017, pp. 711-723.

Srivastava et al., "Type I Interferons Directly Inhibit Regulatory T Cells to Allow Optimal Antiviral T Cell Responses during Acute LCMV Infection", The Journal of Experimental Medicine, vol. 211, No. 5, May 5, 2014, pp. 961-974.

Thoryk et al., "Co-Administration of Lipid Nanoparticles and Sub-Unit Vaccine Antigens Is Required for Increase in Antigen-Specific Immune Responses in Mice", Vaccines (Basel), vol. 4, No. 4, Article 47, Dec. 2016, 14 pages.

Torchilin, "Recent Advances with Liposomes as Pharmaceutical Carriers", Nature Reviews Drug Discovery, vol. 4, No. 2, Feb. 2005, pp. 145-160.

Woo et al., "STING-Dependent Cytosolic DNA Sensing Mediates Innate Immune Recognition of Immunogenic Tumor", Immunity, vol. 41, No. 5, Nov. 20, 2014, pp. 830-842.

Wu et al., "Modulating both Tumor Cell Death and Innate Immunity is Essential for Improving Radiation Therapy Effectiveness", Frontiers in Immunology , vol. 8, No. 613, May 26, 2017, 16 pages.

Zhang et al., "Cyclic GMP-AMP Containing Mixed Phosphodiester Linkages is an Endogenous High-Affinity Ligand for STING", Molecular Cell, vol. 51, Jul. 25, 2013, pp. 226-235.

Zhang et al., "Phosphatidylserine-targeted Bimodal Liposomal Nanoparticles for in Vivo Imaging of Breast Cancer in Mice", Journal of Controlled Release, vol. 183, Jun. 10, 2014, pp. 114-123.

* cited by examiner

CD8-PerCP/Cy5.5

CD4-PE

Foxp3-Alexa Fluor647

Intratracheal model 24 h                    48 h

CD11c+ APC                    NP-cGAMP

LLC-Luc (Tumor)              Merge

IMMUNOTHERAPEUTIC NANOPARTICLES AND METHODS RELATING THERETO

CROSS-REFERENCES TO RELATED APPLICATIONS

The present application is a 371 U.S. national phase application of PCT Application No. PCT/US2020/027213, filed on Apr. 8, 2020, which claims priority to U.S. Provisional Pat. Appl. No. 62/832,106, filed on Apr. 10, 2019, both of which are incorporated herein by reference in their entirety.

BACKGROUND OF THE INVENTION

Immunotherapy is providing tremendous promise in the new era of cancer treatment. Checkpoint inhibitors and adoptive T cell transfer therapy, for example, have shown improved patient survival in melanoma, non-small cell lung cancer, and renal cell cancer patients. However, only a fraction of patients benefit from immunotherapy, and lack of specific tumor targeting is frequently associated with immune-related systemic toxicity. Thus, many attempts are being made to improve anti-cancer immunity while reducing unwanted side effects. In contrast to systemic immunotherapy, intratumoral injection of immunomodulators is intended to focus the immune response locally on the malignancy and the affected draining lymph nodes. Moreover, given the heterogeneous nature of tumor antigens, the intratumoral immunotherapy may have a potential for arousing a polyclonal antitumor immune response in situ against diverse cancer targets.

Among various types of immunomodulators, intratumoral administration of Toll-like receptor (TLR9) ligand CpG oligonucleotides (ODN) has been extensively investigated and promising results have shown its potent immunostimulatory activity in preclinical mouse models and clinical trials (see, Brody, et al. *J Clin Oncol* 28, 4324-4332, (2010); Mason, et al. *Clin Cancer Res* 11, 361-369, (2005); Sagiv-Barfi, et al. *Sci Transl Med* 10, (2018)). Recently, much attention has also focused on activation of the stimulator of interferon genes (STING) pathway to elicit antitumor immunity (Barber, *Nat Rev Immunol* 15, 760-770, (2015)). Being identified as a potent STING agonist, cGMP-AMP (cGAMP) functions in cytosol to ligate STING on endoplasmic reticulum (ER) membrane to activate the STING pathway and type I IFN production. Recent preclinical studies involving intratumoral injection of cGAMP or other STING agonists on its own or in combination with irradiation have shown its excellent ability to enhance local proinflammatory response and improve antitumor immunity. Mechanistic studies indicate that activation of the STING pathway within tumor-resident antigen presenting cells (APCs) leading to type I IFNs production is indispensable for generation of adaptive immune response against tumors. See, Deng, et al. *Immunity* 41, 843-852, (2014); Park, et al. *Sci Transl Med* 10, (2018); Baird, et al. *Cancer Res* 76, 50-61, (2016); Fuertes, et al. *J Exp Med* 208, 2005-2016, (2011); Diamond, et al. *J Exp Med* 208, 1989-2003, (2011); Woo, et al. *Immunity* 41, 830-842, (2014).

Although the in situ immunotherapy approach is attractive, there are several apparent disadvantages associated with the intratumoral injection of immunostimulants. This approach is generally limited to accessible tumors, and will become even more challenging if repeated injections are needed for sustaining immune response. Commonly used immunostimulants such as the oligonucleotides CpG and cGAMP containing the phosphodiester bond are susceptible to degradation by phosphodiesterase, and the two phosphodiester bonds in cGAMP restrict its penetration through the plasma membrane. Thus, in order to achieve adequate biological activity, such oligonucleotides are commonly used at relatively high concentrations. However, excessive CpG or cGAMP injected intratumorally can be taken up by tumor cells, which has been reported to induce PD-L1 overexpression in tumor cells or an increase in tumor-infiltrating regulatory T cells (Treg) to have negative impact on antitumor immunity. Moreover, several studies have shown that the intratumoral immunostimulants usually induce local immune response at the injected site, but have limited effect on the distant, uninjected tumor sites, implicating that the local approach may be inadequate to elicit systemic immunity, or the systemic response even if induced may be rendered inactive when exposed to the immunosuppressive tumor microenvironment at distant naïve tumor sites.

BRIEF SUMMARY OF THE INVENTION

Provided herein are compositions containing lipid nanoparticles including components such as therapeutic agents (e.g., nucleic acid therapeutic agents) and targeting components (e.g., components that target antigen presenting cells). In some embodiments, compositions are provided wherein the lipid nanoparticles are calcium phosphate nanoparticles having a lipid coating comprising phosphatidylcholine, wherein the calcium phosphate nanoparticles include the nucleic acid therapeutic, and wherein the nucleic acid therapeutic is a cyclic dinucleotide (e.g., 2'3' cyclic guanosine monophosphate-adenosine monophosphate; 2'3'-cGAMP). In some embodiments, the lipid nanoparticles are liposomes. In some embodiments, the composition is formulated for administration to the lungs of a subject via inhalation, e.g., via a nebulizer.

Also provided herein are methods for treating cancers such as lung cancer. Advantageously, the methods target antigen presenting immune cells for enhancement of their antitumor activity. The methods include administering to a subject in need thereof a therapeutically effective amount of a composition containing lipid nanoparticles as described herein. In some embodiments, lipid nanoparticle compositions are administered in conjunction with radiotherapy.

3

Figure 1A:
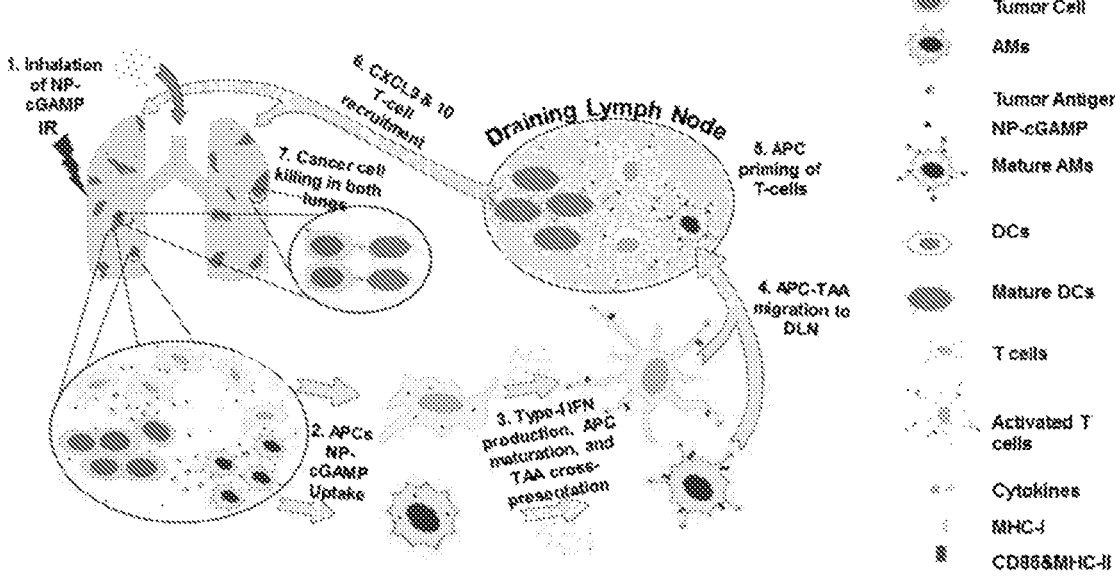
FIG. 1A shows the mode of action of the inhalable nanoparticulate cGAMP (NP-cGAMP) for enhancing antitumor immunity against lung metastases. Inhalation of phosphatidylserine (PS)-coated NP-cGAMP provides targeted delivery of the STING agonist, cGAMP, to antigen presenting cells (APCs) in both irradiated and non-irradiated lung metastases. In addition to enhancing APC maturation, innate immune sensing of immunogenic IR, and cross-presentation of tumor antigen (TAA) to prime effector T cells at the irradiated tumor sites, the inhaled NP-cGAMP promotes pro-inflammatory response in the non-irradiated tumors and facilitates recruitment of TAA-specific effector T cells to lung metastases in both lungs, which contribute to the abscopal effect observed in the non-irradiated tumors.
Figure 1B:
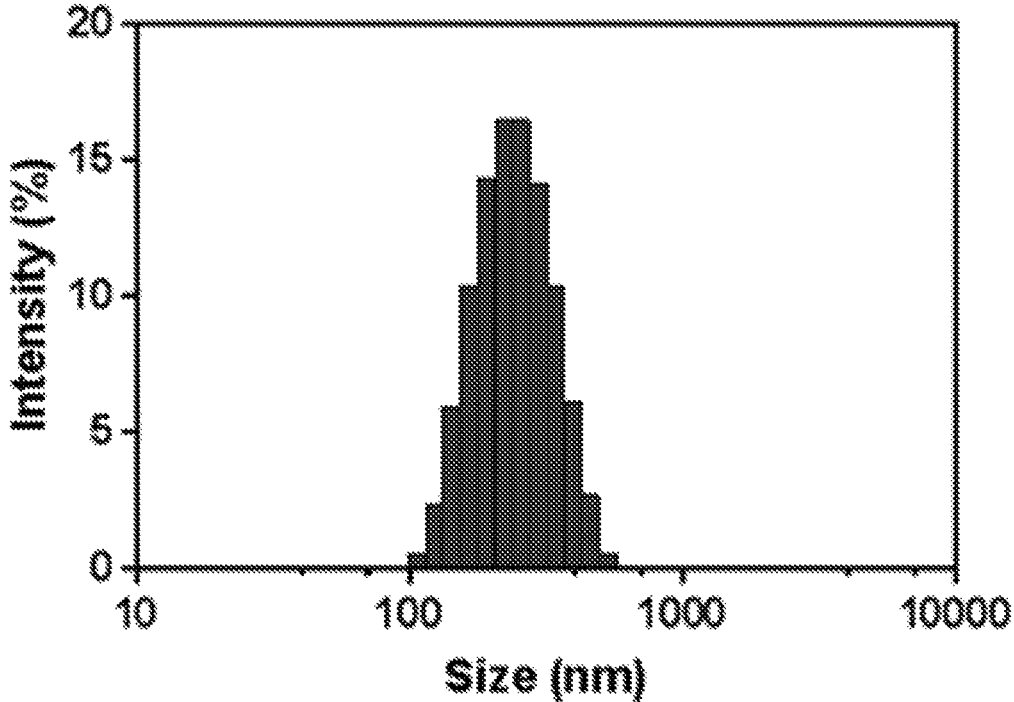
FIG. 1B shows DLS measurement of particle size distribution of NP-cGAMP.
Figure 1C:
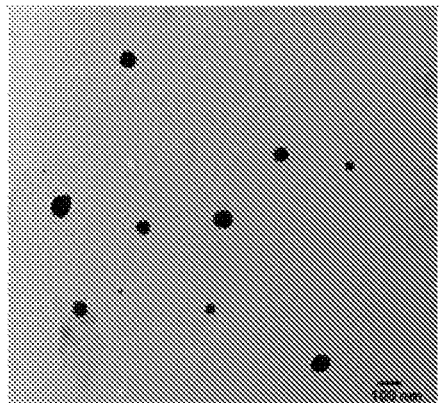
FIG. 1C shows TEM images of NP-cGAMP.
Figure 1D:
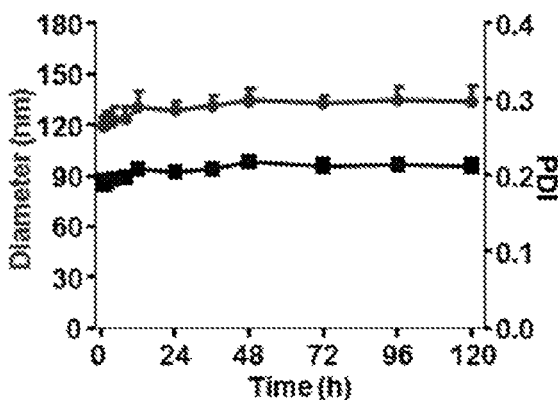
FIG. 1D shows the diameter change and PDI change of NP-cGAMP at pH 7.4 in 10% FBS (37° C.) over time.
Figure 1E:
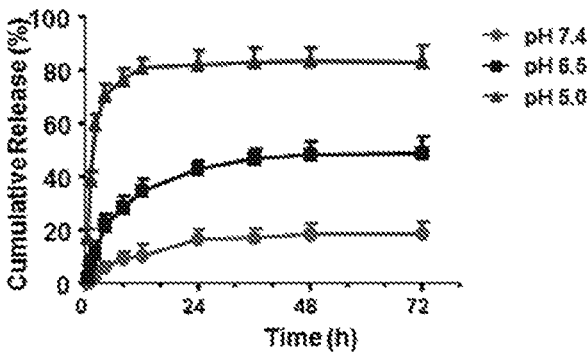

FIG. 1E shows the cumulative release of cGAMP from PS-coated NPs under pH 7.4, pH 6.5, or pH 5.0 at 0.5, 1, 2, 4, 8, 12, 24, 36, 48, and 72 h. Data are shown as mean±SD of 3 independent experiments.

Figure 2A:
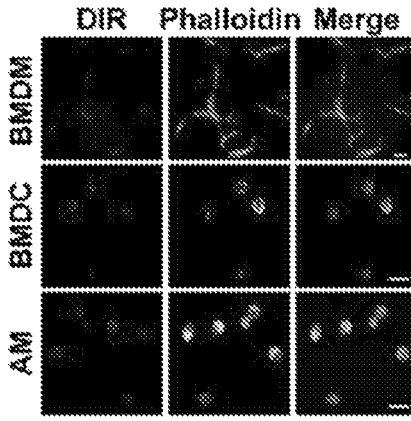

FIG. 2A shows BMDM, BMDC and AM cells that were cultured with DiR-labelled PS-coated NPs for 30 mins, fixed, and co-stained with Phalloidin and DAPI. Intracellular NPs signals were clearly observed. Scale bar=20 μm.

Figure 2B:
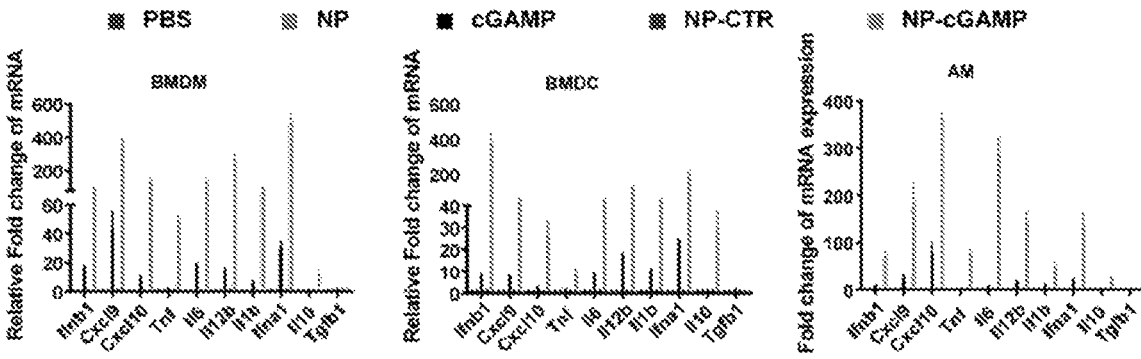

FIG. 2B shows real-time PCR of changes in mRNA levels of inflammatory cytokine genes in BMDM, BMDC, and AM after treatment with free cGAMP (100 nM), NP-cGAMP (100 nM cGAMP) or NP-CTR (2'5'-GpAp as a control of cGAMP) for 4 h. Data were shown as mean±SD of 3 independent experiments.

Figure 2C:
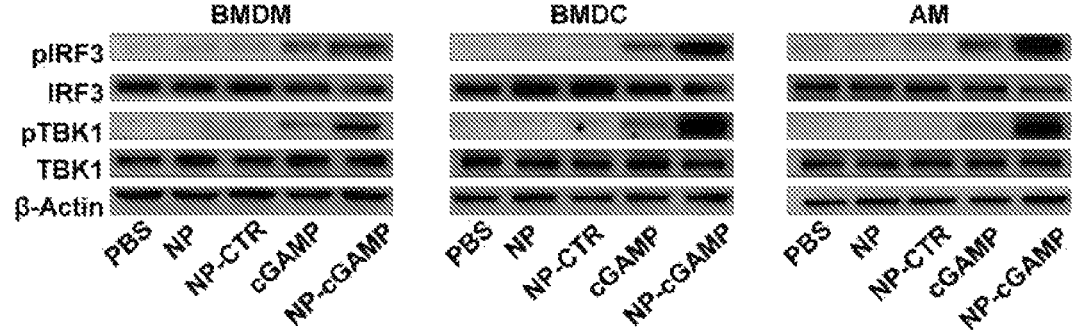

FIG. 2C shows Western blot detection of STING pathway activation in BMDM, BMDC and AM after treatment, as indicated, for 8 h; representative of three independent experiments.

Figure 2D:
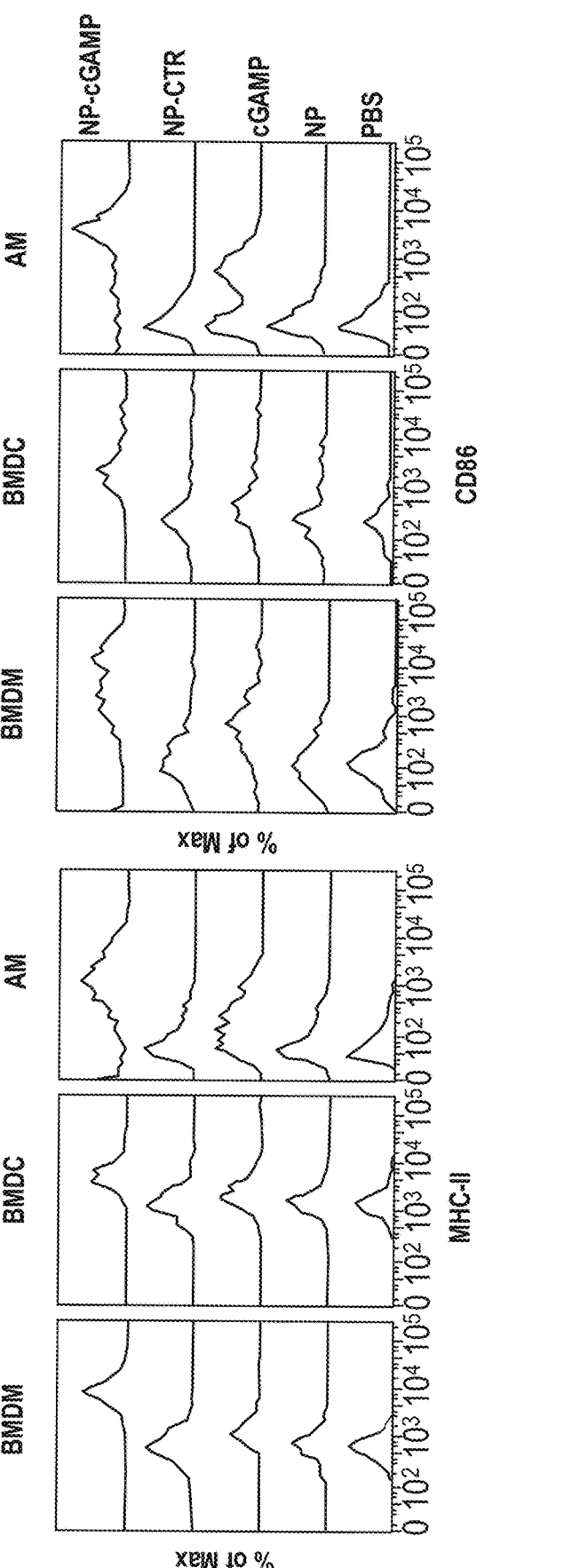

FIG. 2D shows FACS analysis of expression of the co-stimulatory molecule CD86 and MHC-II in BMDM, BMDC and AMs after indicated treatment for 8 h. Repeated 3 times with similar results.

Figure 2E:
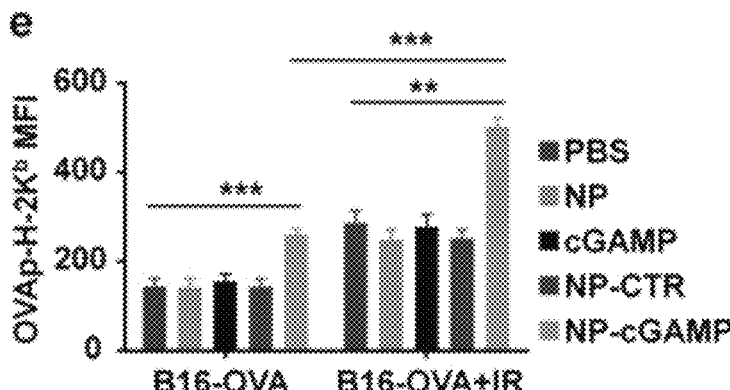

FIG. 2E shows B16-OVA cells treated with/without a single dose of 20Gy IR were continued to culture for 72 h and then co-cultured with BMDCs under indicated treatment for 18 h. Expression of the OVA peptide SIINFEKL-MHC I molecule Kb complex on the surface of BMDCs was analyzed by FACS. Data were shown as mean±SD of 3 independent experiments.

Figure 2F:
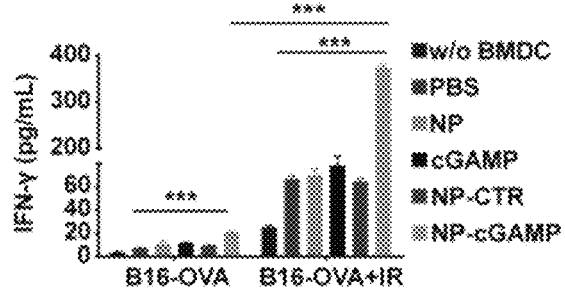

FIG. 2F shows ELISA assay of IFN-γ production from OT-1 CD8+ T cells in vitro. CD8+ T cells isolated from the OT-1 mouse spleen were added into the above mixture of BMDCs with IR or non-IR treated B16-OVA cells (BMDCs: Tcells=1:5) and further incubated for 18 h. IFN-γ concentrations in supernatant were determined by ELISA assay. Data were shown as mean±SD of 3 independent studies. * p<0.05;  p<0.01; * p<0.001 by Student's T-test.

Figure 3:
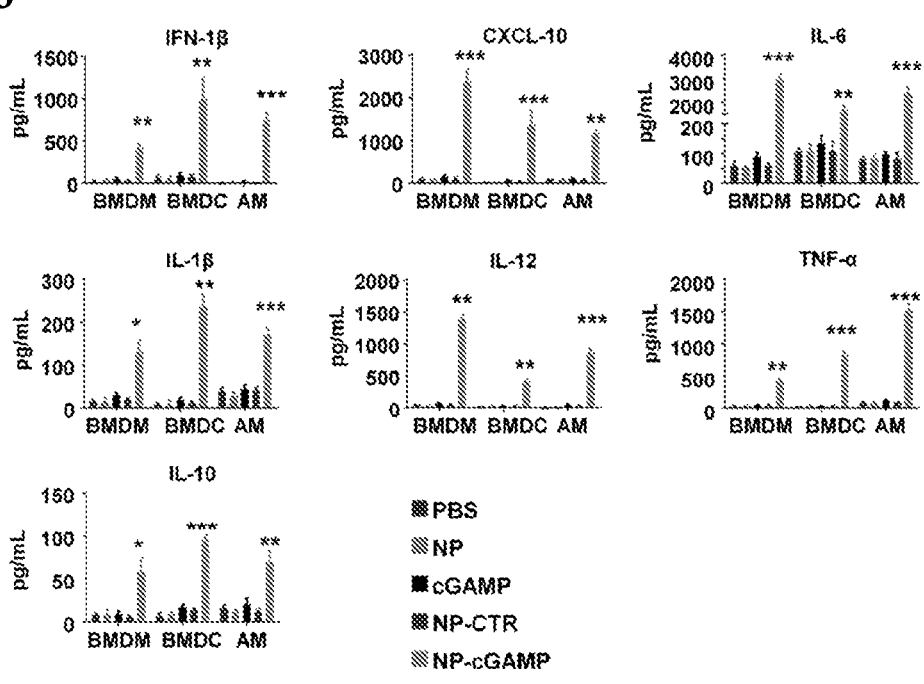

FIG. 3 shows that NP-cGAMP induces APCs to produce type I IFN and other cytokines. Cell culture medium from BMDM, BMDC, and AM after indicated treatment for 8 h was analyzed by ELISA. Data shown as mean±SD of 6 independent experiments. * p<0.05;  p<0.01; * p<0.001 by Student's T-test.

Figure 4:
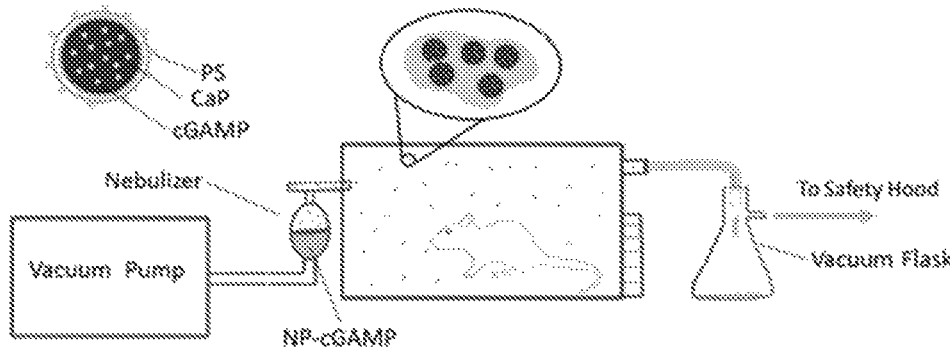

FIG. 4 shows a scheme for preparation of nebulized aerosols containing PS-coated NP-cGAMP inhaled by mice under study. NP-cGAMP was aerosolized by a vacuum pump supplying pressure to a medical nebulizer, and was delivered to a custom-fabricated airtight chamber, where droplets were inhaled by mice. Excessive droplets were evacuated to a safety hood through a vacuum flask.

Figure 5A:
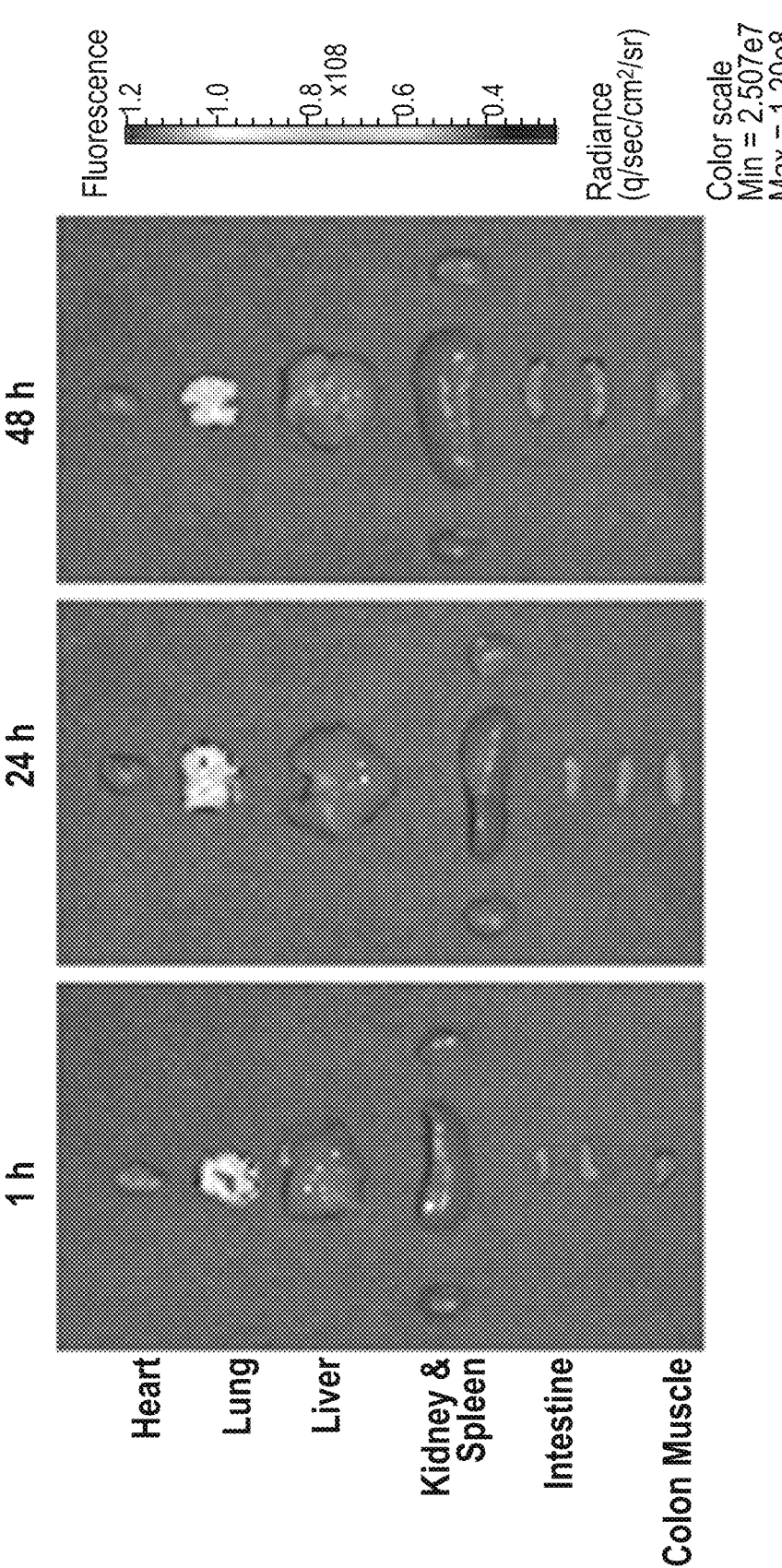

FIG. 5A shows representative ex vivo fluorescence imaging of major organs dissected from 4T1-luc lung metastases-bearing mice at 1, 24 and 48 h post inhalation of DiR-labelled PS-coated NPs. Light signals were exclusively from both lungs.

Figure 5B:
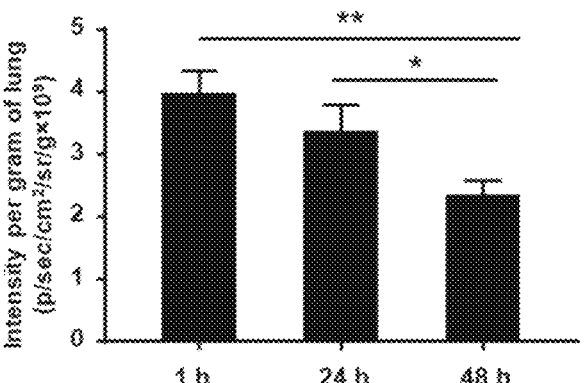

FIG. 5B shows quantification (n=3/time) of the signal detected in FIG. 5A.

Figure 5C:
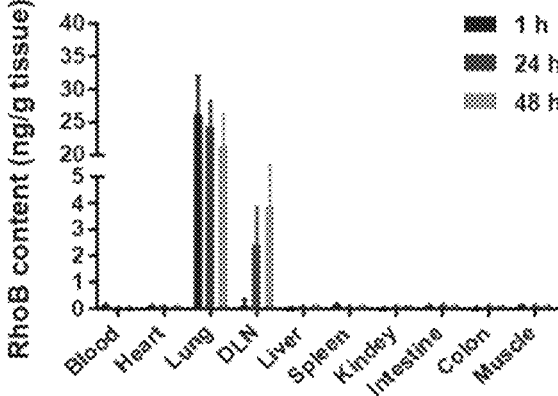

FIG. 5C shows HPLC measurements of concentrations of PS-coated NPs labelled with RhoB in various tissues of the 4T1-luc lung metastasis mice post inhalation (n=3/time) were consistent with the IVIS imaging data. With the lung concentrations decreasing over time, NP increased in DLNs.

Figure 5D:
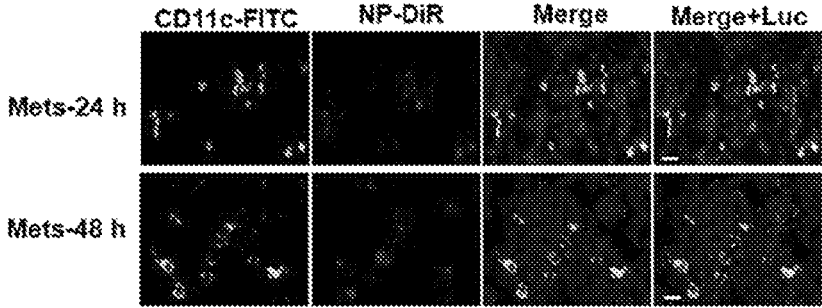

FIG. 5D shows metastases-bearing lung tissues obtained 24 h and 48 h post inhalation were subjected to immuno-fluorescent staining. The merged images clearly showed that DiR-labelled NPs co-localized predominantly with CD11c+ APCs. Co-staining of 4T1 tumor cells with anti-luciferase indicated that the PS-NPs were distributed well into individual metastases and captured by intratumoral APCs. DAPI, scale bar=20 μm.

Figure 5E:
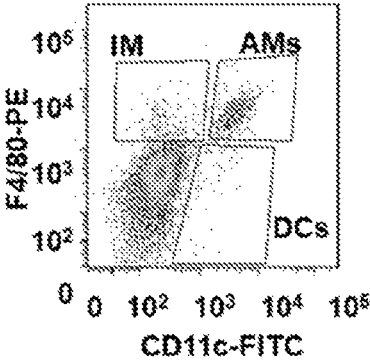

FIG. 5E shows representative FACS characterization of pulmonary APC subsets in 4T1 lung metastasis-bearing lungs: alveolar macrophages (AMs; CD11c+ F4/80+), interstitial macrophages (IMs; CD11c− F4/80+) and DCs (CD11c+ F4/80−).

Figure 5F:
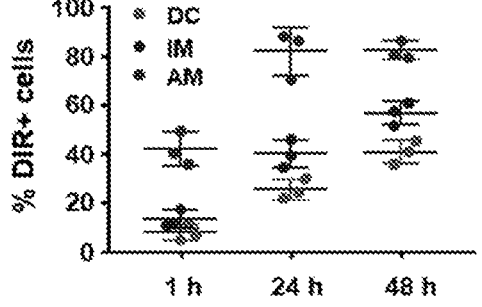

FIG. 5F shows percentages of DiR positive AMs, IMs and DCs were determined at 1, 24 and 48 h after inhalation of NP-DiR.

Figure 5G:
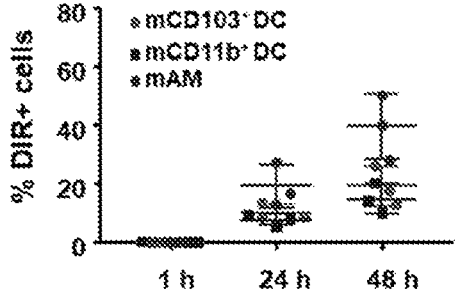

FIG. 5G shows DiR positive mAM, mDC103+, mCD11b+ DCs that migrated from lungs, which were identified in DLNs at different times post inhalation. Data are shown as mean±SD of 3 mice.

Figure 6A:
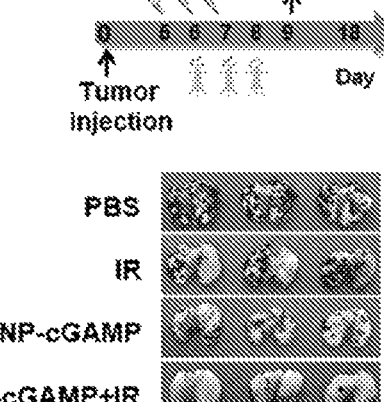

FIG. 6A shows representative lungs (n=3) from treatment groups (n=6/group) in a B16-OVA melanoma lung metastasis model.

Figure 6B:
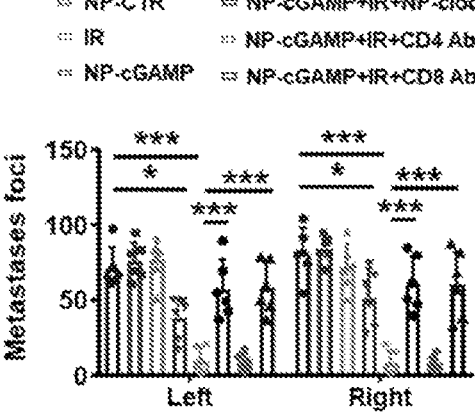

FIG. 6B shows the number of metastatic lung foci counted on each lung in FIG. 6A under a dissecting microscope.

Figure 6C:
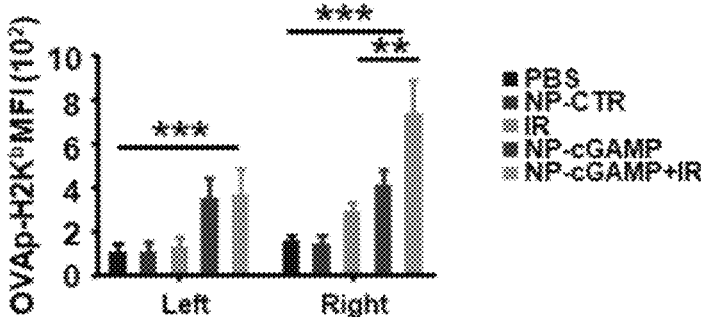

FIG. 6C shows expression of the complex of OVA peptide SIINFEKL-MHC I molecule Kb on CD103+ (CD11c+ CD103+ CD11b−) DCs in the left and right lungs. Data shown as mean±SD (n=6). * p<0.05;  p<0.01; * p<0.001 by Student's t-test.

Figure 6D:
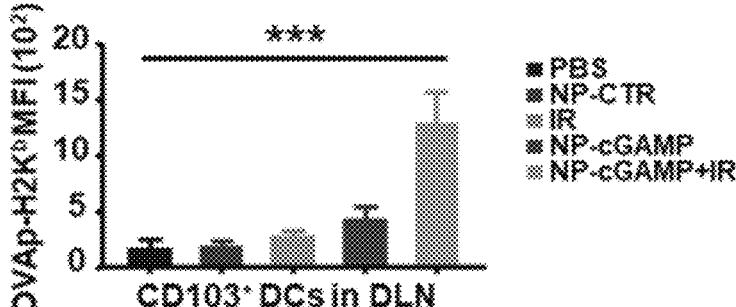

FIG. 6D shows expression of the complex of OVA peptide SIINFEKL-MHC I molecule Kb in DLNs (n=6), as assessed by FACS on Day 9 (24 h after the last inhalation). Data shown as mean±SD (n=6). * p<0.05;  p<0.01; * p<0.001 by Student's t-test.

Figure 6E:
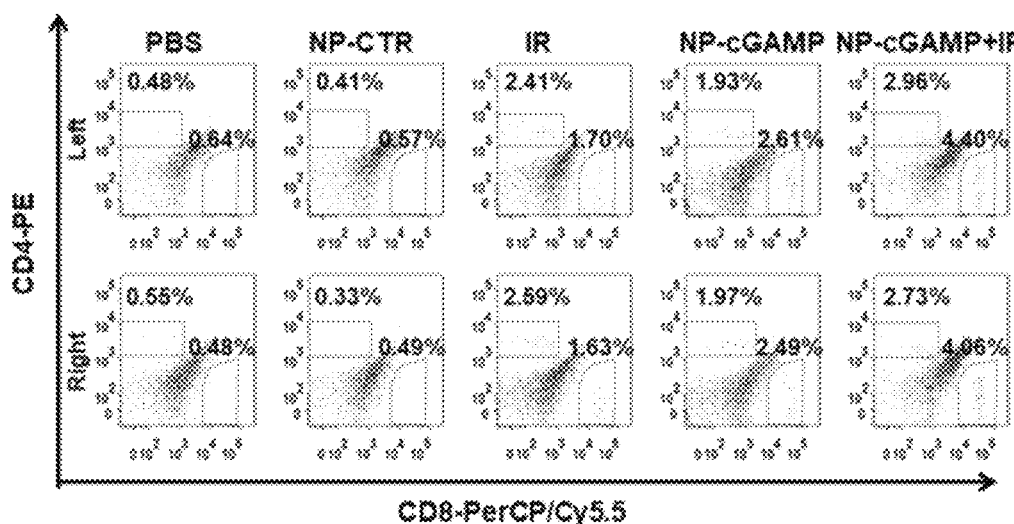

FIG. 6E shows the number of CD8+ and CD4+ T cells in metastases-bearing left and right lung (n=6), as quantified by FACS.

Figure 6F:
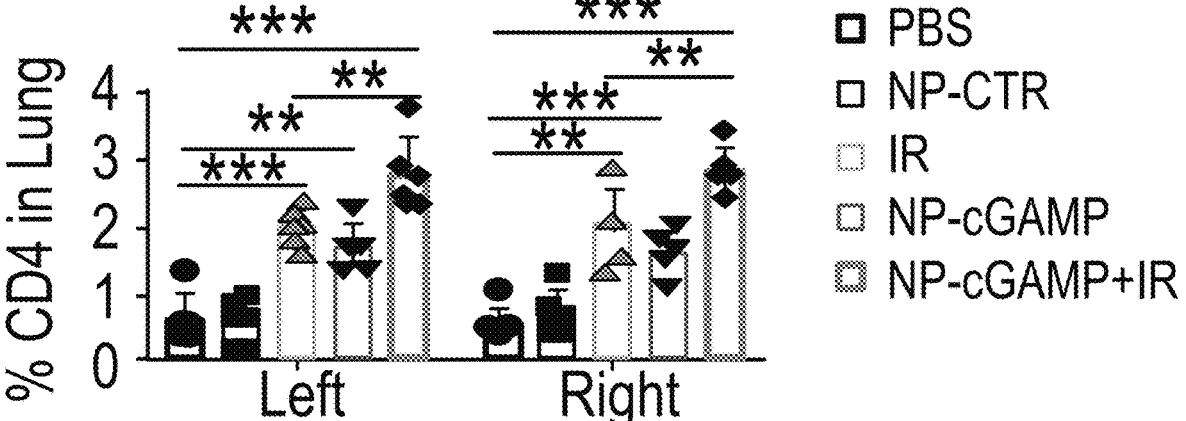

FIG. 6F shows the number of CD8+ and CD4+ T cells in metastases-bearing left and right lung (n=6), as quantified by FACS. Data shown as mean±SD (n=6). * p<0.05;  p<0.01; * p<0.001 by Student's t-test.

Figure 6G:
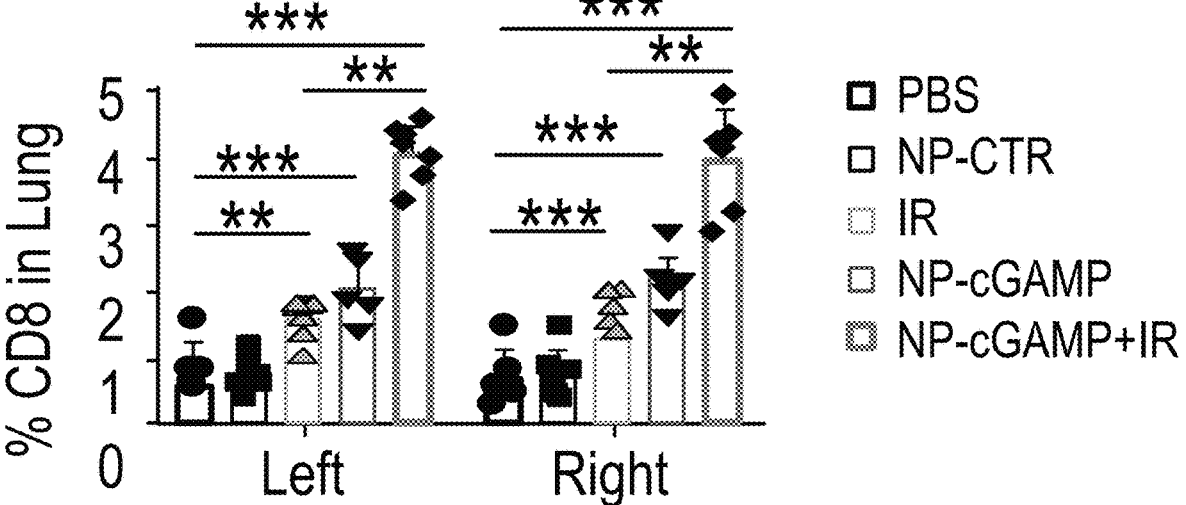

FIG. 6G shows the number of CD8+ and CD4+ T cells in metastases-bearing left and right lung (n=6), as quantified by FACS. Data shown as mean±SD (n=6). * p<0.05;  p<0.01; * p<0.001 by Student's t-test.

Figure 6H:
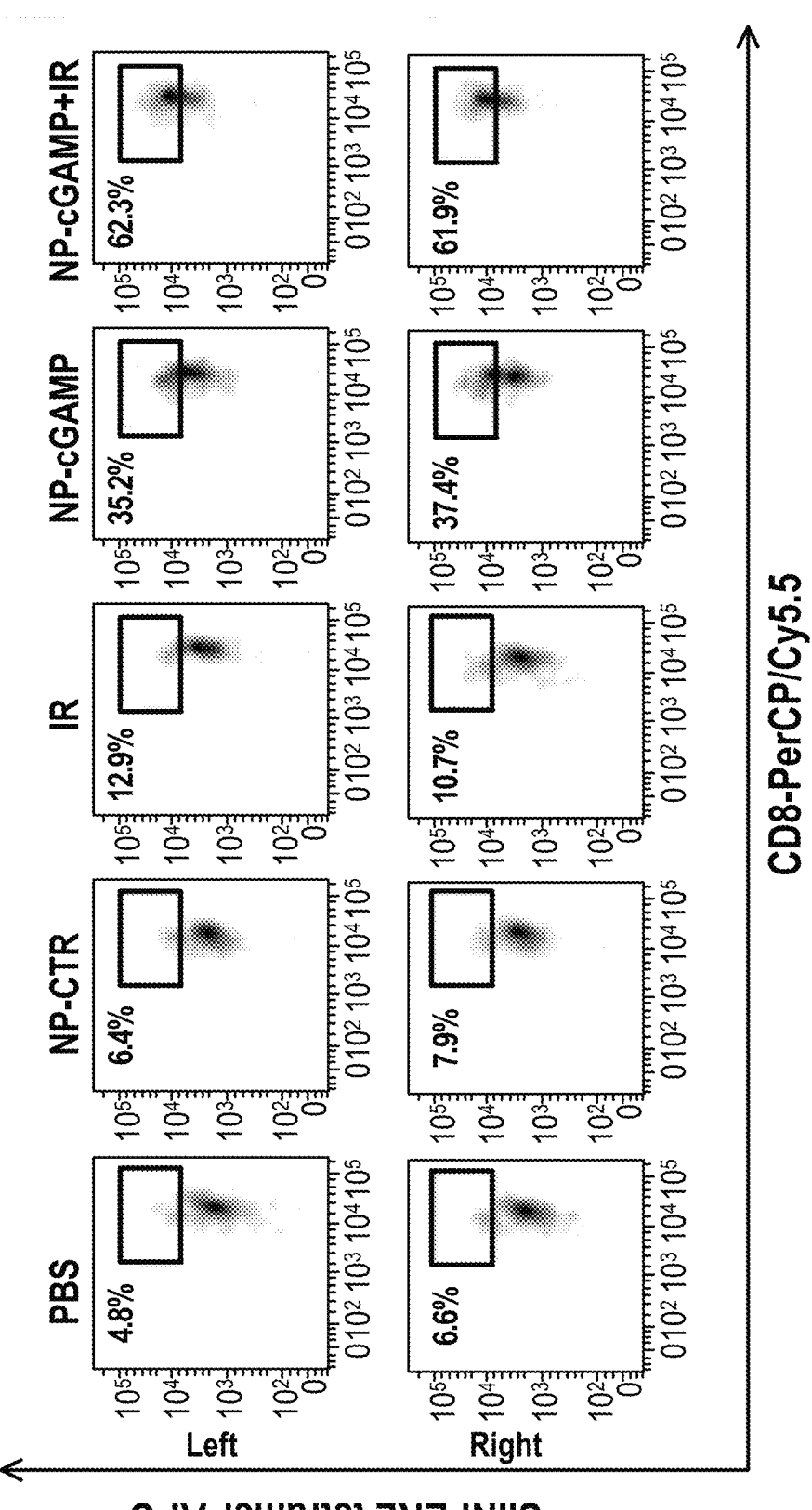

FIG. 6H shows the percentages of the SIINFEKL tetramer+ CD8+ T cells in the total of CD8+ T cells in both lungs, as assessed by FACS on day 9.

Figure 6I:
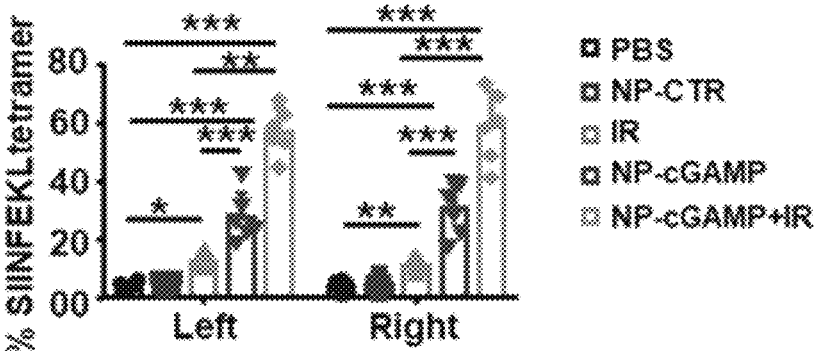

FIG. 6I shows the percentages of the SIINFEKL tetramer+ CD8+ T cells in the total of CD8+ T cells in both lungs, as assessed by FACS on day 9. Data shown as mean±SD (n=6). * p<0.05;  p<0.01; * p<0.001 by Student's t-test.

Figure 6J:
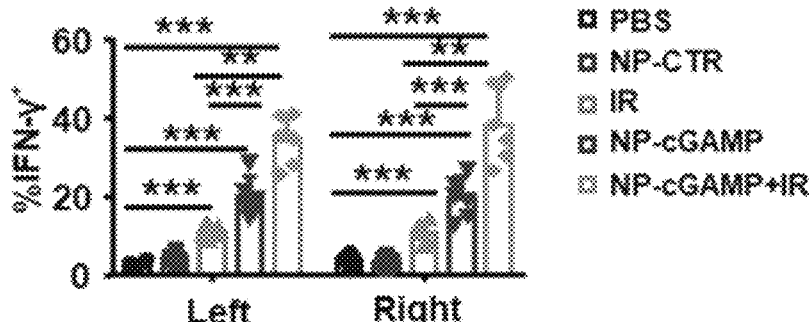

FIG. 6J shows the percentages of intracellular IFN-γ+ SIINFEKL tetramer+ CD8+ T cells in the total of CD8+ T cells, quantified for the left and right lung in treatment groups as indicated. Data shown as mean±SD (n=6). * p<0.05;  p<0.01; * p<0.001 by Student's t-test.

Figure 7:
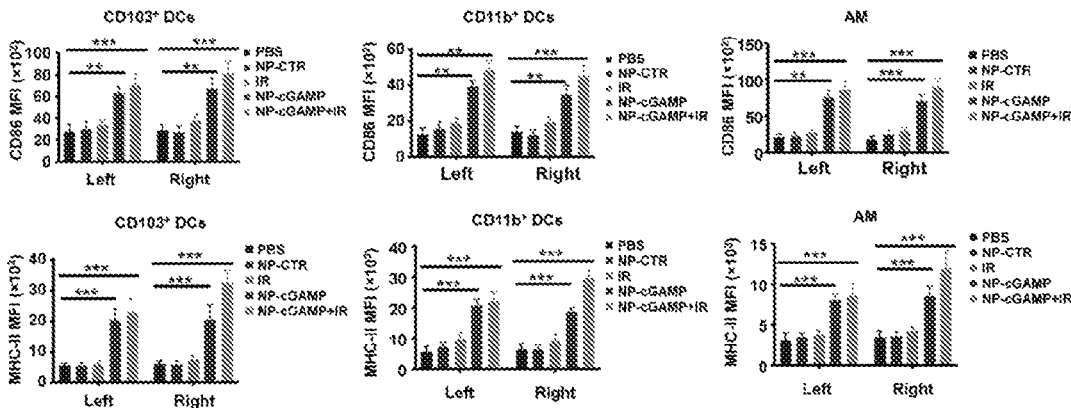

FIG. 7 shows In vivo activation of APCs in B16-OVA lung metastases by inhalation of NP-cGAMP. 24 h after the last inhalation, the mice under indicated treatment were sacrificed and both metastases-bearing lungs were dissected for FACS analysis of the co-stimulatory molecule, CD86 on CD103+ DCs (top left), DC11b+ DCs (top middle) and AM (top right). (bottom) Similarly, MHC-II expressions on DCs and AMs were quantified. Data shown as mean±SD of 6 mice/group.  p<0.01; * p<0.001 by Student's T-test.

Figure 8A:
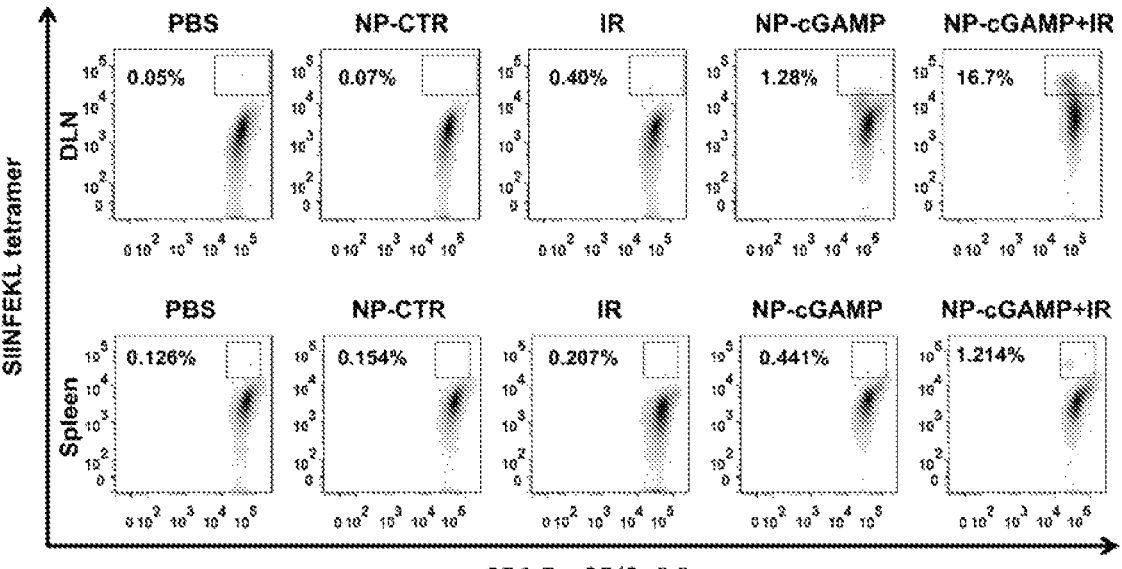

FIG. 8A shows SIINFEKL tetramer+ OVA-specific CD8 T cells, as analyzed by FACS, in lung DLNs and spleen obtained on Day 9 (24 h after the last inhalation) from mice in a study of NP-cGAMP/radiation combination therapy.

Figure 8B:
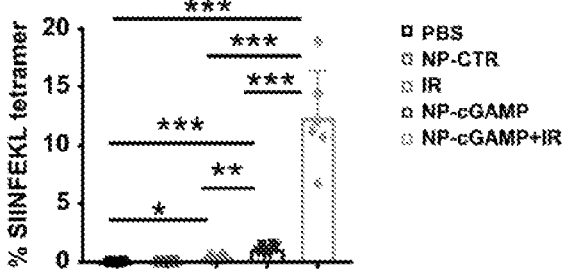

FIG. 8B shows the frequency of SIINFEKL tetramer[+] CD8[+] T cells in DLNs. Data shown as mean±SD (n=6). *p<0.05; p<0.01; *p<0.001 by Student's t-test.

Figure 8C:
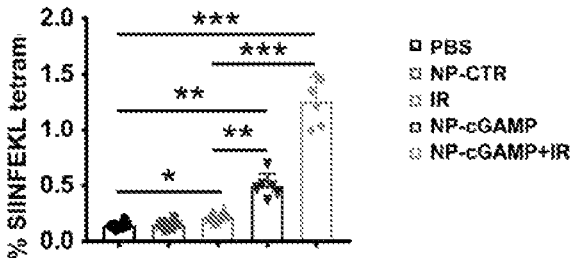

FIG. 8C shows the frequency of SIINFEKL tetramer[+] CD8[+] T cells in spleen. Data shown as mean±S D (n=6). *p<0.05; p<0.01; *p<0.001 by Student's t-test.

Figure 8D:
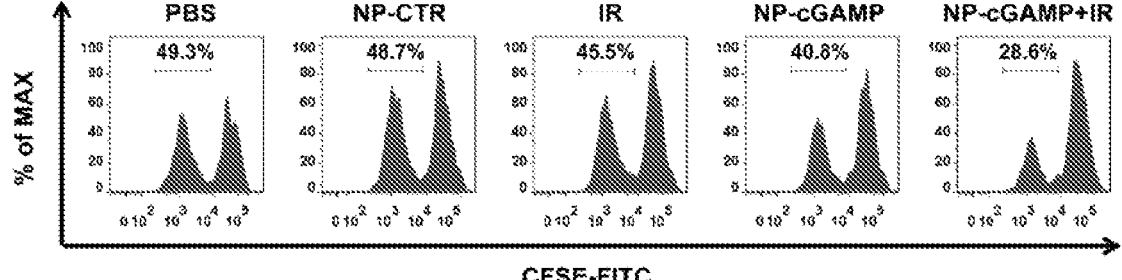

FIG. 8D shows the results of an in vivo VITAL assay. Spleen cells from naïve C57BL/6 mice were isolated and half of the cells were pulsed with OVA257-264 for 2 h in complete medium. The non-pulsed and OVA-pulsed cells labelled with high (0.5) or low (0.05) CFSE, respectively, were equally mixed and injected i.v. into the mice with indicated treatment (Day 18 post tumor implant), and 16 h later blood was drawn for FACS analysis. Representative percentages of the low CFSE were indicated.

Figure 8E:
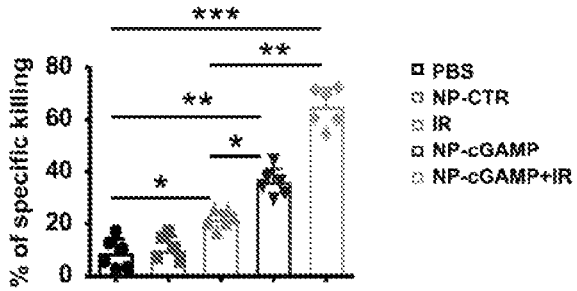

FIG. 8E shows that NP-cGAMP/radiation combination treatment achieved maximal killings of the OVA-splenocytes. Data shown as mean±SD (n=6). *p<0.05; p<0.01; *p<0.001 by Student's t-test.

Figure 9A:
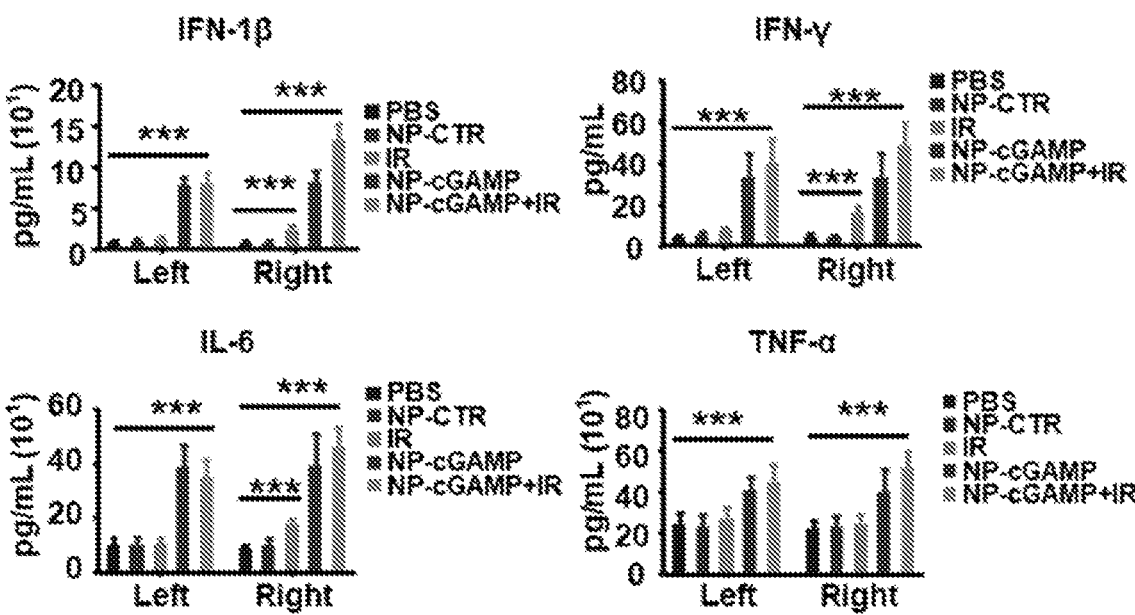

FIG. 9A shows quantification of cytokines by ELISA assay in supernatants of homogenized samples prepared from metastases-bearing lungs obtained on Day 9 (24 h after the last inhalation). Samples were separately for the left and right (IR) lung. Data shown as mean±SD (n=6). * p<0.05; p<0.01; * p<0.001 by Student's t-test.

Figure 9B:
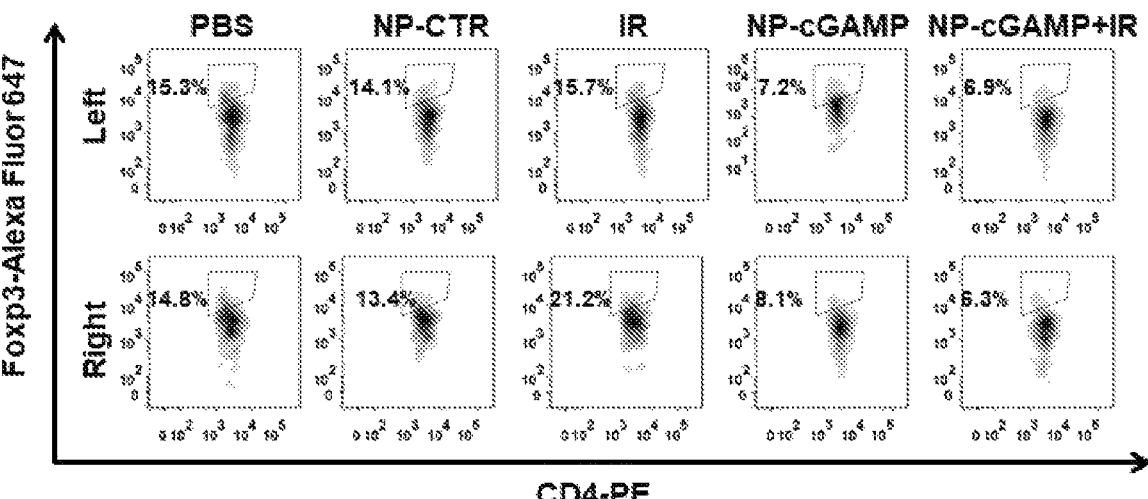

FIG. 9B shows FACS analysis of FoxP3[+] CD4[+] regulatory T cells in metastases-bearing lung tissues shown in FIG. 9A.

Figure 9C:
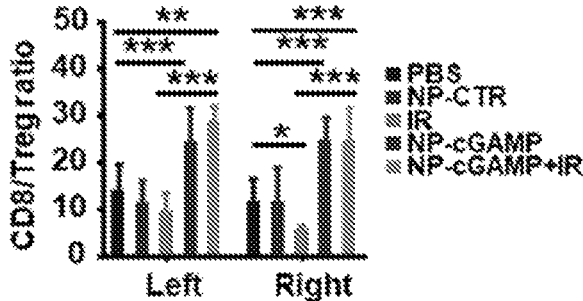

FIG. 9C shows FACS data indicating a significant increase in the ratio of CD8[+] T cells/Tregs in both lungs in the inhalation alone or the combination treatment group, while a significant decrease in the ratio was detected in the irradiated right lung. Data shown as mean±SD (n=6). * p<0.05; p<0.01; * p<0.001 by Student's t-test.

Figure 10A:
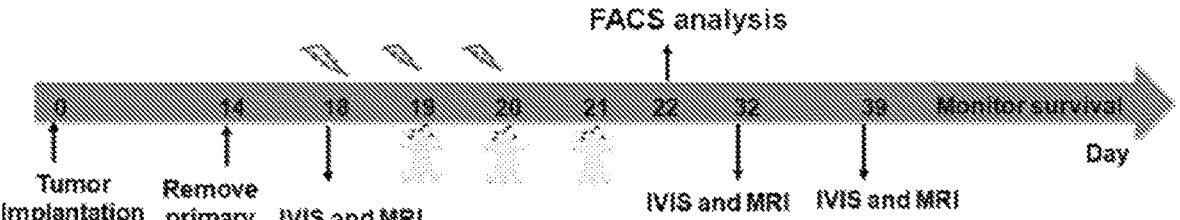
Figure 10A:
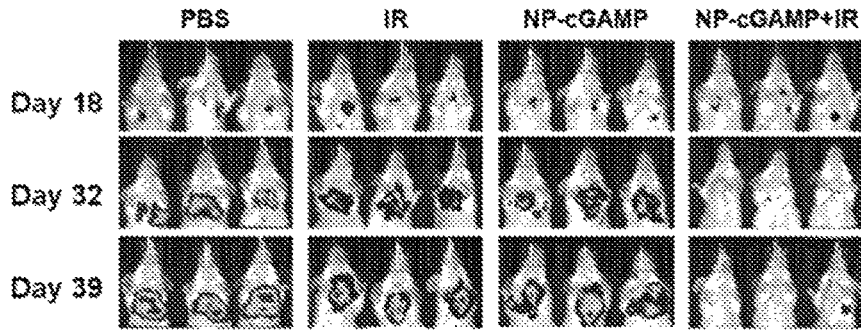

FIG. 10A shows IVIS images of representative animals from treatment groups in a study of the abscopal effects of radiotherapy against 4T1 breast cancer lung metastases when combined with NP-cGAMP.

Figure 10B:
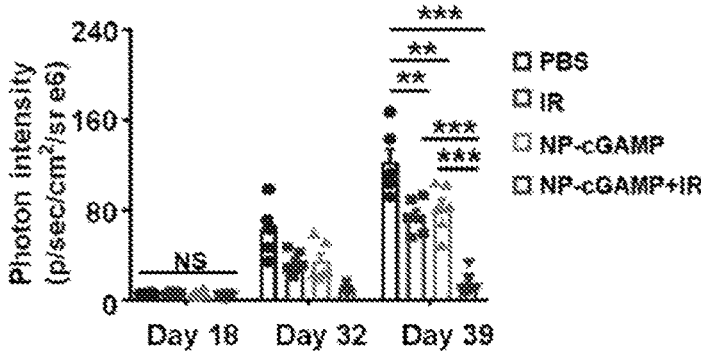

FIG. 10B shows quantitative BLI light intensity of the chest for the animals in FIG. 10A. Data were shown are mean±SD of 6 mice.

Figure 10C:
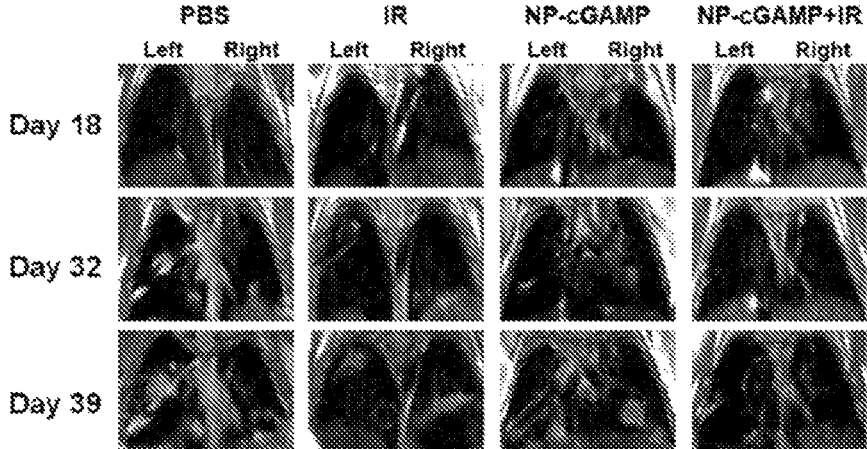

FIG. 10C shows longitudinal MRI T2-weighted imaging follow-up of a representative mouse chest from each treatment group. Data are shown as mean±SD of 4-5 mice. * p<0.05;  p<0.01; * p<0.001 by Student's T-test.

Figure 10D:
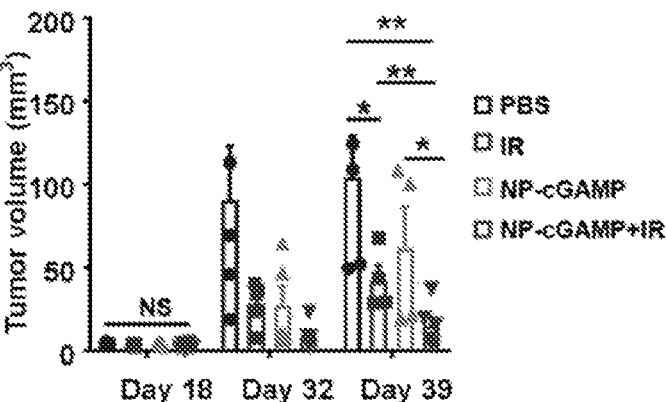

FIG. 10D shows the quantitation of tumor volume as assessed by MRI. Data are shown as mean±SD of 4-5 mice. * p<0.05;  p<0.01; * p<0.001 by Student's T-test.

Figure 10E:
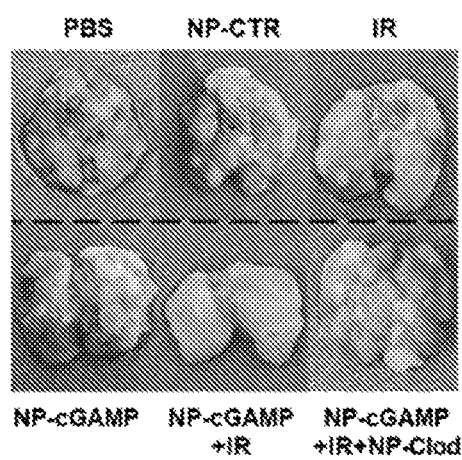

FIG. 10E shows representative ex vivo from each treatment group on Day 39. Also included were a group receiving inhalation of NP-CTR (2'5'-GpAp as a control of cGAMP) for 3 doses; as well a group receiving NP-cGAMP plus IR, in which NP-clodronate was administered via inhalation 6 h before each of the 3 NP-cGAMP inhalations to deplete pulmonary APCs.

Figure 10F:
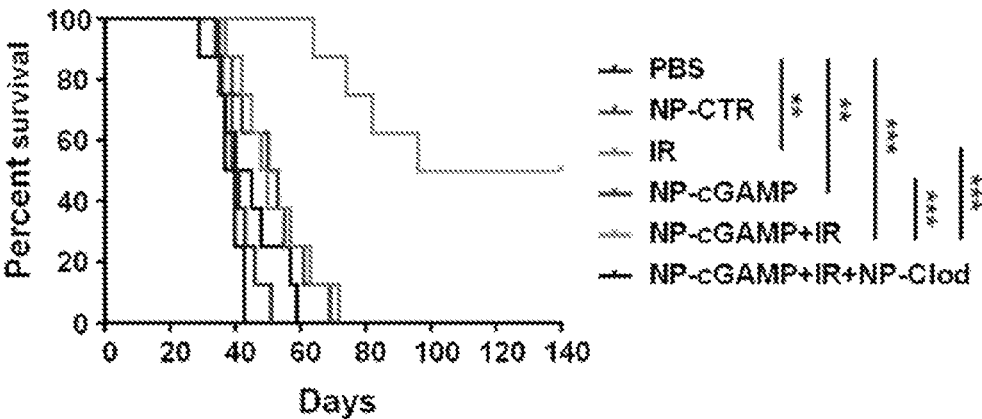

FIG. 10F shows Kaplan-Meier survival curves of the treatment groups up to 140 days after tumor (n=8/group) were plotted and statistically analyzed by log-rank test, * p<0.05;  p<0.01; * p<0.001.

Figure 11:
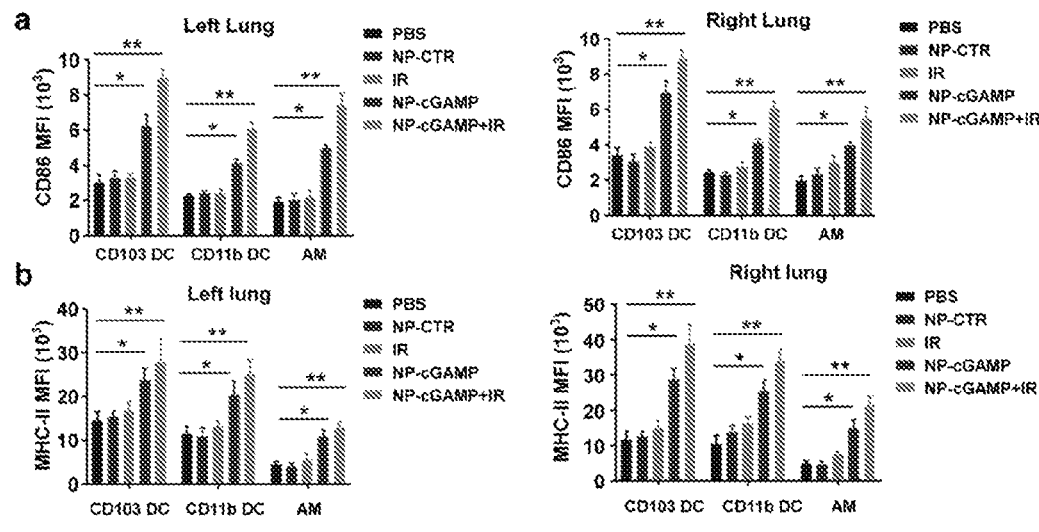

FIG. 11 shows that inhalation of NP-cGAMP plus IR activates APCs in 4T1-luc lung metastases. 24 h after the last inhalation, the mice under indicated treatment were sacrificed and both metastases-bearing lungs were dissected for FACS analysis. Significantly increased expressions of CD86 molecule (top panels) and MHC-II (bottom panels) on APCs were observed in both lungs of the mice with inhalation of NP-cGAMP with/without IR treatment. Data shown as mean±SD of 6 mice/group. * p<0.05;  p<0.01; * p<0.001 by Student's T-test.

Figure 12:
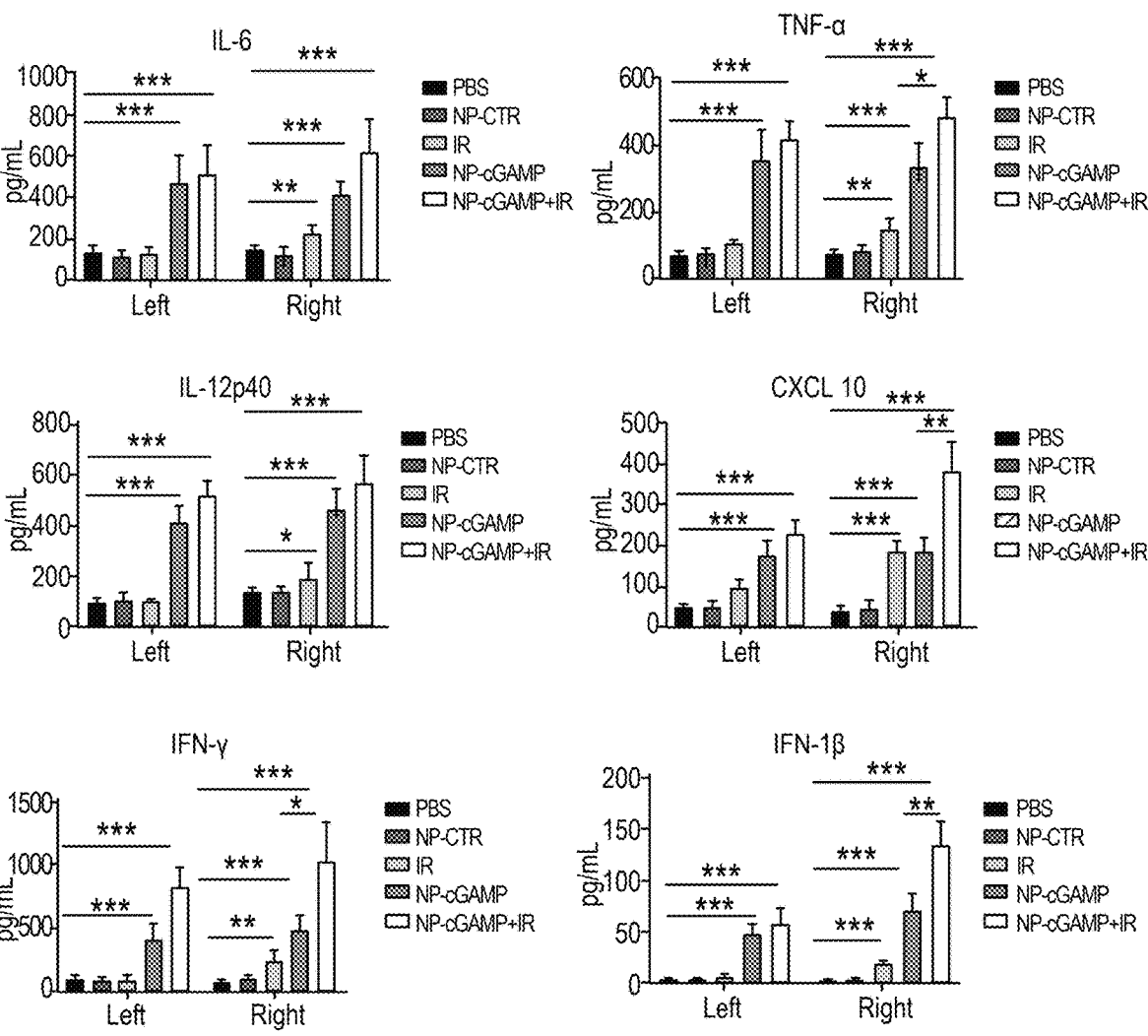

FIG. 12 shows that inhalation of NP-cGAMP stimulates pro-inflammatory response in both irradiated and non-irradiated lung metastases. 24 h after the last inhalation, the mice under indicated treatment were sacrificed and both metastases-bearing lungs were dissected and analyzed by ELISA. Type I IFN, IFN-1β and other proinflammatory cytokines, TNFα, IL-6, IL-12p40 and IFNγ, as well as the chemokine, CXCL10 were found to be significantly higher in both lungs of the mice with inhalation of NP-cGAMP with/without IR treatment. Data shown as mean±SD of 3 mice/group. * p<0.05;  p<0.01; * p<0.001 by Student's T-test.

Figure 13:
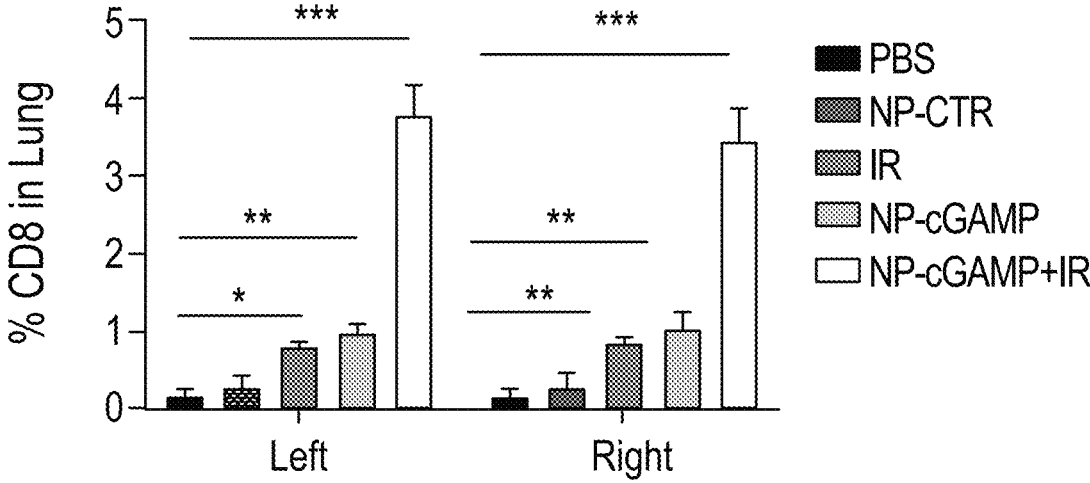
Figure 13:
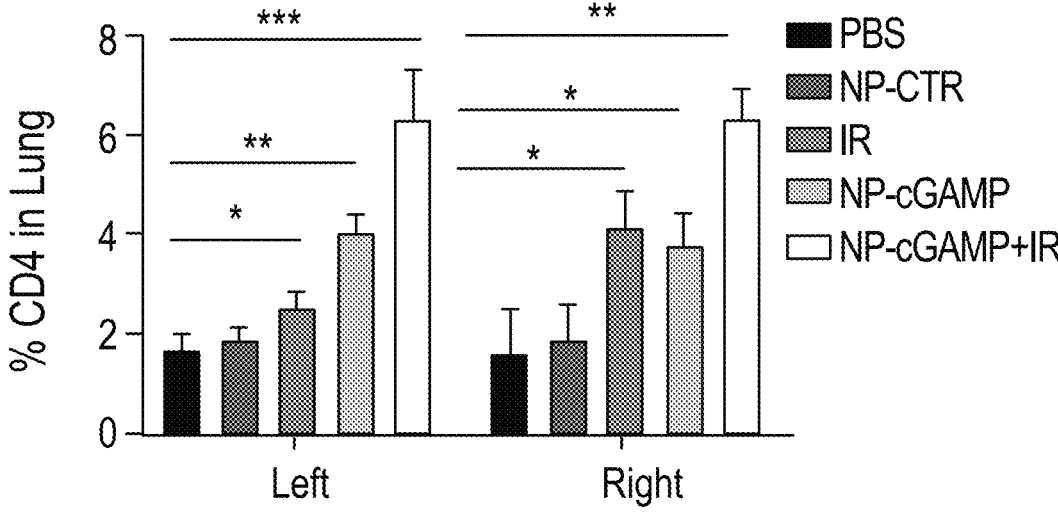

FIG. 13 shows that inhalation of NP-cGAMP plus IR promotes tumor infiltrating leukocytes (TILs) in 4T1-luc lung metastases. 24 h after the last inhalation, the mice under indicated treatment were sacrificed and both metastases-bearing lungs were dissected for FACS analysis. (a and b) CD8[+] and CD4[+] TILs increased significantly in response to inhalation of NP-cGAMP combined with IR. Data shown as mean±SD of 6 mice/group. * p<0.05;  p<0.01; * p<0.001 by Student's T-test.

Figure 14A:
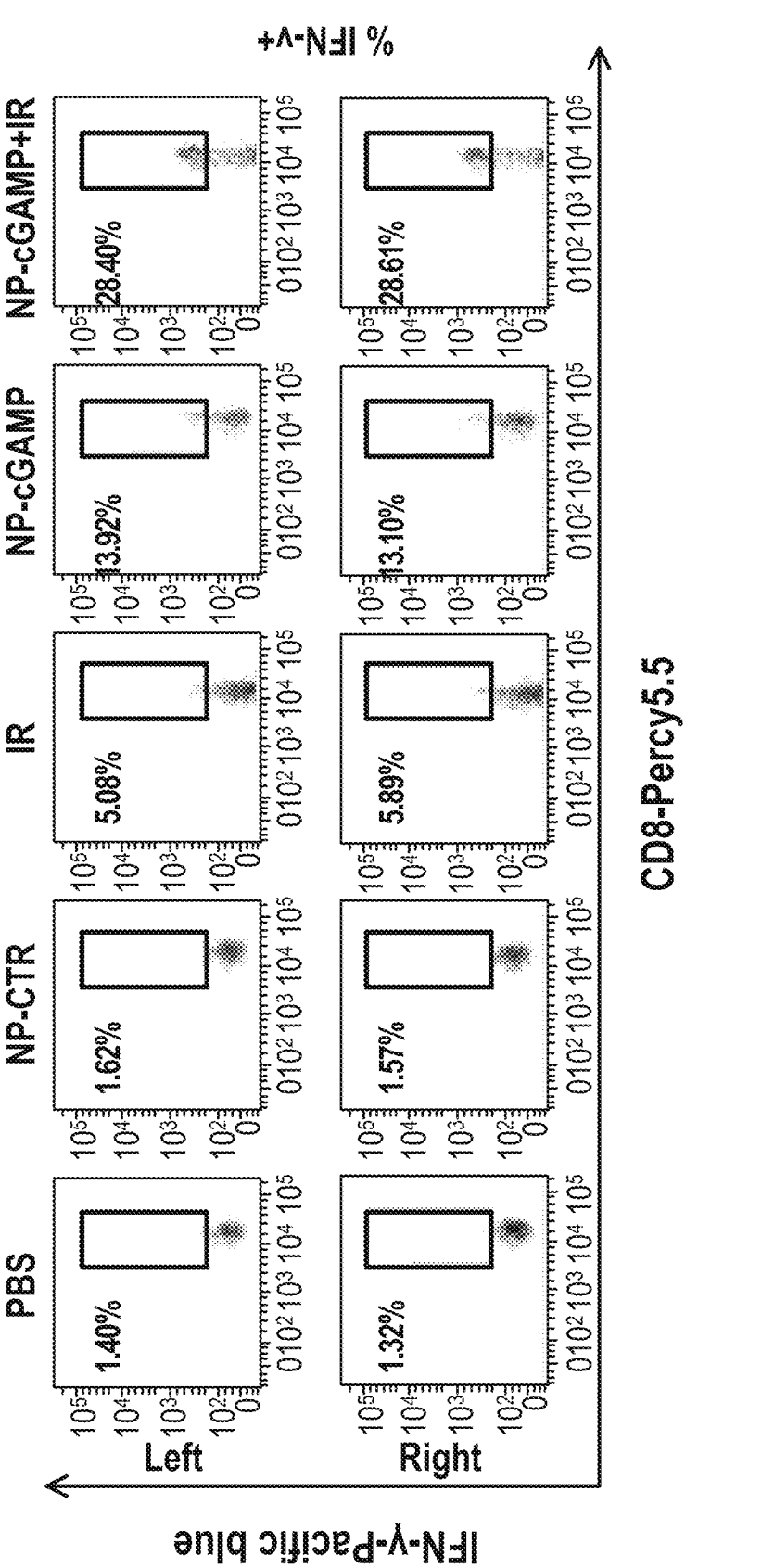

FIG. 14A shows Representative FACS dot plots (n=5,000) of activated CD8[+] T cells by staining intracellular IFNγ from the left and right (IR) lung of each indicated treatment.

Figure 14B:
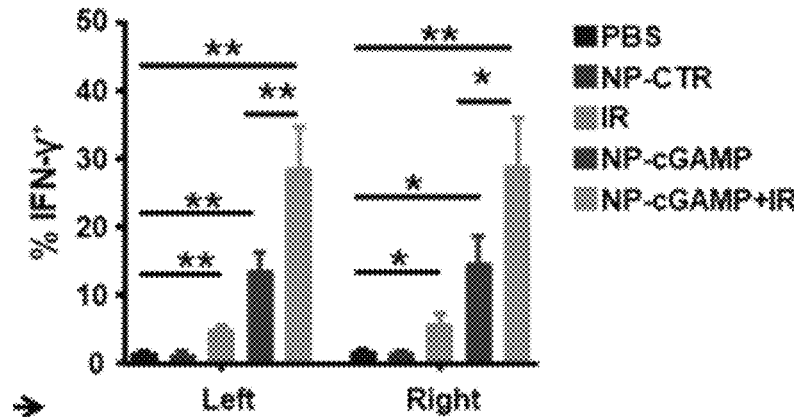

FIG. 14B shows Quantitative analysis of frequency of IFN-γ[+] CD8[+] T cells in the left and right lung. * p<0.05;  p<0.01; * p<0.001 by Student's T-test.

Figure 14C:
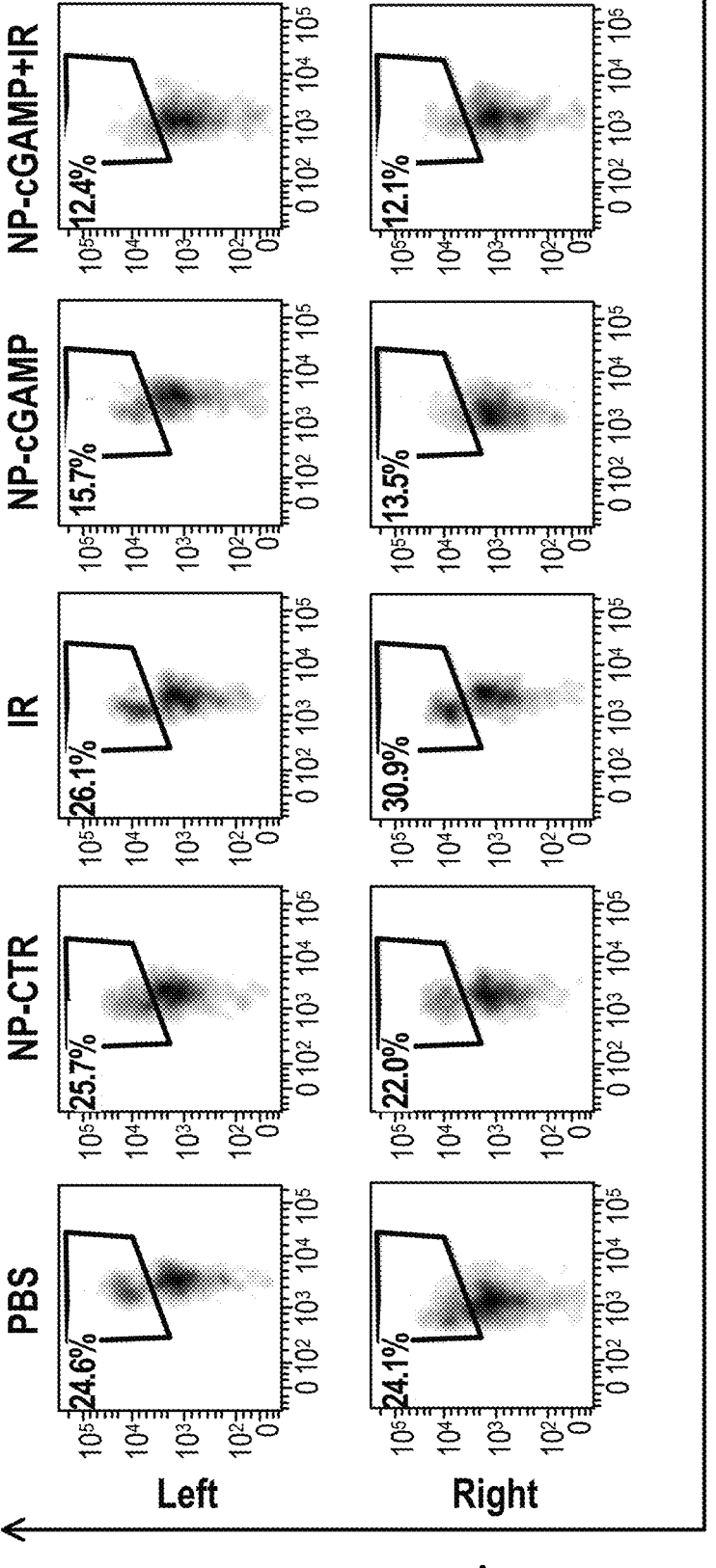

FIG. 14C shows representative FACS analysis of FoxP3[+] CD4[+] Treg cells and ratio of CD8/Treg.

Figure 14D:
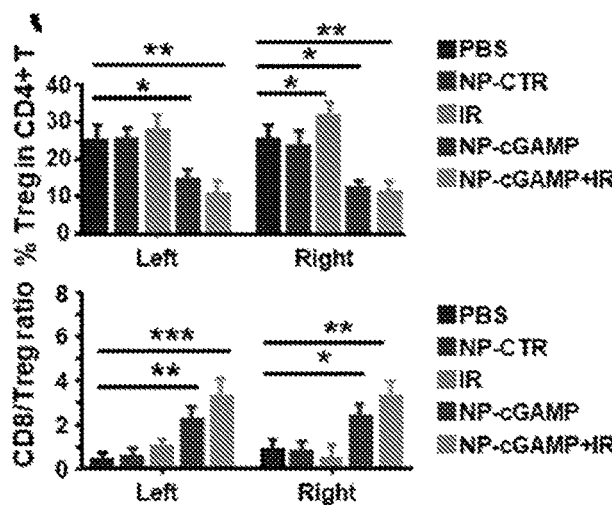

FIG. 14D shows quantitative frequency of FoxP3[+] CD4[+] Treg cells and ratio of CD8/Treg. * p<0.05;  p<0.01; * p<0.001 by Student's T-test.

Figure 14E:
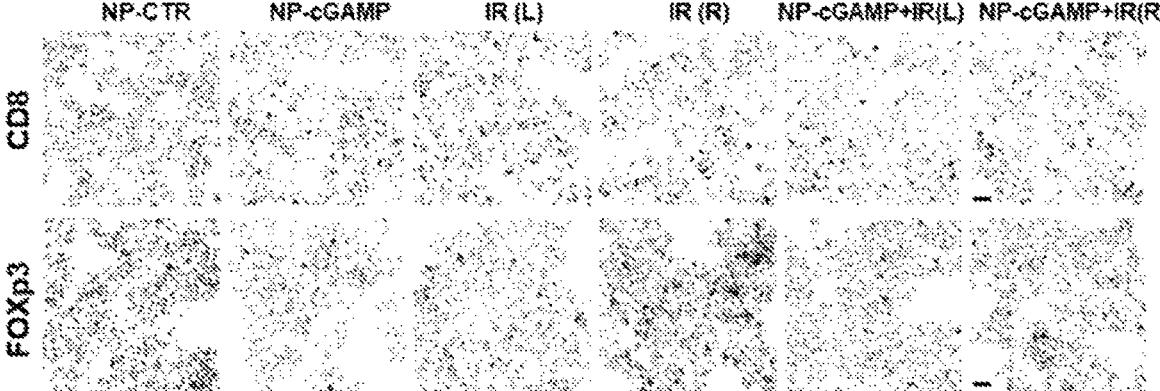

FIG. 14E shows immunohistochemical staining of CD8[+] T cells and FoxP3[+] Tregs in metastases-bearing lung tissues of the mice under indicated treatment. NP-CTR: NP-2'5'-GpAp as a negative control of NP-cGAMP; IR (L) and IR (R): Left (non-irradiated) and right (irradiated) lung of IR alone; the same applies to NP-cGAMP+IR (L) or IR (R). Scale bar=20 μm.

Figure 14F:
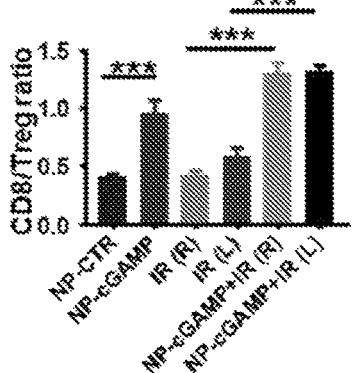

FIG. 14F shows the mean±SD ratio of CD8/Treg in lung metastases. NP-CTR: NP-2'5'-GpAp as a negative control of NP-cGAMP; IR (L) and IR (R): Left (non-irradiated) and right (irradiated) lung of IR alone; the same applies to NP-cGAMP+IR(L) or IR (R). * p<0.05;  p<0.01; * p<0.001 by Student's T-test.

Figure 15:
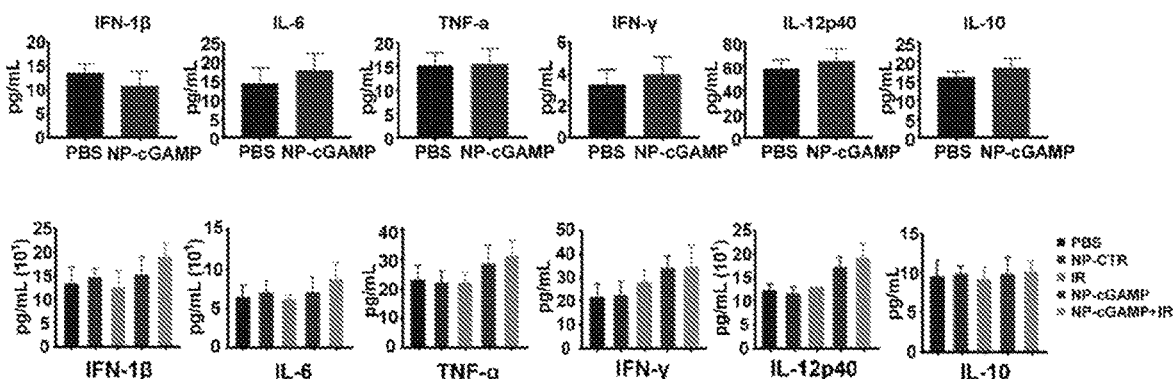

FIG. 15 shows blood cytokine levels in response to inhalation of NP-cGAMP, as measured by ELISA assay. 24 h after inhalation of NP-cGAMP, ELISA assay indicated slight increase in serum IFNγ, IL-6, IL-12p40 and IL-10 but not IFN-β or TNFα in healthy mice (top panels). Similar cytokine profiles without drastic increase were detected in the blood of lung metastases-bearing mice with indicated treatment (bottom panels). mean±SD of 3 mice/group.

Figure 16:
Figure 16:
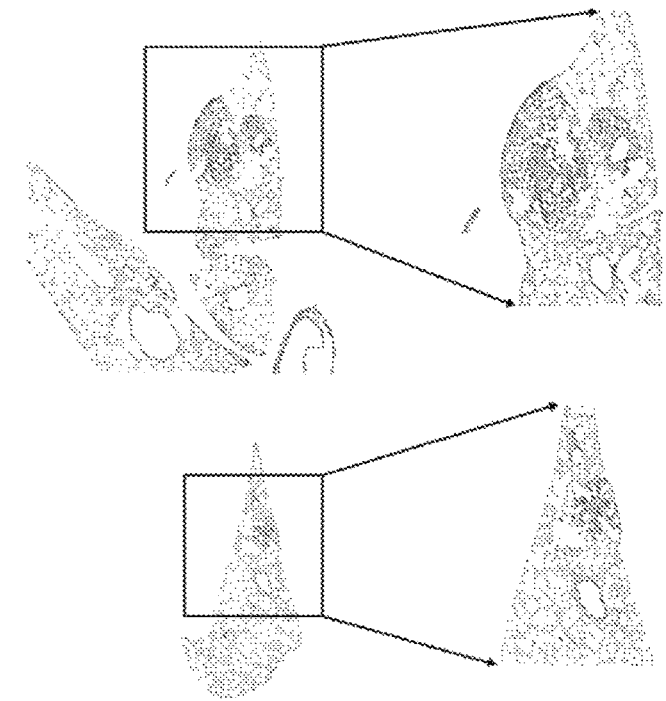

FIG. 16 shows primary lung carcinomas in the lungs of mice employed in an orthotopic model of Lewis lung carcinoma (LLC).

Figure 17A:
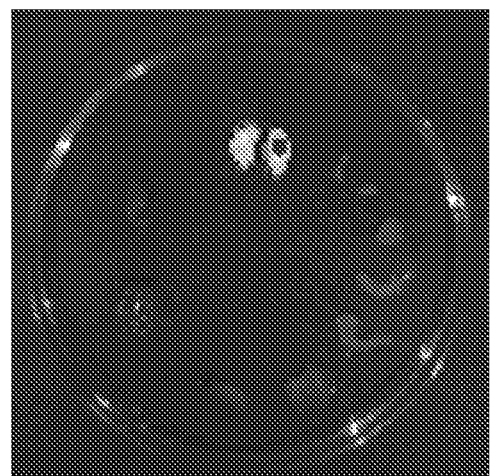
Figure 17A:
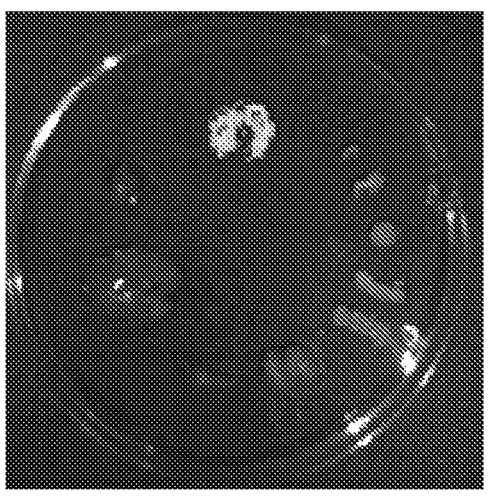

FIG. 17A shows a fluorescence image of lungs harvested from mice in the orthotopic LLC model after treatment with dye-labeled NP-cGAMP.

Figure 17B:
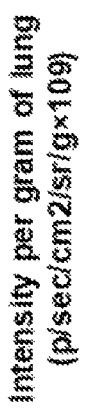
Figure 17B:
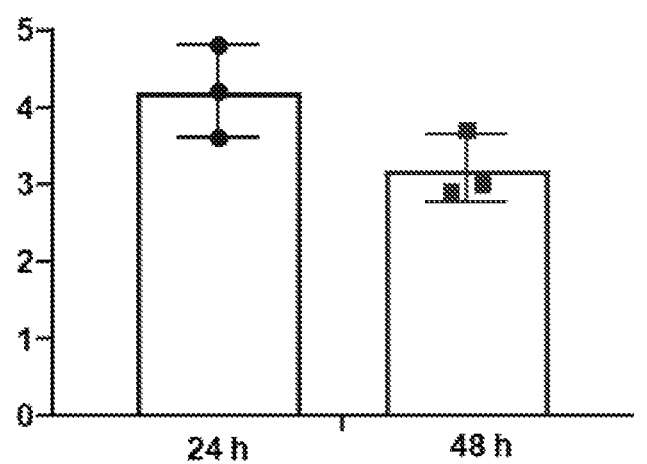

FIG. 17B shows the quantitation of NP-cGAMP in mouse lung tissue by IVIS imaging.

Figures 17C, 17D:
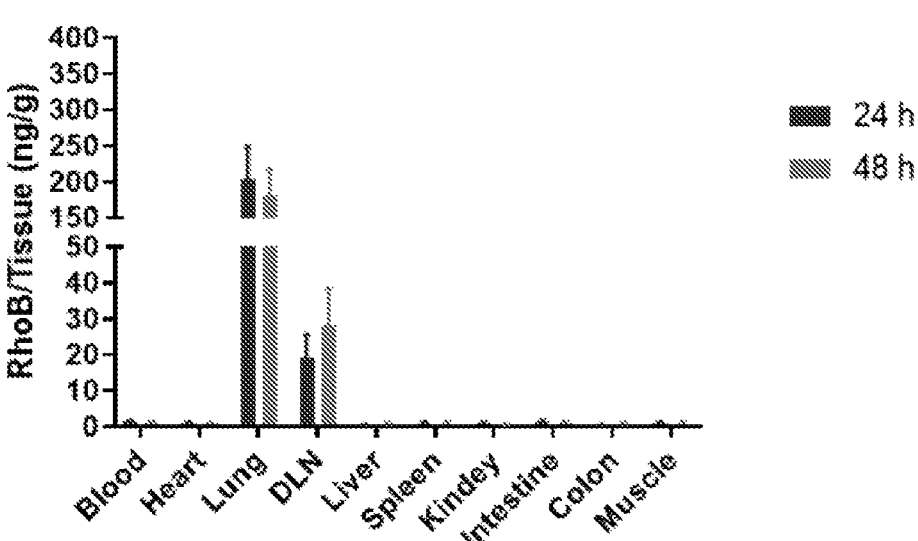

FIG. 17C shows the biodistribution of NP-cGAMP as assessed by HPLC.

FIG. 17D shows the co-localization of inhaled NP-cGAMP with intratumoral antigen presenting cells (APCs) by fluorescence microscopy.

Figure 18:
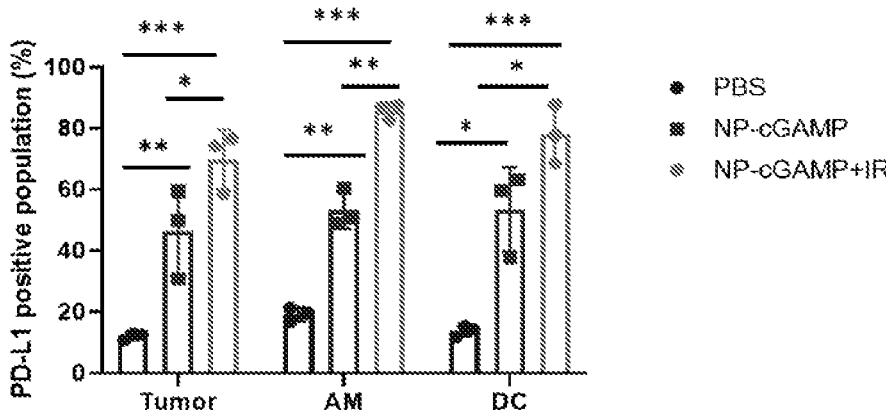

FIG. 18 shows the expression of PD-L1 in tumor cells, alveolar macrophages (AM), and dendritic cells (DC), as assessed by flow cytometry, in mice having LLC lung cancer following treatment with NP-cGAMP with and without irradiation (IR).

Figure 19A:
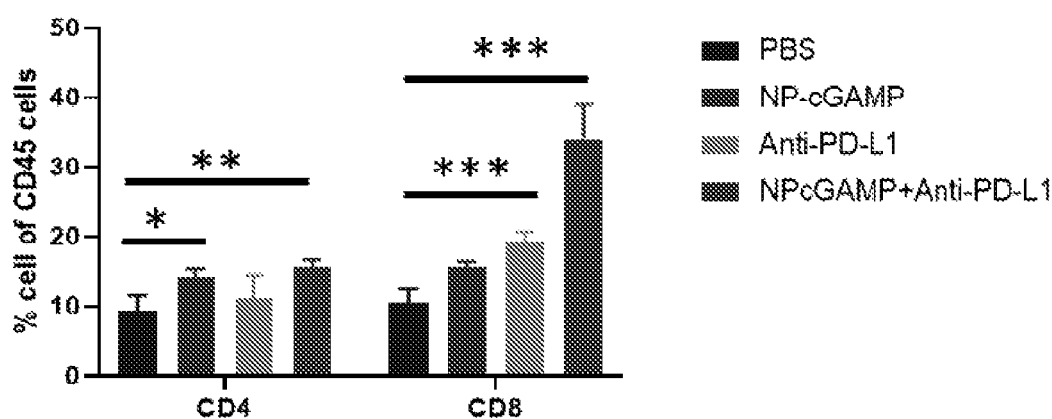

FIG. 19A shows the quantitation of tumor-infiltrating T cells in mice having LLC lung cancer, treated with NP-cGAMP and/or anti-PD-L1.

Figure 19B:
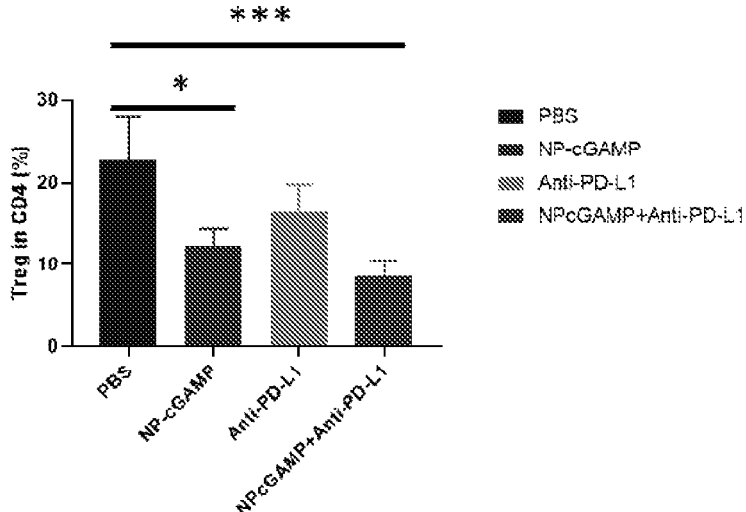

FIG. 19B shows the quantitation of Tregs in lung tumors of mice having LLC lung cancer, treated with NP-cGAMP and/or anti-PD-L1.

Figure 19C:
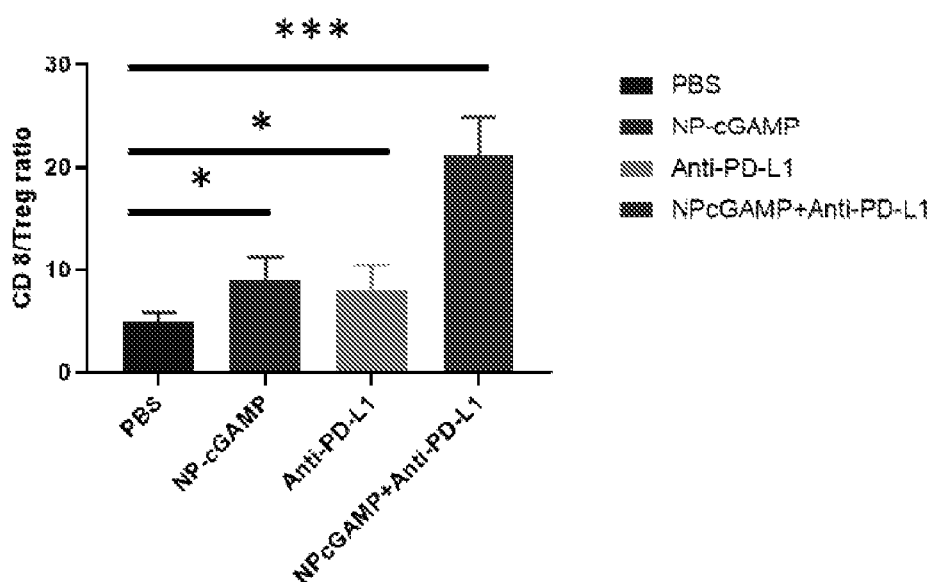

FIG. 19C shows the ratio of CD8$^+$ T/Tregs in lung tumors of mice having LLC lung cancer, treated with NP-cGAMP and/or anti-PD-L1.

Figure 19D:
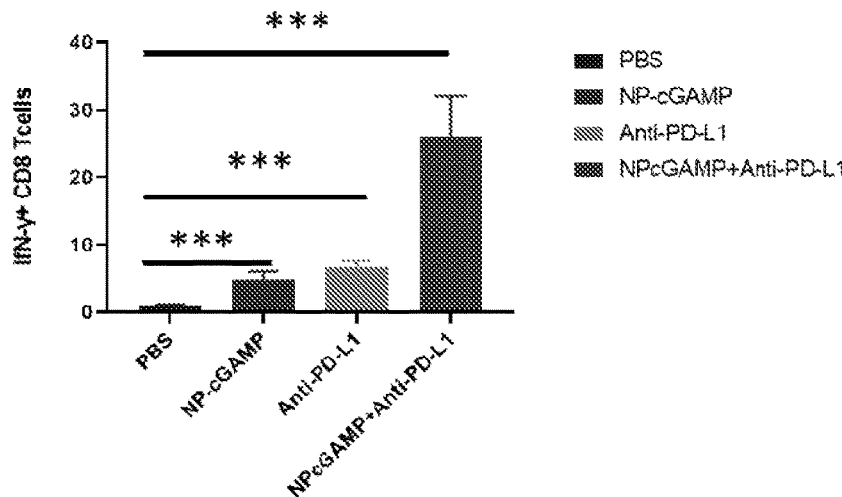

FIG. 19D shows activated CD8$^+$ T cells in lung tumors of mice having LLC lung cancer, treated with NP-cGAMP and/or anti-PD-L1, as determined by intracellular IFN-$\gamma$ staining and FACS.

Figure 20:
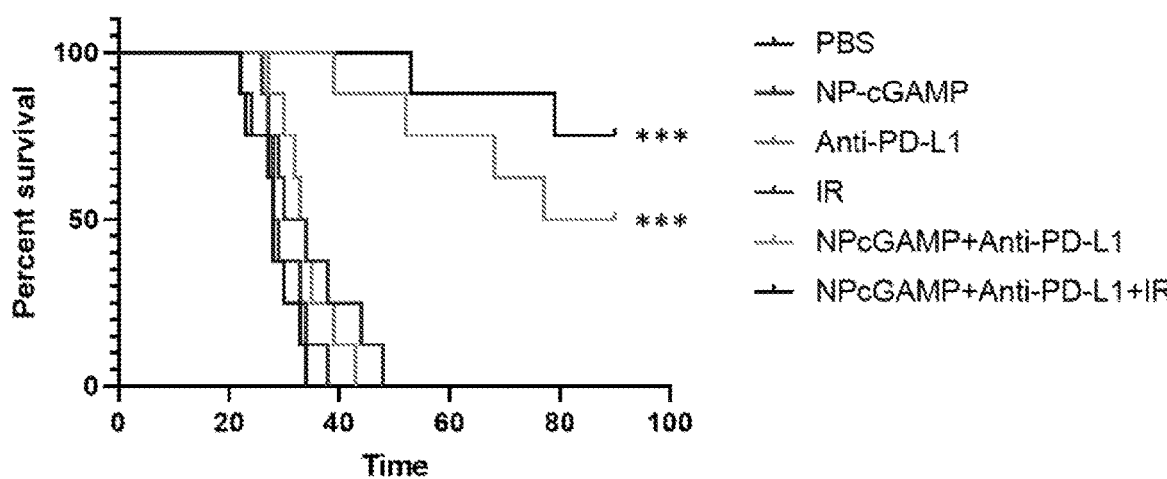

FIG. 20 shows Kaplan-Meier curves for mice having LLC lung cancer and receiving various treatments with or without NP-cGAMP.

DETAILED DESCRIPTION OF THE INVENTION

Provided herein is a new nanotechnological strategy for targeted delivery of immunostimulants to intratumoral APCs. The new nanoparticle-immunotherapy system delivers nanoparticle-loaded nucleic acid therapeutic agents (e.g., nanoparticle-loaded cGAMP; NP-cGAMP) efficiently to target tumors, e.g., in metastases-bearing lungs. When administered via systemic routes, e.g., via inhalation, immunotherapy can be targeted to tumors where intratumoral injection is otherwise not feasible (FIG. 1A). To facilitate APC-targeted delivery, targeting components such as phosphatidylserine (PS) may be employed on the surface of the nanoparticles. Membrane-exposed PS can be recognized and engulfed by macrophages and dendritic cells through their surface PS receptors TIM4 or brain-specific angiogenesis inhibitor 1. Because of localization of STING on ER membranes, it is important to ensure intracellular delivery and subsequent release of these small oligonucleotides to cytosol while bypassing lysosomes. After ingestion by APCs, in response to the low endosomal pH, cGAMP is released from the lipid bilayer-coated calcium phosphate nanoparticles of the invention to cytosol and then binds to STING to initiate the STING pathway. The lipid nanoparticle compositions may also be administered by other routes, e.g., by injection.

Inhaled NP-cGAMP was found to enhance radiotherapy in the lung metastasis mouse models of B16-OVA melanoma and 4T1 breast carcinoma, as described in more detail below. Fractionated radiotherapy (8 Gyx3) delivered to a lung bearing metastases in combination with inhalation of NP-cGAMP synergized to control the metastases not only in the radiotherapy but also in the non-radiotherapy treated lung. Distinct from the intratumoral injection to a single tumor site, inhalation enabled NP-cGAMP can be used for delivery to lesions in both lungs. In addition to enhancing APC maturation, innate immune sensing of immunogenic radiotherapy, and cross-presentation of tumor associated antigens (TAA) to prime effector T cells at the irradiated tumor sites, the inhaled NP-cGAMP promoted pro-inflammatory response in the non-irradiated tumors and facilitated recruitment of TAA-specific effector CD8$^+$ T cells to the tumor sites, which may contribute significantly to the abscopal effect observed in the non-irradiated tumors (FIG. 1A). These data demonstrate the utility of pulmonary administration of NP-cGAMP for targeted delivery of immunomodulators to enhance APC-mediated adaptive immune response against lung cancer.

I. LIPID NANOPARTICLE COMPOSITIONS

A growing body of evidence suggests that the tumor microenvironment is profoundly immunosuppressive. The ability to deliver immunostimulants to the tumor site to mitigate local immune tolerance is crucial for inducing sustained antitumor immunity while reducing systemic toxicity. Whereas previous studies involved intratumoral injection, the present disclosure provides an inhalable nanoparticle-immunotherapy system targeting pulmonary antigen presenting cells (APCs), aimed at enhancing immune response against lung cancer. Antigen presenting cells, include, but are not limited to dendritic cells (DCs), monocytes/macrophages, B lymphocytes or other cell type(s) expressing MHC/co-immunostimulatory molecules. A number of targeting components may be employed including, but not limited to, peptides, antibodies, antibody fragments, lipids, and carbohydrates. The targeting component can be selected based on factors such as the nature of particular lipid nanoparticle in the composition, as well as the type of molecular target (e.g., a C type lectin receptor, an integrin, an Fc$\gamma$ receptor, an MHC-II molecule, or an immune stimulating receptor) and the location of the target within a subject. Lipids such as phosphatidylserine, for example, can lead to targeting of antigen presenting cells in lung tissue. Examples of suitable targeting components include, but are not limited to, those described by Goyvaerts and Breckpot (*Journal of Immunology Research*, 2015, Article ID 785634).

In certain embodiments, inhalation of aerosolized, lipid bilayer-coated particles loaded with the STING agonist, cyclic guanosine monophosphate-adenosine monophosphate (NP-cGAMP) provides rapid distribution of NP-cGAMP to both lungs bearing multifocal lung metastases in mouse models; moreover, phosphatidylserine (PS) assembled on the outer layer of the particles facilitates its preferable recognition and ingestion by alveolar macrophage and dendritic cells, and loading of cGAMP complexed with calcium phosphate in NP-cGAMP ensures the cytosolic release of cGAMP to stimulate the STING pathway and type I interferons production in APCs. Inhaled NP-cGAMP can enhance radiotherapy (IR) in lung metastasis mouse models. Fractionated radiotherapy (8 Gyx3) delivered to one tumor-bearing lung in combination with the inhaled NP-cGAMP synergized to control the metastases not only in the irradiated but also in the non-irradiated lung. Mechanistic studies revealed that APC-targeted delivery of NP-cGAMP enhanced innate immune sensing of immunogenic radiotherapy and improved the immunosuppressive tumor microenvironment in both lungs favorably for robust anti-cancer adaptive immunity. The compositions and methods described herein provide a new nanotechnological strategy of targeted in situ immunomodulation to elicit APC-mediated anti-cancer immunity and promote the abscopal effect in non-irradiated lung metastases.

Some embodiments of the present disclosure provide compositions containing lipid nanoparticles including nucleic acid therapeutic agents. In some embodiments, the lipid nanoparticles are calcium phosphate nanoparticles having a lipid coating, wherein the calcium phosphate nanoparticles include the nucleic acid therapeutic agent. In some embodiments, the nucleic acid therapeutic agent is a cyclic dinucleotide. In some embodiments, the lipid coating includes phosphatidylserine.

As used herein, the term "cyclic dinucleotide" refers to refers to a compound than contains two nucleosides covalently bonded to each other via phosphoester linkages between two ribose hydroxyl groups of the first nucleoside and two ribose hydroxyl groups of the second nucleoside. Examples of cyclic dinucleotides useful for incorporation in the compositions of the present disclosure include, but are not limited to, 2'3' cyclic guanosine monophosphate-adenosine monophosphate (2'3'-cGAMP; CAS Registry No. 1441190-66-4); 3'3' cGAMP (CAS Registry No. 849214-04-6), 3'5' cyclic diAMP (cdA; CAS Registry No. 54447-84-6), cyclic diGMP (cdG; CAS Registry No. 61093-23-0), and pharmaceutically acceptable salts thereof. Further examples of cyclic dinucleotides include those described in U.S. Pat. Nos. 9,724,408; 8,367,716; 7,709,458; 7,592,326; WO 2018/118665; WO 2018/172206; and WO 2018/198076; which references are incorporated herein by reference in their entirety. In some embodiments, the cyclic dinucleotide is 2'3' cyclic guanosine monophosphate-adenosine monophosphate (cGAMP).

In some embodiments, the nucleic acid therapeutic agent is an oligonucleotide, such as an oligodeoxyribonucleotide or an oligoribonucleotide containing from about 2 to about 75 nucleotides (e.g., from about 2 nucleotides to about 70 nucleotides, or from about 2-20 nucleotides, or from about 10 nucleotides to about 60 nucleotides, or from about 20-50 nucleotides, or from about 30-40 nucleotides). In some embodiments the nucleic acid therapeutic is a single stranded DNA, a double stranded DNA, or a single stranded RNA, or a double stranded RNA. The length of the DNA and/or the RNA may range, for example, from a few nucleotides to a few hundred nucleotides or a few thousand nucleotides. The nucleic acid therapeutic may be linear or circular (e.g., in plasmid form). Cyclic dinucleotides, oligonucleotides, and polynucleotides may, in certain instances, be bound directly by STING in certain instances so as to upregulate production of cytokines such as type I interferon. The nucleic acid therapeutic agents may also be recognized by factors such as Z-DNA-binding protein 1 (DA1) or Gamma-interferon-inducible protein Ifi-16 (IFI16) which, in turn, may interact with STING to regulate interferon production as described, for example, by Keating et al. (*Trends in Immunology*, 2011, 32 (12), P574-581).

As used herein, the term "lipid" refers to lipid molecules that can include fats, waxes, steroids, cholesterol, fat-soluble vitamins, monoglycerides, diglycerides, phospholipids, sphingolipids, glycolipids, cationic or anionic lipids, derivatized lipids, and the like. Lipids can form micelles, monolayers, and bilayer membranes. In general, the combination of lipids and nucleic acids in the compositions of the present disclosure are not naturally occurring; the nanoparticles are generally not naturally present, for example, as vesicle-encapsulated nucleic acids in a human subject or other organism. The lipids can self-assemble into monolayer nanoparticle coatings, bilayer nanoparticle coatings, and multilayer nanoparticle coatings. As used herein, the term "liposome" encompasses any compartment enclosed by a lipid bilayer. The term liposome includes unilamellar vesicles which are comprised of a single lipid bilayer and generally have a diameter in the range of about 20 to about 400 nm. Liposomes can also be multilamellar, which generally have a diameter in the range of 1 to 10 μm. In some embodiments, liposomes can include multilamellar vesicles (MLVs; from about 1 μm to about 10 μm in size), large unilamellar vesicles (LUVs; from a few hundred nanometers to about 10 μm in size), and small unilamellar vesicles (SUVs; from about 20 nm to about 200 nm in size). Lipid nanoparticles in the compositions of the present disclosure may also be present as non-lamellar lipid micelles.

In some embodiments, the ratio of the total lipids to the nucleic acid therapeutic agent (e.g., a cyclic dinucleotide such as e.g., 2'3' cGAMP) ranges from about 10:1 to about 1000:1 by weight. The ratio of the total lipids to cyclic dinucleotide or other nucleic acid therapeutic agent can range, for example, from about 10:1 to about 100:1, or from about 10:1 to about 75:1, or from about 15:1 to about 50:1, or from about 20:1 to about 40:1. In some embodiments, the ratio of the total lipids to cyclic dinucleotide or other nucleic acid therapeutic agent ranges from about 30:1 to about 35:1. In some embodiments, the ratio of the total lipids to 2'3' cGAMP ranges from about 20:1 to about 40:1 by weight (e.g., from about 30:1 to about 35:1).

In some embodiments, the ratio of the calcium phosphate in a lipid-coated calcium phosphate nanoparticle to the cyclic dinucleotide in the nanoparticles ranges from about 2:1 to about 50:1 by weight. The ratio of calcium phosphate to cyclic dinucleotide (e.g., 2'3' cGAMP) can range, for example, from about 20:1 to about 30:1, or from about 15:1 to about 35:1, or from about 10:1 to about 40:1, or from about 5:1 to about 45:1. The calcium phosphate may be present, for example, as $Ca(H_2PO_4)_2$, $CaHPO_4$, $Ca_3(PO_4)_2$, $Ca_8H_2(PO_4)_6$, hydrates thereof, and/or combinations thereof.

In certain embodiments, the lipid nanoparticles of the present invention contain at least one phosphatidylserine (PS). The term "phosphatidylserine" refers to a diacylglyceride phospholipid having a serine headgroup (i.e., a 1,2-diacyl-sn-glycero-3-phosphoserine). The acyl groups in a phosphatidylserine lipid are generally derived from fatty acids having from 6 to 24 carbon atoms. Phosphatidylserines can include synthetic and naturally-derived 1,2-diacyl-sn-glycero-3-phosphoserines. Phosphatidylserines and other lipids may be obtained from commercial sources as isolated lipids or lipid extracts, such as a brain extract, soy extract, or the like. Phosphatidylserines are generally present in their negatively-charged, anionic form under aqueous physiological conditions.

Examples of saturated PSs include 1,2-dilauroyl-sn-glycero-3-phosphoserine (DLPS), 1,2-dimyristoyl-sn-glycero-3-phosphoserine (dimyristoylphosphatidylserine; DMPS), 1,2-distearoyl-sn-glycero-3-phosphoserine (distearoylphosphatidylserine; DSPS), 1,2-dipalmitoyl-sn-glycero-3-phosphoserine (dipalmitoylphosphatidylserine; DPPS), 1-myristoyl-2-palmitoyl-sn-glycero-3-phosphoserine (MPPC), 1-palmitoyl-2-myristoyl-sn-glycero-3-phosphoserine (PMPS), 1-myristoyl-2-stearoyl-sn-glycero-3-phosphoserine (MSPS), 1-palmitoyl-2-stearoyl-sn-glycero-3-phosphoserine (PSPS), 1-stearoyl-2-palmitoyl-sn-glycero-3-phosphoserine (SPPS), and 1-stearoyl-2-myristoyl-sn-glycero-3-phosphoserine (SMPS).

Examples of unsaturated PCs include, but are not limited to, 1,2-dimyristoleoyl-sn-glycero-3-phosphoserine, 1,2-dimyristelaidoyl-sn-glycero-3-phosphoserine, 1,2-dipamitoleoyl-sn-glycero-3-phosphoserine, 1,2-dipalmitelaidoyl-sn-glycero-3-phosphoserine, 1,2-dioleoyl-sn-glycero-3-phosphoserine, 1,2-dielaidoyl-sn-glycero-3-phosphoserine, 1,2-dipetroselenoyl-sn-glycero-3-phosphoserine, 1,2-dilinoleoyl-sn-glycero-3-phosphoserine, 1-palmitoyl-2-oleoyl-sn-glycero-3-phosphoserine (palmitoyloleoylphosphatidylserine; POPS), 1-palmitoyl-2-linoleoyl-sn-glycero-3- phosphoserine, 1-stearoyl-2-oleoyl-sn-glycero-3-phosphoserine (SOPS), 1-stearoyl-2-linoleoyl-sn-glycero-3-phosphoserine, 1-oleoyl-2-myristoyl-sn-glycero-3-phosphoserine (OMPS), 1-oleoyl-2-palmitoyl-sn-glycero-3-phosphoserine (OPPS), 1-oleoyl-2-stearoyl-sn-glycero-3-phosphoserine (OSPS), 1,2-diarachidonoyl-sn-glycero-3-phospho-L-serine (20:4PS), and 1,2-didocosahexaenoyl-sn-glycero-3-phospho-L-serine (22:6PS).

In some embodiments, the phosphatidylserine comprises a stearoyl (18:0) moiety, an oleoyl (18:1) moiety, an eicosatetraenoyl (20:4) moiety, a docosahexaenoyl (22:06) moiety, or a combination thereof. In some embodiments, the PS is L-α-phosphatidylserine (brain, porcine; CAS. Registry No. 383907-32-2). Any suitable amount of phosphatidylserine can be used in the lipid nanoparticles. In some embodiments, the amount of phosphatidylserine ranges from about 10 mol % to about 80 mol % based on the total amount of lipids in the lipid nanoparticle (e.g., in the lipid coating of a calcium phosphate nanoparticle, or in a liposome or micelle). The amount of phosphatidylserine can range, for example, from about 20 mol % to about 80 mol %, or from about 25 mol % to about 75 mol %, or from about 30 mol % to about 70 mol %, or from about 35 mol % to about 65 mol %, or from about 40 mol % to about 60 mol %, or from about 45 mol % to about 55 mol % based on the total amount of lipids in the lipid coating, liposome, or micelle. In some embodiments, the amount of phosphatidylserine (e.g., brain phosphatidylserine) ranges from about 45 mol % to about 55 mol % (e.g., about 50 mol %) based on the total amount of lipids in the lipid coating, liposome, or micelle.

The terms "molar percentage" and "mol %" refer to the number of a moles of a given lipid component in a lipid coating or other lipid mixture, divided by the total number of moles of all lipid components. Unless explicitly stated, the amounts of active agents, phosphates, or other components are not included when calculating the mol % for a lipid component in a nanoparticle composition. The terms "about" and "around" indicate a close range around a numerical value when used to modify that specific value. If "X" were the value, for example, "about X" or "around X" would indicate a value from 0.9X to 1.1X, e.g., a value from 0.95X to 1.05X, or a value from 0.98X to 1.02X, or a value from 0.99X to 1.01X. Any reference to "about X" or "around X" specifically indicates at least the values X, 0.9X, 0.91X, 0.92X, 0.93X, 0.94X, 0.95X, 0.96X, 0.97X, 0.98X, 0.99X, 1.01X, 1.02X, 1.03X, 1.04X, 1.05X, 1.06X, 1.07X, 1.08X, 1.09X, and 1.1X, and values within this range.

Other suitable phospholipids include phosphatidylcholines (PCs), phosphatidic acids (PAs), phosphatidylethanolamines (PEs), phosphatidylglycerols (PGs), and phosphatidylinositol (PIs). Examples of phosphatidylcholines which may be utilized in the lipid coatings, liposomes, and micelles include, but are not limited to, egg PC, soy PC, hydrogenated soy PC (HSPC), 1,2-dilauroyl-sn-glycero-3-phosphocholine (DLPC), 1,2-dimyristoyl-sn-glycero-3-phosphocholine (dimyristoylphosphatidylcholine; DMPC), 1,2-distearoyl-sn-glycero-3-phosphocholine (distearoylphosphatidylcholine; DSPC), 1,2-dipalmitoyl-sn-glycero-3-phosphocholine (dipalmitoylphosphatidylcholine; DPPC), 1-myristoyl-2-palmitoyl-sn-glycero-3-phosphocholine (MPPC), 1-palmitoyl-2-myristoyl-sn-glycero-3-phosphocholine (PMPC), 1-myristoyl-2-stearoyl-sn-glycero-3-phosphocholine (MSPC), 1-palmitoyl-2-stearoyl-sn-glycero-3-phosphocholine (PSPC), 1-stearoyl-2-palmitoyl-sn-glycero-3-phosphocholine (SPPC), 1-stearoyl-2-myristoyl-sn-glycero-3-phosphocholine (SMPC), 1,2-dimyristoleoyl-sn-glycero-3-phosphocholine, 1,2- dimyristelaidoyl-sn-glycero-3-phosphocholine, 1,2-dipamiltoleoyl-sn-glycero-3-phosphocholine, 1,2-dipalmitelaidoyl-sn-glycero-3-phosphocholine, 1,2-dioleoyl-sn-glycero-3-phosphocholine (DOPC), 1,2-dielaidoyl-sn-glycero-3-phosphocholine, 1,2-dipetroselenoyl-sn-glycero-3-phosphocholine, 1,2-dilinoleoyl-sn-glycero-3-phosphocholine, 1-palmitoyl-2-oleoyl-sn-glycero-3-phosphocholine (palmitoyloleoylphosphatidylcholine; POPC), 1-palmitoyl-2-linoleoyl-sn-glycero-3-phosphocholine, 1-stearoyl-2-oleoyl-sn-glycero-3-phosphocholine (SOPC), 1-stearoyl-2-linoleoyl-sn-glycero-3-phosphocholine, 1-oleoyl-2-myristoyl-sn-glycero-3-phosphocholine (OMPC), 1-oleoyl-2-palmitoyl-sn-glycero-3-phosphocholine (OPPC), and 1-oleoyl-2-stearoyl-sn-glycero-3-phosphocholine (OSPC).

In some embodiments, the lipid coating, liposome, or micelle contains at least one phosphatidylcholine such as DSPC, DPPC, DMPC, or the like. Any suitable amount of phosphatidylcholine can be used in the lipid coatings, liposomes, and micelles. In some embodiments, the amount of phosphatidylserine ranges from about 1 mol % to about 70 mol % based on the total amount of lipids in the lipid coatings, liposomes, and micelles. The amount of phosphatidylserine can range, for example, from about 10 mol % to about 70 mol %, or from about 15 mol % to about 65 mol %, or from about 20 mol % to about 60 mol %, or from about 25 mol % to about 55 mol %, or from about 30 mol % to about 50 mol %, or from about 35 mol % to about 45 mol % based on the total amount of lipids in the lipid coatings, liposomes, and micelles. In some embodiments, the amount of phosphatidylcholine (e.g., distearoylphosphatidylcholine) ranges from about 35 mol % to about 45 mol % (e.g., about 40 mol %) based on the total amount of lipids in the lipid coatings, liposomes, and micelles.

Other phospholipids that can be included in the lipid coatings, liposomes, and micelles include, but are not limited to, dimyristoylphosphatidylglycerol (DMPG), distearoylphosphatidylglycerol (DSPG), dioleoylphosphatidylglycerol (DOPG), dipalmitoylphosphatidylglycerol (DPPG), dioleoylphosphatidylethanolamine (DOPE), palmitoyloleoylphosphatidylethanolamine (POPE), dipalmitoylphosphatidylethanolamine (DPPE), dimyristoylphosphoethanolamine (DMPE), distearoylphosphatidylethanolamine (DSPE), 16-O-monomethyl PE, 16-O-dimethyl PE, 18-1-trans PE, 1-stearoyl-2-oleoyl-phosphatidyethanolamine (SOPE), dielaidoylphosphoethanolamine (transDOPE), and cardiolipin.

The lipid coatings, liposomes, and micelles can contain steroids, characterized by the presence of a fused, tetracyclic gonane ring system. Examples of steroids include, but are not limited to, cholic acid, progesterone, cortisone, aldosterone, testosterone, dehydroepiandrosterone, and sterols such as estradiol and cholesterol. Synthetic steroids and derivatives thereof are also contemplated for use in the lipid coatings, liposomes, and micelles. In some embodiments, the lipid coating, liposome, or micelle contains at least one sterol such as cholesterol (i.e., 2,15-dimethyl-14-(1,5-dimethylhexyl)tetracyclo-[8.7.0.0$^{2,7}$0.0$^{11,15}$]heptacos-7-en-5-ol). Any suitable amount of sterol can be used in the lipid coatings, liposomes, and micelles. In some embodiments, the amount of sterol ranges from about 1 mol % to about 25 mol % based on the total amount of lipids in the lipid coating, liposome, or micelle. The amount of sterol can range, for example, from about 1 mol % to about 20 mol %, or from about 2 mol % to about 18 mol %, or from about 4 mol % to about 16 mol %, or from about 6 mol % to about 14 mol %, or from about 8 mol % to about 12 mol % based on the total amount of lipids in the lipid coating, liposome, or micelle. In some embodiments, the amount of sterol (e.g., cholesterol) ranges from about 5 mol % to about 15 mol % (e.g., about 5, 6, 7, 8, 9, 10, 11, 12, 13, 14, or 15 mol %) based on the total amount of lipids in the lipid coating, liposome, or micelle.

In some embodiments, the lipid coating, liposome, or micelle further comprises a poly(ethylene glycol)-lipid derivative (PEG-lipid). PEG-lipids can be useful for preventing nanoparticles from sticking to each other or to cells (e.g., blood cells) or tissues (e.g., vascular walls) following administration. PEG-lipids can also increase tumor residence time and/or blood circulation time of the nanoparticles within a subject. In some embodiments, the PEG-lipid is selected from a diacyl-phosphatidylethanolamine-N-[methoxy(polyethylene glycol)], an N-acyl-sphingosine-1-{succinyl[methoxy(polyethylene glycol)]}, and mixtures thereof. The molecular weight of the poly(ethylene glycol) in the PEG-lipid is generally in the range of from about 500 Da to about 5000 Da. The poly(ethylene glycol) can have a molecular weight of, for example, 750 Da, 1000 Da, 2000 Da, or 5000 Da. In some embodiments, the PEG-lipid is selected from distearoyl-phosphatidylethanolamine-N-[methoxy(polyethylene glycol)-2000] (DSPE-PEG-2000) and distearoyl-phosphatidylethanolamine-N-[methoxy(polyethylene glycol)-5000] (DSPE-PEG-5000). In some embodiments, the PEG-lipid is DSPE-PEG-2000.

The lipid coatings, liposomes, and micelles can also include cationic lipids. Cationic lipids contain positively charged functional groups under physiological conditions. Cationic lipids include, but are not limited to, N,N-dioleyl-N,N-dimethylammonium chloride (DODAC), N,N-distearyl-N,N-dimethylammonium bromide (DDAB), N-(1-(2,3-dioleoyloxy)propyl)-N,N,N-trimethylammonium chloride (DOTAP), N-(1-(2,3-dioleyloxy)propyl)-N,N,N-trimethyl-ammonium chloride (DOTMA), N-[1-(2,3-ditetradecyloxy)propyl]-N,N-dimethyl-N-hydroxyethylammonium bromide (DMRIE), N-[1-(2,3,dioleyloxy)propyl]-N,N-dimethyl-N-hydroxy ethylammonium bromide (DORIE), 3β-[N—(N,N-dimethylaminoethane) carbamoyl]cholesterol (DC-Chol), dimethyldioctadecylammonium (DDAB) and N,N-dimethyl-2,3-dioleyloxy)propylamine (DODMA).

In some embodiments, the lipid coating, liposome, or micelle comprises a phosphatidylserine, a phosphatidylcholine, a sterol, or a combination thereof. In some embodiments, the lipid coating, liposome, or micelle contains brain phosphatidylserine in an amount ranging from about 40 mol % to about 60 mol %, DPPC in amount ranging from about 30 mol % to about 50 mol %, and cholesterol in an amount ranging from about 5 mol % to about 15 mol % based on the total amount of lipids in the lipid coating, liposome, or micelle.

In some embodiments, the particles are anionic (having a net negative surface charge) which can provide beneficial intratumoral distribution and minimization of non-specific uptake by cell types other than APCs, an advantage as compared to cationic particles.

Lipid nanoparticles according to the present disclosure generally exhibit diameters well below 1 μm (e.g., less than 750 nm, or less than 500 nm). In some embodiments, the average size of the lipid-coated calcium phosphate nanoparticles in the composition, inclusive of the lipid coating, ranges from about 50 nm to about 200 nm in diameter. The average diameter of the lipid-coated calcium phosphate nanoparticles in the composition may range, for example, from about 50 nm to about 195 nm, or from about 50 nm to about 190 nm, or from about 50 nm to about 185 nm, or from about 55 nm to about 180 nm, or from about 60 nm to about 175 nm, or from about 65 nm to about 170 nm, or from about 70 nm to about 165 nm, or from about 75 nm to about 160 nm, or from about 80 nm to about 155 nm, or from about 85 nm to about 150 nm, or from about 90 nm to about 145 nm, or from about 95 nm to about 140 nm, or from about 100 nm to about 135 nm, or from about 105 nm to about 130 nm, or from about 110 nm to about 125 nm, or from about 115 nm to about 120 nm. In some embodiments, the average size of the lipid-coated calcium phosphate nanoparticles in the composition, inclusive of the lipid coating, ranges from about 50 nm to about 150 nm in diameter.

In some embodiments, the average diameter of the liposomes or micelles in the compositions is less than 750 nm or less than 500 nm. In some embodiments, the average size of the liposome or micelle ranges from about 50 nm to about 200 nm in diameter. The average diameter of the liposome or micelle may range, for example, from about 50 nm to about 195 nm, or from about 50 nm to about 190 nm, or from about 50 nm to about 185 nm, or from about 55 nm to about 180 nm, or from about 60 nm to about 175 nm, or from about 65 nm to about 170 nm, or from about 70 nm to about 165 nm, or from about 75 nm to about 160 nm, or from about 80 nm to about 155 nm, or from about 85 nm to about 150 nm, or from about 90 nm to about 145 nm, or from about 95 nm to about 140 nm, or from about 100 nm to about 135 nm, or from about 105 nm to about 130 nm, or from about 110 nm to about 125 nm, or from about 115 nm to about 120 nm. In some embodiments, the average size of the liposome or micelle ranges from about 50 nm to about 150 nm in diameter.

Lipid nanoparticles may be prepared as described in the examples below or via other methods. Preparation of the lipid nanoparticles may include preparation of lipid solutions or films, hydration of lipids or lipid films, extrusion and/or sonication of lipid mixtures (e.g., aqueous lipid suspensions), in the presence or absence of additional components such as calcium phosphate. Average particle size and polydispersity in a population of nanoparticles can be determined by a number of techniques including dynamic light scattering (DLS), quasi-elastic light scattering (QELS), and electron microscopy. The term "polydispersity index" refers to the size distribution of a population of nanoparticles. Polydispersity index can be determined by a number of techniques including dynamic light scattering (DLS), quasi-elastic light scattering (QELS), and electron microscopy. Polydispersity index (PDI) is usually calculated as:

$$PDI = \left(\frac{\sigma}{d}\right)^2$$

i.e., the square of (standard deviation/mean diameter). Populations of nanoparticles as described herein typically have low polydispersities, generally having a polydispersity index that is less than 0.3, less than 0.2, less than 0.15, or less than 0.10, as measured by DLS. In some embodiments, a population of nanoparticles will have a polydispersity index that is less than 0.2.

II. FORMULATIONS AND DELIVERY OF LIPID NANOPARTICLE COMPOSITIONS

Pharmaceutical compositions according to the present disclosure include, but are not limited to, those suitable for pulmonary, nasal, parenteral, or oral administration. The most suitable route of administration in any given case will depend in part on the nature and severity of the condition being treated. Compositions for parenteral administration may be formulated for intravenous, intratumoral, intramuscular, intra-arteriole, intradermal, subcutaneous, intraperitoneal, intraventricular, and/or intracranial injection.

In some embodiments, the composition is formulated for administration to the lungs of a subject via inhalation. In some embodiments, lipid nanoparticles are administered via inhalation using a nebulizer or like device. The nebulizer may be, for example, an ultrasonic nebulizer, which utilizes ultrasonic vibration waves to atomize or vaporize a liquid formulation containing the nanoparticles, thereby forming an aerosol which can be easily inhaled. Alternatively, the nebulizer may be a compressor nebulizer having a nebulizer cup or like vessel for holding a liquid formulation containing the nanoparticles, and an air compressor for providing compressed air to the nebulizer cup through an aerosol tubing to form an aerosol for inhalation via a mouthpiece or mask. Nebulizers for use in administration of the lipid-coated nanoparticles of the present disclosure include, but are not limited to, those described in U.S. Pat. Nos. 10,029, 055; 9,757,528; 7,624,968; and 6,962,151; which are incorporated herein by reference in their entirety.

Compositions containing lipid nanoparticles of the present disclosure may be formulated with a pharmacologically suitable fluid. Pharmacologically suitable fluids include, but are not limited to, water, buffered aqueous solutions, alcohols (e.g., ethanol, isopropanol, or the like), glycols (e.g., propylene glycol, glycerol, or the like), and mixtures thereof. Aqueous compositions will typically have a pH ranging from about 2.0 to about 8.0 (e.g., pH 4.0-8.0, or pH 5.0-8.0, or pH 6.5-7.5). Suitable buffers include, but are not limited to, potassium phosphate, sodium phosphate, phosphate-buffered saline, sodium citrate, sodium acetate, sodium borate, 2-(N-morpholino)ethanesulfonic acid (MES), 2-[4-(2-hydroxyethyl)piperazin-1-yl]ethanesulfonic acid (HEPES), 3-morpholinopropane-1-sulfonic acid (MOPS), 2-amino-2-hydroxymethyl-propane-1,3-diol (TRIS), and the like. Compositions may further contain salts (e.g., NaCl, KCl, $CaCl_2$, and salts of $Mn^{2+}$ and $Mg^{2+}$) or detergents/surfactants (e.g., a non-ionic surfactant such as N,N-bis[3-(D-gluconamido)propyl]cholamide, polyoxyethylene (20) cetyl ether, dimethyldecylphosphine oxide, branched octylphenoxy poly(ethyleneoxy)ethanol, a polyoxyethylene-polyoxypropylene block copolymer, t-octylphenoxypolyethoxyethanol, polyoxyethylene (20) sorbitan monooleate, and the like; an anionic surfactant such as sodium cholate, N-lauroylsarcosine, sodium dodecyl sulfate, and the like; or a cationic surfactant such as hexdecyltrimethyl ammonium bromide, trimethyl(tetradecyl) ammonium bromide, and the like; or a zwitterionic surfactant such as an amidosulfobetaine, 3-[(3-cholamidopropyl)dimethyl-ammonio]-1-propanesulfonate, and the like). Buffers, salts, and detergents/surfactants are generally used at concentrations ranging from about 1 μM to about 250 mM. For example, the concentration of a buffer, a salt, or a detergent/surfactant may be about 1 μM, or about 10 μM, or about 100 μM, or about 1 mM, or about 10 mM, or about 25 mM, or about 50 mM, or about 100 mM, or about 250 mM. The concentration may be lower or higher, depending on factors such as the lipid components in the composition, the route of administration, or the type of drug delivery device employed if applicable (e.g., the type of nebulizer employed for administration via inhalation).

The compositions provided herein also may include additional excipients and additives. Examples of excipients and additives include, but are not limited to, stabilizers, complexing agents, antioxidants, preservatives which prolong the duration of use or storage of the finished pharmaceutical formulation, flavorings, vitamins, or other additives known in the art. Complexing agents include, but are not limited to, ethylenediaminetetraacetic acid (EDTA) or a salt thereof, such as the disodium salt, citric acid, nitrilotriacetic acid and the salts thereof. Preservatives include, but are not limited to, those that protect the solution from contamination with pathogenic particles, including benzalkonium chloride or benzoic acid, or benzoates such as sodium benzoate. Antioxidants include, but are not limited to, vitamins, provitamins, ascorbic acid, vitamin E, or salts or esters thereof.

III. METHODS FOR CANCER TREATMENT

Also provided herein are methods for treating cancers such as lung cancer. The methods include administering to a subject in need thereof a therapeutically effective amount of a composition as described herein, e.g., a composition containing calcium phosphate nanoparticles having a lipid coating, wherein the calcium phosphate nanoparticles include a cyclic dinucleotide. The compositions may be administered via any suitable route including, for example, via pulmonary, nasal, parenteral, or oral administration. In some embodiments, the composition is administered to the subject via inhalation. Lipid nanoparticles such as lipid-coated calcium phosphate nanoparticles can be administered via inhalation using a nebulizer or like device as described above. In some embodiments, the lipid coatings, liposomes, and/or micelles in the composition contain phosphatidylserine.

Any of the compositions and formulations described above can be used in the methods of the present disclosure. In some embodiments, the cyclic dinucleotide is 2'3' cyclic guanosine monophosphate-adenosine monophosphate (2'3' cGAMP). In some embodiments, the ratio of the lipids to cyclic dinucleotide (e.g., 2'3' cGAMP) ranges from about 10:1 to about 1000:1 by weight. In some embodiments, the lipid coating further comprises a phosphatidylcholine, a sterol, or a combination thereof. In some embodiments, the size of the lipid nanoparticle ranges, inclusive of the lipid coating, from about 50 nm to about 150 nm in diameter. In some embodiments, the composition is aerosolized during administration.

As used herein, the terms "treat," "treatment," and "treating" refer to any indicia of success in the treatment or amelioration of an injury, pathology, condition, or symptom (e.g., lung cancer), including any objective or subjective parameter such as abatement; remission; diminishing of symptoms or making the symptom, injury, pathology or condition more tolerable to the patient; reduction in the rate of symptom progression; decreasing the frequency or duration of the symptom or condition; or, in some situations, preventing the onset of the symptom. The treatment or amelioration of symptoms can be based on any objective or subjective parameter, including, e.g., the result of a physical examination.

As used herein, the terms "effective amount" and "therapeutically effective amount" refer to a dose of a compound such as a cyclic dinucleotide that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols.

1-3, 1992); Lloyd, *The Art, Science and Technology of Pharmaceutical Compounding* (1999); Pickar, *Dosage Calculations* (1999); *Goodman & Gilman's The Pharmacological Basis of Therapeutics,* 1 lth Edition, 2006, Brunton, Ed., McGraw-Hill; and *Remington: The Science and Practice of Pharmacy,* 21$^{st}$ Edition, 2005, Hendrickson, Ed., Lippincott, Williams & Wilkins).

In some embodiments, the cancer is a lung cancer, such as a non-small cell lung cancer (NSCLC), which represents over 80% of all lung cancers, or a small cell lung cancer. The lung cancer may also be a mixed-cell cancer. In some embodiments, the non-small cell lung cancer is a squamous cell carcinoma, a large cell carcinoma, or an adenocarcinoma. Adenocarcinoma, in particular, is frequently found in both smokers and non-smokers. In some embodiments, the cancer comprises one or more metastatic tumors. A lung tumor may contain, for example, metastatic cancer cells such as metastatic breast cancer cells, metastatic melanoma cells, or metastatic pancreatic cancer cells. In some embodiments, the cancer may be a colorectal cancer, a kidney cancer, a head and neck cancer, a bone cancer, a testicular cancer, a thyroid cancer, or a soft tissue sarcoma, each of which may have metastasized to the lung. In some embodiments, the cancer is head and neck cancer (e.g., an oral cancer, a pharynx cancer, an oropharynx cancer, a larynx cancer, a cancer of the paranasal sinuses and nasal cavity, or a cancer of the salivary glands). In some embodiments, the cancer is an esophageal cancer (e.g., esophageal squamous-cell carcinoma or esophageal adenocarcinoma. In some embodiments, the particles are used for the treatment of late stage lung cancers, including those which have metastasized to the lymph nodes, different lung regions, or both.

Nanoparticle compositions according to the present disclosure can be administered at any suitable dose in the methods for treating lung cancer. In general, the compositions will be administered in an amount such that the dose of the cyclic dinucleotide or other nucleic acid therapeutic agent ranges from about 0.01 milligrams to about 1000 milligrams per kilogram of a subject's body weight (i.e., about 0.01-1000 mg/kg). The dose of the cyclic dinucleotide or other nucleic acid therapeutic agent can be, for example, about 0.01-750 mg/kg, or about 0.01-500 mg/kg, or about 0.01-250 mg/kg, or about 0.01-100 mg/kg, or about 0.1-50 mg/kg, or about 1-25 mg/kg, or about 5-10 mg/kg. The dose of the cyclic dinucleotide or other nucleic acid therapeutic agent can be about 0.01, 0.05, 0.1, 0.5, 1, 5, 10, 15, 20, 25, 30, 35, 40, 45, 50, 55, 60, 65, 70, 75, 80, 85, 90, 95, or 100 mg/kg.

The dosages can be varied depending upon the requirements of the patient, the severity of the cancer being treated, and the particular formulation being administered. Algorithmic tools based on mathematical modeling of lung deposition, for example, can be in determining dosage for the treatment of lung cancers. The dose administered to a patient should be sufficient to result in a beneficial therapeutic response in the patient. The size of the dose will also be determined by the existence, nature, and extent of any adverse side-effects that accompany the administration of the drug in a particular patient. Determination of the proper dosage for a particular situation is within the skill of the typical practitioner. The total dosage can be divided and administered in portions over a period of time suitable to treat to the disease or condition. Animal studies, such as mouse studies described in this disclosure, may be useful in determining dosing for humans. For example, an average mouse weighs 0.025 kg. Administering 0.025, 0.05, 0.1 and 0.2 mg of 2'3' cGAMP per day using particles of the present disclosure may therefore correspond to a dose range of 1, 2, 4, and 8 mg of 2'3' cGAMP/kg/day. If an average human adult is assumed to have a weight of 70 kg, the corresponding human dosage would be 70, 140, 280, and 560 mg of 2'3'cGAMP per day. Dosages for other active agents may be determined in similar fashion.

Compositions of the present disclosure can be administered for periods of time which may vary depending upon the type of cancer (e.g., lung cancer) being treated, its severity, and the overall condition of the subject being treated. Administration can be conducted, for example, hourly, every 2 hours, three hours, four hours, six hours, eight hours, or twice daily including every 12 hours, or any intervening interval thereof. Administration can be conducted once daily, or once every 36 hours or 48 hours, or once every month or several months. Following treatment, a subject can be monitored for changes in his or her condition and for alleviation of the symptoms of the cancer. Dosage may either be increased in the event the subject does not respond significantly to a particular dosage level, or the dosage can be decreased if an alleviation of symptoms is observed, or if the cancer has been improved or cured, or if unacceptable side effects are seen with a particular dosage.

In some embodiments, nanoparticle compositions are administered in conjunction with one or more additional anti-cancer agents. Examples of anti-cancer agents include, but are not limited to, chemotherapeutic agents (e.g., carboplatin, paclitaxel, pemetrexed, or the like), tyrosine kinase inhibitors (e.g., erlotinib, crizotinib, osimertinib, or the like), and immunotherapeutic agents (e.g., pembrolizumab, nivolumab, durvalumab, atezolizumab, or the like).

In some embodiments, nanoparticles according to the present disclosure may be administered with one or more immune checkpoint inhibitors. The term "immune checkpoint" refers to a regulatory pathway that contributes to co-stimulatory or inhibitory control of T-cell activity in an organism. Interaction of "immune checkpoint proteins," including proteins on the surfaces of antigen presenting cells and T-cells, contribute to regulation and maintenance of self-tolerance and the duration and amplitude of physiological immune responses in the organism. See, e.g., D. M. Pardol. *Nature Reviews Cancer* 12, 252-264 (2012). Examples of immune checkpoint proteins include, but are not limited to, A2aR (adenosine A2a receptor); BTLA, B, and T (lymphocyte attenuator); ICOS (inducible T cell co-stimulator); MR (killer cell immunoglobulin-like receptor); LAG3 (lymphocyte activation gene 3); PD1 (programmed cell death protein 1); CTLA-4 (cytotoxic T-lymphocyte-associated antigen 4); and TIM3 (T cell membrane protein 3). The term "immune checkpoint inhibitor" refers to a molecule that totally or partially reduces, inhibits, interferes with, or otherwise modulates the activity of one or more checkpoint proteins. Immune checkpoint inhibitors can, for example, include antibodies or peptide-like compounds derived from antibodies. In some embodiments, the immune checkpoint inhibitor is a PD1 inhibitor or a CTLA-4 inhibitor.

"PD1" refers to programmed cell death protein 1, also known as CD279, expressed by T-cells, B-cells, and monocytes. PD-1 is a type I surface glycoprotein characterized by a V-set immunoglobulin superfamily (IgSF) domain attached to a transmembrane domain and a cytoplasmic domain containing two tyrosine-based signaling motifs. PD1 binds at least two ligands: PD-L1 (expressed by cells including T-cells, B-cells, dendritic cells, macrophages, and mesenchymal stem cells) and PD-L2 (expressed by cells including dendritic cells, macrophages, and mast cells).

"CTLA-4" refers to cytotoxic T-lymphocyte-associated antigen 4, also known as CD152, which is expressed exclusively on T-cells. CTLA-4 includes a single Ig-fold extracellular domain with three CDR-like loops, and binds to ligands CD80 (B7.1) and CD86 (B7.2), among others, that are differentially expressed in antigen presenting cells.

In some embodiments, the immune checkpoint inhibitor is selected from the group consisting of a CTLA-4 antibody, an OX40 antibody, a PD-L1 antibody, a PD1 antibody, and a BY55 antibody. In some embodiments, the protein is a CTLA-4 antibody. In some embodiments, the protein is a PD-L1 antibody, a PD-L2 antibody, or a PD1 antibody. In some embodiments, the immune checkpoint inhibitor is a PD-L1 antibody (e.g., atezolizumab, avelumab, durvalumab, or the like). Immune checkpoint inhibitors can be administered at any suitable dose in the methods. In certain embodiments, an antibody immune checkpoint inhibitor is administered at a dose ranging from about 0.1 milligrams to about 100 milligrams per kilogram of a subject's body weight (i.e., about 0.1-100 mg/kg). The dose of the antibody immune checkpoint inhibitor can be, for example, about 0.1-50 mg/kg, or about 1-10 mg/kg. The dose of the antibody immune checkpoint inhibitor can be about 1, 2, 3, 4, 5, 6, 7, 8, 9, 10, 11, 12, 13, 14, 15, 16, 17, 18, 19, or 20 mg/kg.

In some embodiments, nanoparticle compositions are administered in conjunction with radiotherapy, e.g., external beam radiation; intensity modulated radiation therapy (IMRT); brachytherapy (internal or implant radiation therapy); stereotactic body radiation therapy (SBRT)/stereotactic ablative radiotherapy (SABR); stereotactic radiosurgery (SRS); or a combination of such techniques. Advantageously, compositions according to the present disclosure can promote abscopal effects wherein non-irradiated lung metastases are also seen to decrease in size.

IV. EXAMPLES

Example 1. Preparation and Characterization of Phosphatidylserine (PS)-Coated NP-cGAMP Lipid bilayer-coated nanoparticles containing 2'3'-cGAMP (NP-cGAMP) was prepared in two steps using a water-in-oil reverse microemulsion method. See, Li, et al. *J Control Release* 158, 108-114, (2012); Au, et al. *Biomaterials* 82, 178-193, (2016). DSPC (1,2-distearoyl-sn-glycero-3-phosphocholine, 18:0 PC), cholesterol, brain PS (L-α-phosphatidylserine), DSPA (1,2-distearoyl-sn-glycero-3-phosphate, 18:0 PA), and Rhod-b (18:1 Liss Rhod PE, 1,2-dioleoyl-sn-glycero-3-phosphoethanolamine-N-(lissamine rhodamine B sulfonyl)) were purchased from Avanti Polar Lipids. cGAMP (2'3'-cGAMP, cyclic [G(2',5')pA(3', 5')p]) and cGAMP control (2'S'-GpAp) were purchased from InvivoGen. Both layers in the lipid bilayer coating contain anionic PS. Briefly, 150 μL of $CaCl_2$ (2.5 M in $ddH_2O$, pH=7.0) was added to 5 mL mixed oil phase 1 (cyclohexane:igepal co-520=80:20) in a 50 mL flask and stirred at 600 rpm for 20 min to form a well-dispersed micro-emulsion phase. Oil phase 2 was prepared by adding 50 μL lipid mixture (20 mM, PS:DSPC:cholesterol=5:4:1) to 5 mL mixed oil phase (cyclohexane:igepal co-520=80:20). A similar micro-emulsion containing sodium phosphate was prepared by adding 150 μL $Na_2HPO_4$ (25 mM in $ddH_2O$, pH=9.0) to 5 mL mixed oil phase 2 with the calcium (Ca):phosphate (P) ratio of 100:1. The CaP core with single layer anionic lipid coating was formed by mixing oil phase 1 and oil phase 2 and stirring at 600 rpm for 20 min. To collect the lipid-coated CaP cores, 10 mL ethanol was added to the mixture and centrifuged at 16,000 g for 15 min, followed by washing with ethanol three times. The collected CaP cores were dispersed in 1 mL chloroform and centrifuged at 2000 g for 5 min to remove CaP precipitates without lipid coatings. The supernatants containing a single layer of lipid-coated CaP were further mixed with 70 μL lipid mixture (20 mM, brain-PS:DSPC:cholesterol=5:4:1, molar ratio, in $CHCl_3$) into 50 mL flask, followed by chloroform evaporation under reduced pressure to form a lipid film. NP—CaP nanoparticles with bilayer lipid coating were formed by adding 1 mL PBS (0.1 M, pH=7.4) and rehydrating under water bath sonication for 5 min and sonic probe at 20 W for another 2 min at 70° C. The resulting nanoparticles were further filtered with 0.45 μM membrane to remove the free lipid aggregates and stored at 4° C. For DSPA-exposed CaP nanoparticles, DSPA at 20 mM was used instead of brain-PS during the preparation. To load cGAMP, half of the desired content cGAMP was mixed with each the CaCl2 solution and Na2HPO4. For fluorescently labeling NPs, 18:1 Liss Rhod PE (Rhod-b) was added to the second lipid mixture with a molar ratio of 1%. DiR was further used for labeling the NPs by adding DiR directly to the second lipid mixture at a molar ratio of 5%.

The size, size distribution, and zeta potential of NP-cGAMP in aqueous solution were measured by a Malvern Zetasizer Nano ZS90. Transmission electron microscopy (TEM) measurements were performed on an FEI Tecnai Bio Twin transmission electron microscope. To determine cGAMP loading efficiency, 0.2 mL of NPs were incubated with 0.2 mL 0.8 M HCl for 24 h to dissolve CaP nanoparticles and release cGAMP. The mixture was further centrifuged at 14000 g for 15 min, and the supernatant was gathered to quantify the cGAMP concentrations by HPLC analyses using an Agilent 1100 HPLC system. The release of cGAMP from nanoparticles was assessed by dialysis of NP-cGAMP solution against release medium at different pH (pH 7.4, 6.5 and 5.0). The release medium was removed for analysis at 0.5, 1, 2, 4, 8, 12, 24, 36, 48 and 72 h. cGAMP content in the release medium was determined by HPLC. The nanoparticles were incubated in PBS (pH 7.4, 0.01 M) with 10% FBS (v/v) at 37° C. for 5 days to study particle stability. The change in particle size was monitored at specific time intervals by Zetasizer.

Both layers of the lipid bilayer nanoparticle coating contain anionic PS. The PS exposed on the outer layer serves as the 'eat me' signal for APCs, while the inner PS interacts with cationic $Ca^{2+}$ of calcium phosphate (CaP) in the core, where CaP is complexed with cGAMP to stabilize the small molecule cGAMP. NP-cGAMP had an average diameter of 118.8±1.4 nm and a negative surface charge of −40.7±0.8 mV (FIG. 1B,C). HPLC analysis indicated high encapsulation efficiency of cGAMP (71.9%) and a high payload of cGAMP (31.6 μg/mg lipid). To study its stability, NP-cGAMP was incubated in 10% FBS at 37° C. DLS measurements showed that the size remained relatively unchanged for up to 120 h (FIG. 1D). Furthermore, to mimic physiological extracellular and acidic endosomal environments, the drug release profiles of NP-cGAMP in PBS at pH 7.4, pH 6.5, or pH 5.0 were determined (FIG. 1E). NP-cGAMP exhibited little cGAMP release at pH 7.4, but an acidic pH-responsive release (~40% at pH 6.5 and ~80% at pH 5.0 at 12 h). These data demonstrate that NP-cGAMP is stable at pH 7.4 but releases cGAMP in a pH-dependent manner.

Example 2. Biochemical Materials and Methods

Cell lines. The OVA-transfected mouse melanoma B16F10 cells (B16-OVA) and parental Bl6F10 cells (ATCC), and the 4T1 breast cancer cells stably transfected with firefly luciferase (4T1-Luc; provided by Dr. David Soto Pantoja, Wake Forest), mouse vascular endothelial cells, bEnd.3 (ATCC) were cultured in Dulbecco's Modified Eagle Medium (DMEM), supplemented with 10% fetal bovine serum (FBS), 100 U/mL penicillin and 100 µg/mL strepto-mycin and maintained in a humidified atmosphere contain-ing 5% $CO_2$ at 37° C.

Induction of bone marrow-derived macrophages (BMDMs), bone marrow-derived dendritic cell (BMDCs) and isolation of alveolar Macrophages (AMs). BMDMs were generated by culturing bone marrow cells flushed from C57BL/6 mouse femurs. Briefly, the gathered bone marrow cells were incubated in completed $\alpha$-MEM containing 10% heat-inactivated FBS and penicillin/streptomycin. 18 h later, the floating cells were collected and cultured in complete BMDM medium (complete $\alpha$-MEM supplemented with 50 ng/mL M-CSF). Three days later, the adherent cells were used as macrophages and phenotyped by determining the expression of CD11b and F4/80 (typically 70-85% CD11b$^+$ F4/80$^+$).

BMDCs were also generated by culturing bone marrow cells flushed from the femurs of C57BL/6 mice in BMDC medium: RPMI-1640 containing 10% heat-inactivated FBS, penicillin/streptomycin, 20 ng/mL GM-CSF, 5 ng/mL IL-4 and 1×2-mercaptoethanol. The culture medium was half-replaced every 2 days, and the non-adherent and loosely adherent immature DCs were collected on day 8 and phe-notyped by determining the expression of CD11c (typically 60-80% CD11b$^+$). To obtain AMs, C57BL/6 mice were sacrificed by $CO_2$. The trachea was then cannulated with a blunt 22-gauge needle and tied in place. Bronchoalveolar lavage (BAL) was flushed with PBS containing 0.5 mM EDTA. Aliquots of 1 mL were instilled into the lungs and aspirated back into the syringe. This procedure was repeated 3 times per mouse. The gathered cells were cultured in DMEM medium with 10% heat-inactivated FBS, 2-Mercap-toethanol (1×), and penicillin/streptomycin.

Cellular uptake of PS-coated nanoparticles in vitro. Briefly, 5,000 BMDM, BMDC, and AM cells were seeded in 24 well plates with poly-lysine coated coverslips for 24 h. Then, the media was replaced with the complete medium containing PS-exposed or DSPA-exposed nanoparticles labeled with DiR and cultured for another 0.5 h. Cells were then washed twice with cold PBS and fixed with 4% formaldehyde for 15 mins. After 1% Triton X-100 treatment for 15 mins, the cells were stained with Alexa Fluor 488 phalloidin (Thermo Fisher) for 30 mins and incubated with 1 µg/mL DAPI for 5 mins. The cellular uptake of nanopar-ticles was observed by fluorescence microscope. To deter-mine whether the PS-coated NPs are preferentially recog-nized and ingested by APCs, we repeated the above experiment with 4T1-luc or B16F10 cancer cells or normal mouse vascular endothelial bEnd.3 cells.

Real time RT-PCR of type I IFN and other inflammatory response genes induced by NP-cGAMP. BMDM, BMDC or AM cells (10$_5$) were seeded into 6-well plates and cultured for 24 h. The cells were then incubated at 37° C. with free cGAMP or NP-cGAMP (100 nM cGAMP) suspended in complete culture medium for 4 h. All cellular RNA was collected using TRIzol reagent (Thermo Fisher). One micro-gram of total RNA was transcribed into cDNA using High-Capacity cDNA Reverse Transcription Kit (Thermo Fisher), and real-time quantitative PCR (qPCR) was performed using PowerUp SYBR Green Master Mix (Thermo Fisher) with primers for amplification of Gapdh, Ifnb1, Cxcl9, Cxcl10, Tnf, Il6, Il12b, Il1b, Ifna1, Il10, and Tgfb1 genes. mRNA levels were normalized against the housekeeping gene GAPDH.

Western blot of STING pathway activation by NP-cGAMP. For western blot analysis, the above APC cells incubated with free cGAMP or NP-cGAMP (100 nM cGAMP) for 8 h were washed and lysed in 50 µL of lysis buffer containing a protease inhibitor cocktail (Roche). The cell lysates with total protein (40 µg) were electrophoresed. Anti-phospho-IRF-3 (1:1000), anti-IRF-3 (1:1000), Anti-phospho-TBK1 (1:1000), and anti-TBK1 (1:1000) were from Cell Signaling Technology. Anti-$\beta$-actin (1:1000) (Santa Cruz Biotechnology) was used as housekeeping protein. Goat anti-mouse or goat anti-rabbit HRP-conju-gated antibodies (1:10000) (Santa Cruz Biotechnology) were used as the secondary antibody. The membranes were visualized using the ECL system (Bio-Rad) and the expres-sion levels of protein were normalized to actin protein expression levels.

Flow cytometry. Flow cytometry was performed on a BD Canto II flow cytometer and analyzed using FlowJo software (BD Biosciences). Doublets and debris of dead cells were excluded before various gating strategies were applied. Gates and quadrants were set based on isotype control staining.

ELISA assay. Cytokines in cell culture medium, blood samples or lung tissues were analyzed with ELISA Max Deluxe Sets from BioLegend by following the manufactur-er's instructions. After adding the HRP substrates, optical densities were determined at a wavelength of 450 nm in an ELISA plate reader (Bio-Rad).

In vitro DC cross-presentation assay. BMDCs were gen-erated as described previously and phenotyped by determin-ing the expression of CD11c. Semi-confluent B16-OVA cells were irradiated with 0 or 20 Gy of a single dose and then immediately seeded into 24-well plate at 10$^5$ cells per well and cultured for 72 h. Wells were washed twice and 2×10$^4$ BMDCs were added and cultured in the presence of NP-cGAMP, free cGAMP or controls at 37° C. for 18 h. OVA$_{257-264}$ presented with MHC-I on the cell surface was detected by anti-H-2Kb bound to SIINFEKL-PE-Cy7, an antibody that specifically recognizes OVA peptide SIIN-FEKL bound to H-2Kb of MHC-I by FACS.

In vitro CD8 T cell priming assay. CD8$^+$ T cells were isolated from spleens of C57BL/6-Tg (TcraTcrb)1100Mjb/J (OT-I) mice (Jackson Laboratory) by magnetic separation (STEMCELL Technologies) according to the manufactur-er's instructions. The purity of CD8$^+$ T cells was >95%. 1×10$_5$ cells CD8$^+$ T cells were added into the mixture of BMDCs with the B16-OVA cells pretreated with/without radiotherapy in the presence of NP-cGAMP or controls, as described above. Eighteen hours later, cell culture superna-tants were collected and measured for IFN-$\gamma$ content as a surrogate of activation of tumor-specific CD8+ T cells, by ELISA assay.

In vivo lung metastasis models. All animal procedures were approved by the Institutional Animal Care and Use Committee at the Wake Forest University School of Medi-cine. For the B16-OVA lung metastasis model, C57BL/6 mice (6-8 weeks, female:male at 1:1; Charles River Labo-ratories, Wilmington, MA) were injected i.v. with 2×10$_5$B16-OVA cells. Five days later, the mice developed multifocal metastases on both lungs. For the 4T1-luc lung metastasis model, 4T1-Luc cells were injected orthotopi-cally into the right fourth mammary fat pad of female BALB/c mice (8-10 weeks; Charles River). When the tumor volume reached ~500 mm$^3$ on Day 14, the primary tumor was surgically removed. Development of lung metastases was confirmed on Day 18 by BLI and MRI. In vivo mechanistic studies and treatment were subsequently conducted on the mice, as described below in details.

Inhalation of aerosolized PS-coated nanoparticles. A clear plastic box with a wire-netting floor was used for inhalation treatment. Aerosol was generated via a medical-grade nebulizer attached by medical tubing to the animal chamber. Three unanaesthetized animals were placed in the sealed chamber at each time and exposed to aerosol at an air flow rate of 7 L/min for 28 minutes, during which ~5 mL of solution loaded in the nebulizer were aerosolized. The mass mean aerodynamic diameter (MMAD) and geometric standard deviation (GSD) of aerosolized particles were measured using a TSI 3321 Aerodynamic Particle Sizer Spectrometer. For in vivo biodistribution study, DiR- or Rhod-b-labeled PS-coated NP—CaP (DiR 660 µg; Rhod-b 700 µg) in 5 mL PBS was loaded into the nebulizer. For treatment, NP-cGAMP (100 µg cGAMP) in 5 mL PBS was loaded into the nebulizer.

In vivo biodistribution and quantification of PS-coated nanoparticles. BALB/c healthy mice and mice with 4T1-Luc lung metastasis were placed in the chamber to inhale DiR-labeled PS-coated NP for 28 mins. The animals were sacrificed at 1 h, 24 h and 48 h (n=3/time) and major organs were dissected and ex vivo imaging was conducted using an IVIS® Lumina system (Caliper Life Sciences). The signal intensity was analyzed using Living Image® 3.1 software. Immediately after ex vivo imaging, the lung tissues were preserved and sectioned for immunofluorescence microscopy. Cryosections (6 µm thick) were co-stained with anti-mouse CD11c⁻ FITC (1:200; BioLegend, N418) and anti-luciferase (1:500; Sigma-Aldrich, L0159) followed by cy3-anti-rabbit secondary antibody (1:800; Jackson Immuno), and observed using a fluorescence microscope. DiR signals were recorded and merged with the CD11c image and the luciferase-stained image of the same field. DiR⁺ cells in lung tissues and DLNs were also determined by FACS To quantify tissue concentrations of PS-coated nanoparticles, the 4T1-Luc lung metastasis mice were sacrificed at 1 h, 24 h and 48 h after inhaling Rhod-b-labeled PS-coated NP (n=3/time). Major organs and blood were collected for HPLC analyses, using a method reported previously. See, Du, et al. *Biomaterials* 69, 1-11, (2015). For Rhod-b detection, HPLC grade acetonitrile and water (90:10, v/v) with 0.1% TFA was used as mobile phase A and HPLC grade tetrahydrofuran (THF) with 0.1% TFA was used as mobile phase B. The mobile phase was delivered at 1.0 mL/min with A:B=7:3 at 30° C. The fluorescence detector was set at 540 nm for excitation and 590 nm for emission, and linked to Chem-Station LC 3D system for data analysis. Linear calibration curves for concentrations in the range of 0.004-100 ng/µL were plotted using the peak areas by linear regression analysis and concentration of Rhod-b in each sample was determined. Based on HPLC measurements of Rhod-b-NPs in lungs, the concentration of cGAMP deposited in lungs 1 h after inhalation was determined.

In vivo VITAL cell killing assay. Spleen cells from naïve C57BL/6 mice were isolated and pulsed with/without OVA$_{257-264}$ for 2 h in complete medium. The non-pulsed and OVA-pulsed cells were then labelled with high (0.5) or low (0.05) carboxyfluorescein succinimidyl ester (CFSE), respectively, in serum-free medium for 15 min. Equal numbers (1×10$_7$) of CFSE$^{high}$ (non-pulsed) and CFSE$^{low}$ (OVA pulsed) cells were mixed and injected intravenously into the B16-OVA mice of different treatment groups (on Day 18 post tumor implant). After 16 h, blood was collected and subjected to flow cytometry analysis. The number of CFSE$^{high}$ and CFSE$^{low}$ cells were determined and used to calculate the percentage of OVA peptide-specific cell killing based on the following equation:

$$\text{Percentage of specific killing} = (1 - \text{non-transferred control ratio/experimental ratio}) \times 100$$

Irradiation. Animals were anesthetized with inhaled 3% isoflurane and positioned with the lung 50 cm below the aperture of an X-RAD 320 orthovoltage irradiator (Precision X-ray). Fractionated irradiation (8 Gy×3 daily fractions) was delivered at a rate of 176 cGy/min through a custom fabricated Lipowitz alloy shield to the right lung. The custom-built half circle-shaped collimator with a radius of 5 mm allowed a large area of the right lung to be irradiated, while minimizing the radiation dose to important mediastinum and tissues outside the right lung.

In vivo treatment of lung metastases. For the B16-OVA lung metastases, after confirming visible multifocal lung lesions on the surface of both lungs by sacrificing randomly selected animals on Day 5, the mice (n=6/group) were randomly grouped and treated as follows: i) PBS (inhalation), ii) NP-CTR (inhalation of NP-2'5'-GpAp), iii) radiotherapy (8 Gy×3 to the right lung), iv) Inhalation of NP-cGAMP, v) NP-cGAMP+radiotherapy, vi) NP-cGAMP+radiotherapy+Clod (inhalation of NP-clodronate), vii) NP-cGAMP+radiotherapy+anti-CD4 and viii) NP-cGAMP+radiotherapy+anti-CD8α. Inhalation of NP-cGAMP or controls occurred 24 h after each radiotherapy for a total of 3 doses. To deplete pulmonary APCs, the mice inhaled NP-clodronate (200 µg) 6 h before each NP-cGAMP for 3 doses. For depleting CD4⁺ or CD8⁺ T cells, 400 µg anti-mouse CD4⁺ antibody (BioXCell, cloneGK1) or anti-mouse CD8α antibody (BioXCell, clone2.43) was injected i.p. one day before treatment and repeated 7 days later. The mice were sacrificed for enumeration of metastatic lung foci on Day 18. Both the left and right lungs were evaluated under a dissecting microscope and quantified separately. For the 4T1-luc model, lung metastases were visualized by BLI and MRI, and confirmed by ex vivo examination 4 days after removal of the primary tumor on Day 14, as described above. The mice (n=8/group) were then randomly grouped and treated as follows: i) PBS, ii) NP-CTR, iii) radiotherapy (8 Gy×3 to the right lung), iv) inhalation of NP-cGAMP, v) NP-cGAMP+radiotherapy, vi) NP-cGAMP+radiotherapy+Clod. Lung metastases burden was monitored longitudinally by BLI and MRI. Survival of the mice was followed for up to 150 days, as described previously.

Bioluminescence imaging of initiation and development of lung metastases of 4T1-luc. Two weeks after orthotopic implantation of 4T1-luc breast cancer, BLI of the chest was initiated and repeated on Day 18, 32 and 39. The mice (n=6/group) were anesthetized with 2% isoflurane inhalation and injected i.p with 150 mg/kg D-luciferin. BLI was acquired 10 mins later using the IVIS Lumina Imaging System (Caliper Life Sciences). Data were quantified with the Living Imaging software by using absolute photon counts (photons/s/cm²/Sr) in an ROI, manually drawn to outline the BLI signal of the chest.

MRI follow-up of lung metastases volume. MRI was conducted on a 7T Bruker BioSpec small animal scanner (Bruker Biospin, Rheinstetten, Germany). The imager of MRI was blinded to the group allocation. Immediately after BLI detection of lung metastases on Day 18, MRI was initiated and followed on Day 32 and Day 39. The mice (n=5/group) were anesthetized with isoflurane (3% induction, 1.5% maintenance). Respiration was monitored with a respiratory bulb under the chest and a SHARPII animal monitoring system was used for respiratory gating. Anatomical T2-weighted imaging was conducted using a RARE sequence with TR/TE=1600/23 ms; ETL: 8; NSA: 8; matrix size: 128×128; and scan time: 3 min 53 s. Individual tumor volumes were measured on T2-W images by manually outlining the enhancing portion of the mass on each image and the total of lung metastases volume for each animal was the sum of individual volumes.

Histology and Immunohistochemistry. H&E staining was performed on cryosections (10 µm) of different tissues including normal heart, lung, liver and spleen, as well as lung metastases-bearing lungs. For immunohistochemical staining of TILS, cryosections (10 µm) of 4T1-luc lung metastases-bearing lung tissues obtained from the above treatment group on Day 22 (24 h after the last inhalation) were immunostained with anti-mouse CD8α(1:500; BioLegend) or anti-mouse FoxP3 antibody (1:500; BioLegend) followed by horseradish peroxidase (HRP)-conjugated goat anti-rat secondary antibody (1:500; Jackson Immuno). The sections were then developed with DAB kits (3,3'-Diaminobenzidine; Vector Laboratories) and counterstained by hematoxylin.

Statistical analysis. Statistical analysis was performed using Microsoft Excel and Prism 7.0 (GraphPad). Data were presented as mean±s.d. Statistical significance was determined by Student's t-test. All t-tests were one-tailed and unpaired, and were considered statistically significant if p<0.05. The survival assay was analyzed using a log-rank test and considered statistically significant if p<0.05.

Example 3. Preferential Uptake of the PS-Coated NP-cGAMP by APCs to Effectively Activate the STING Pathway In Vitro To evaluate the uptake of PS-coated nanoparticles by APCs, the DiR-labeled NP-DiR was incubated with various APCs including alveolar macrophage (AM), bone marrow derived dendritic cells (BMDC) and macrophage (BMDM). After a short incubation of 30 mins, robust uptake of NP-DiR by all 3 types of cells was observed by visualizing intracellular DiR signals (FIG. 2A). By contrast, there was minimal DiR signal in either 4T1-luc breast cancer cells, B16-F10 melanoma cells or mouse vascular endothelial bEnd.3 cells. To exclude the possibility that the specific uptake by APCs was simply due to the anionic lipid coating, we reformulated the lipid bilayer coating by replacing PS with anionic phosphatidic acid (PA) on the outer layer. Incubation with the PA-NP (surface charge −42 mV) showed much less DiR in APCs compared to the PS-NP. Specific binding of PS-NP and subsequent uptake by APCs was investigated and found to be PS-dependent. Data clearly showed that the uptake of PS-NP by APCs was largely abolished if PS-NPs were pretreated with anti-PS antibody to block the surface exposed PS. These data indicate that the PS-coated nanoparticles are preferably recognized and ingested by APCs and that the process is PS-mediated.

To assess whether NP-cGAMP can enhance cytosolic delivery of cGAMP to activate the STING pathway and type I IFN production in APCs, BMDMs, BMDCs, and AMs were incubated with free cGAMP (100 nM) or NP-cGAMP (100 nM cGAMP) for 4 h. Relative expression of type I IFN and other inflammatory response genes were evaluated by real-time PCR. As shown in FIG. 2B, NP-cGAMP induced a drastic increase in expression of Ifnb1 and Ifna1 as well as other proinflammatory genes including Tnf, Il1b, Il6, Il12b and Cxcl9,10, while only a modest increase was observed with free cGAMP (FIG. 2B). This divergence was probably caused by the preferential uptake of PS-coated NP-cGAMP by APCs. Consistent with the PCR results, ELISA measurements detected a significant increase in the corresponding cytokines in the culture medium of APCs treated with NP-cGAMP (FIG. 3). During further investigation as to whether NP-cGAMP can activate the STING pathway, Western blot analysis revealed higher levels of phosphorylated TBK1 and IRF3 in the NP-cGAMP treated cells than free cGAMP treated APCs (FIG. 2C), indicating activation of the STING pathway. These data demonstrate that NP-cGAMP provides more efficient cytosolic delivery of cGAMP than free cGAMP to activate the STING pathway and production of type I IFNs as well as other inflammatory cytokines in APCs.

Example 4. NP-cGAMP Stimulates APC Activation, Cross-Presentation and T Cell Priming In Vitro The APCs that were treated with NP-cGAMP for 8 h were also analyzed by FACS to study expression of MHC class II and CD86, a co-stimulatory molecule. As shown in FIG. 2D, a marked increase (right shift) in both MHC-II and CD86 was observed in the NP-cGAMP treated BMDM, BMDC and AM. These data, together with previous observations of the upregulated proinflammatory cytokines (FIG. 2B and FIG. 3), suggest that NP-cGAMP stimulates the maturation of APCs. To further investigate if NP-cGAMP can enhance APC sensing and cross-presenting of TAA to prime T cells, the well characterized melanoma B16-OVA cells that stably express chicken ovalbumin were chosen as a model antigen and treated with a single dose of 20Gy radiotherapy. Using anti-mouse SIINFEKL-2Kb antibody, a significant increase in antigen presentation on the B16-OVA cells was observed. These B16-OVA cells were then incubated with BMDCs in the presence of free cGAMP or NP-cGAMP for 18 h. FACS analysis showed that NP-cGAMP led to a significant increase in the OVA peptide-MHC-I complex on BMDCs (p<0.05), and even higher expression when BMDCs were incubated with the irradiated B16-OVA cells (p<0.01; FIG. 2E). Lastly, CD8$^+$ T cells from the transgenic mice expressing T cell receptor (TCR) specific for the ovalbumin peptide SIINFEKL (OT1) were isolated and placed into the above mixture of BMDCs and B16-OVA cells. ELISA results showed significantly higher levels of IFN-γ in the culture medium in which the BMDCs were preincubated with the irradiated B16-OVA in the presence of NP-cGAMP (FIG. 2F), indicating activation of tumor antigen-specific CD8$^+$ T cells by NP-cGAMP. These data demonstrate that NP-cGAMP efficiently promotes APC activation and cross presentation of TAA to prime tumor antigen-specific CD8$^+$ T cells.

Example 5. Targeted Delivery of NP-cGAMP to Pulmonary APCs by Inhalation

To provide delivery of NP-cGAMP to deep lungs via inhalation, aerosolized NP-cGAMP was generated with the nebulizer system depicted in FIG. 4. These aerosols had a mass mean aerodynamic diameter of 1.38 µm, which is an advantageous size range for deep lung deposition (Knight, et al. *Cancer Chemother Pharmacol* 44, 177-186, (1999); Mangal, et al. *Acta Pharmacol Sin* 38, 782-797, (2017). After inhaling NP-DiR, the mice with established 4T1-luc lung metastases were sacrificed at 1, 24, and 48 h, and major organs were dissected and imaged ex vivo with IVIS. As shown in FIG. 5A,B, fluorescence signals were observed exclusively in lungs with essentially no DiR signal seen in any other organs during the time course of 48 h. Concurring with the IVIS data, quantitative HPLC analysis of Rhod-b labeled NPs revealed predominant accumulation of NPs in lungs with negligible amount in blood and other tissues (FIG. 5C). It has been documented that the nanoparticles become exposed to lung environment after they are delivered in aerosols to bronchioles and alveoli, and then their physicochemical properties, e.g., size and surface charge, most likely determine their fate (Mangal (2017), supra). NP-cGAMP was formulated with a mean size of ~110 nm because it is generally accepted as an advantageous size, taking into account multiple factors such as payload and intratumoral diffusibility (Torchilin, et al. *Nat Rev Drug Discov* 4, 145-160, (2005); Zhang, et al. *J Control Release* 183C, 114-123, (2014)). Immunohistochemical studies of lung tissues post inhalation of NP-DiR clearly showed that the DiR signals were located primarily within CD11c$^+$ AMs or DCs; and co-staining with anti-luciferase to label the luciferase-expressing tumor cells further revealed that the NP-DiRs were distributed well in individual metastases and engulfed by intratumoral CD11c$^+$ AMs or DCs (FIG. 5D). These data demonstrate the ability of PS-NPs to penetrate tumor tissues and target intratumoral AMs and DCs.

FACS analysis was conducted to determine the uptake of NP-cGAMP by each subset of lung APCs. As shown in FIG. 5E, the lung APCs were classified into AMs (CD11c$^+$ F4/80$^+$), interstitial macrophages (IMs; CD11c$^-$ F4/80$^+$) and DCs (CD11c$^+$ F4/80$^-$). One hour post inhalation of NP-DiR, 41.7±7.0% of AMs, 13.2±3.6 of IMs, and 7.6±3.2 of DCs were DiR positive, which increased over the observation time up to 48 h (FIG. 5F). As noticed in previous HPLC data, the amount of Rhod-b-NPs in the lung draining lymph nodes (DLNs) increased over time (FIG. 5C), indicating a possibility that these nanoparticle-captured lung APCs might migrate to DLNs. This finding was further confirmed by FACS data, showing that the lung-derived DiR positive mAMs and mCD103$^+$ or mCD11 DCs did exist in DLNs (FIG. 5G). Together, these data demonstrate that the inhaled PS-coated NP effectively targets pulmonary APCs in lung metastases, supporting its use for delivery of cGAMP to activate intratumoral APCs.

Example 6. Inhalation of NP-cGAMP Promotes
APC Sensing of Tumor Antigen, Antigen-Specific
T Cell Priming, and Induces the Abscopal Effect of
Radiotherapy Against B16-OVA Lung Metastases Radiation is known for its potential to kill cancer cells to release tumor antigens, which may trigger systemic immune response against cancer metastases at distant sites, the so called 'abscopal effect.' However, the abscopal effect is rarely seen in clinic. See, e.g., Reits, et al. *J Exp Med* 203, 1259-1271, (2006); Dovedi, et al. *Cancer Immunol Res* 4, 621-630, (2016); Demaria, et al. *Trends Cancer* 2, 286-294, (2016); Wu, et al. *Front Immunol* 8, 613, (2017); Dewan, et al. *Clin Cancer Res* 15, 5379-5388, (2009); Sharabi, et al. *Cancer Immunol Res* 3, 345-355, (2015); Mason, K. A. *Clin Cancer Res* 11, 361-369, (2005).

In this study, experiments were conducted to investigate whether inhalation of NP-cGAMP could enhance the effect of radiotherapy, and further the abscopal effect against cancer metastases. A B16-OVA melanoma lung metastasis model was established in immunocompetent mice by injecting B16-OVA cells intravenously. Five days later, after visualizing multifocal lung metastases throughout both lungs in the randomly selected mice, the mice were treated with radiotherapy alone, inhalation of NP-cGAMP, or both. Fractionated radiotherapy (8 Gy×3 daily fractions) was delivered to the right lung while avoiding the important mediastinum. For the combination treatment, NP-cGAMP was inhaled 24 h after each of 3 radiotherapy fractions. cGAMP concentration in lungs after inhalation was determined based on previous HPLC measurements of the inhaled Rhod-b-NP. It was estimated that 0.1 μg cGAMP was deposited to an animal's lungs after each inhalation, which was less than one-hundredth of the dose of free cGAMP used for intratumoral injection in several studies. Deng, et al. *Immunity* 41, 843-852, (2014); Baird, et al. *Cancer Res* 76, 50-61, (2016).

On day 18, the mice were sacrificed and treatment efficacy was analyzed by counting the number of metastases on the surface of lungs under a dissecting microscope (FIG. 6A,B). For the mice treated with radiotherapy alone, smaller lesions were observed in the irradiated right lung despite no significant change in the total number of lesions, while metastases in the non-irradiated left lung were not affected, as compared to the control treatment. Inhalation of NP-cGAMP alone led to a decrease in the number of metastatic foci in both lungs (p<0.05). Inhalation of NP-cGAMP plus radiotherapy achieved the highest therapeutic efficacy with significant inhibition of metastases in both the radiotherapy and non-radiotherapy treated lungs, even complete regression of lung metastases in some mice (p<0.001; FIG. 6A,B). These data demonstrate that inhalation of NP-cGAMP in combination with radiotherapy induces strong antitumor immunity that leads to regression of lung metastases in both the irradiated and non-irradiated lungs.

To study the mechanism underlying the enhanced immunity, the ability of inhaled NP-cGAMP to improve cross-presentation of the tumor antigen in vivo was assessed. A subset of the mice from the above treatment groups were sacrificed 24 h after the last inhalation (48 h after the last radiotherapy). Both tumor-bearing lungs and DLNs were dissected. CD103$^+$ DCs have been implicated as the most competent APCs for cross-presenting TAAs to prime T cells in mice. Engblom, et al. Nat Rev Cancer 16, 447-462, (2016); Spranger, et al. Cancer Cell 31, 711-723 e714, (2017). Therefore, FACS gating strategies were employed to differentiate CD103$^+$ DCs (CD103$^+$ CD11b$^-$ CD11 from CD11b$^+$ DCs (CD11b$^+$ CD103$^-$ CD11c$^+$), and the expression of the OVA peptide SIINFEKL-MHC-I complex on CD103$^+$ DCs was further analyzed. As opposed to radiotherapy alone that led to an increase only in the irradiated lung, inhalation of NP-cGAMP significantly upregulated antigen presentation on CD103$^+$ DCs in both lungs (FIG. 6C). The radiotherapy plus inhalation induced even higher antigen presentation on CD103$^+$ DCs in both lungs (FIG. 6C). CD103$^+$ DCs with high antigen presentation were also detected in DLNs (FIG. 6D), implicating migration of these APCs from tumor sites to DLNs where they cross-present TAA to prime T cells.

Consistent with previous in vitro observations, inhalation of NP-cGAMP alone or in combination with radiotherapy activated APCs in both lungs by significantly promoting their expression of co-stimulatory molecule, CD86 and MHC-II (FIG. 7). These results are in good agreement with recently published work showing that tumor-infiltrating APCs develop an immunosuppressive phenotype characterized by lower expression of co-stimulatory molecules, decreased antigen presenting activity or even direct inhibition of CD8$^+$ T cell immunity. Engbloom (2016) supra;

Spranger (2017) supra; Chiba, et al. *Nat Immunol* 13, 832-842, (2012); Tran Janco, et al. *J Immunol* 194, 2985-2991, (2015); Norian, et al. *Cancer Res* 69, 3086-3094, (2009).

Subsequent experiments investigated whether the inhaled NP-cGAMP with/without radiotherapy drove expansion of tumor antigen-specific T cells. As shown in FIG. 6E-G, significantly increased numbers of CD4$^+$ and CD8$^+$ T cells were observed in both lungs of the mice after treatment with radiotherapy, NP-cGAMP inhalation or both. However, further FACS analysis after SIINFEKL-MHC tetramer staining showed that the combination treatment led to a ~10 fold and >5 fold increase in the number of tumor antigen-specific CD8$^+$ T cells in both lungs compared to the control and radiotherapy alone, respectively (FIG. 6H,I). Moreover, inhalation alone or in combination with radiotherapy significantly activated these tumor-specific CD8$^+$ T cells, evidenced by observing higher intracellular IFN$\gamma$ in the tetramer-positive T cells (FIG. 6J). Examinations of the DLNs from the combination treatment also revealed significant expansion of tumor-specific CD8$^+$ T cells (FIG. 8A,B). Further study interrogated if the combination treatment triggered systemic tumor-specific immunity. The tumor-specific T cells in the spleen were examined and it was found that there was indeed a significant increase in tetramer-positive CD8$^+$ T cells in spleen (p<0.001; FIG. 8A,C). An in vivo VITAL assay was conducted by injecting the CFSE fluorescence labeled OVA-splenocytes into the mice previously treated in different groups. Compared with the relatively constant level of the non-OVA labeled splenocytes, significantly more killing (>60%) of the OVA-splenocytes was observed in blood of the mice treated with radiotherapy plus inhalation (p<0.001; FIG. 8D,E), confirming induction of systemic tumor-specific immunity.

To determine whether NP-cGAMP induced anticancer immune response is innate APC-dependent and what subset of effector T cells is required to execute the response, depletion studies were conducted in the mice receiving radiotherapy plus inhalation of NP-cGAMP. To deplete pulmonary APCs, the same nanoconstruct of the PS-coated NP was used to encapsulate an anti-APC drug, clodronate (NP-Clod) and delivered NP-Clod via inhalation 6 h before each of the NP-cGAMP inhalations for 3 doses. To deplete CD4 or CD8$^+$ T cells, anti-mouse CD4 or CD8 antibodies were injected i.p. 1 day before radiotherapy and repeated 7 days later. It was found that the depletion of lung APCs or CD8$^+$ T cells (FIG. 6B), but not CD4$^+$ T cells, significantly abrogated the antitumor function of the combination treatment, suggesting that both APCs and CD8$^+$ T cells are required for the induced antitumor immunity. Collectively, these data demonstrate that inhalation of NP-cGAMP promotes innate APC immune sensing through the STING pathway and consequent antigen-specific CD8$^+$ T cell priming, and synergizes with radiotherapy to elicit strong anticancer immunity that results in complete control of both the irradiated and non-irradiated B16-OVA lung metastases.

Example 7. Inhalation of NP-cGAMP Promotes Pro-Inflammatory Response and Improves the Ratio of Effector to Regulatory T Cells in Both the Irradiated and Non-Irradiated Lung Metastases It has been well recognized that the tumor microenvironment is extremely immunosuppressive, which may largely counteract the antitumor immunity even if TAA-specific immunity can be activated by radiotherapy. Ngwa, et al. *Nat Rev Cancer* 18, 313-322, (2018). Experiments were conducted with the hypothesis that the inhaled NP-cGAMPs, which are accessible to individual metastases in both lungs, would overcome the immunosuppressive tumor environment in both the radiotherapy and non-radiotherapy treated tumors. To prove this hypothesis, it was investigated if inhalation of NP-cGAMP enhanced in vivo production of type I IFNs and other proinflammatory cytokines. A subset of the mice from the above treatment groups were sacrificed 24 h after the last inhalation, and B16-OVA metastases-bearing lung tissues were dissected and subject to cytokine analysis. ELISA results showed that inhalation of NP-cGAMP led to significantly elevated levels of IFN-10 as well as TNF$\alpha$, IFN$\gamma$, IL-6, IL-12p40 in both lungs (FIG. 9A). By contrast, radiotherapy alone caused no significant change in the above cytokines in the non-irradiated left lung despite a moderate increase in the irradiated lung. Of interest, CXCL10, the ligand of CXCR3, was found to significantly increase in both lungs after radiotherapy alone, inhalation of NP-cGAMP or both (FIG. 9A). Along with CXCL10, overexpression of another CXCR3 ligand, CXCL9 was also observed previously in vitro in the NP-cGAMP treated APCs (FIG. 2B). Because CXCL9 and 10 are known for their roles on recruiting CXCR3$^+$ lymphocytes (Spranger (2017) supra), increased levels of these ligands may contribute significantly to the marked increase in tumor-infiltrating T cells in both lungs, as observed previously.

There is increasing evidence that the level of antitumor immunity is controlled by the balance of tumor-specific effector T cells and Tregs. Brody (2010) supra; Perret, et al. *Cancer Res* 73, 6597-6608, (2013). As shown in FIGS. 4 and 5, radiation alone was able to promote a moderate but significant increase in the number of tumor-infiltrating CD4$^+$ and CD8$^+$ T cells in both lungs and DLNs. However, radiotherapy also led to increased number of tumor-infiltrating FoxP3$^+$ CD4$^+$ Tregs, and consequently a significantly decreased ratio of CD8$^+$ T/Tregs in the irradiated tumors (p<0.05; FIG. 9B,C). Similar observations have been reported by others. Baird, et al. *Cancer Res* 76, 50-61, (2016); Kachikwu, et al. *Int J Radiat Oncol Biol Phys* 81, 1128-1135, (2011). However, this negative effect was abrogated by the inhaled NP-cGAMP, as evidenced by significantly increased ratios of CD8$^+$ T/Treg in both lungs (FIG. 9B,C). These findings are in agreement with studies reporting activation of the STING pathway or type I IFNs to directly inhibit co-stimulation-dependent Treg activation and proliferation. Dovedi, et al. *Cancer Immunol Res* 4, 621-630, (2016); Srivastava, et al. *J Exp Med* 211, 961-974, (2014). Thus, unlike the direct intratumoral injection, the inhalation strategy described herein provides for delivery of NP-cGAMP to the lesions in both irradiated and non-irradiated lungs to stimulate proinflammatory cytokines and suppress Tregs. The data further reiterate the importance of overcoming the immunosuppressive tumor environment not only in the irradiated tumor but also non-irradiated tumors in order to elicit the abscopal effect of radiotherapy.

Example 8. Efficacy of NP-cGAMP Inhalation Combined with Radiotherapy is Confirmed in the 4T1 Breast Cancer Lung Metastases To determine whether potent antitumor immunity derived from radiotherapy plus inhalation of NP-cGAMP was confined to B16-OVA lung metastases, the study was extended to 4T1 breast cancer cells that were stably transfected with firefly luciferase to facilitate imaging of cancer metastases. To mimic clinical development of breast cancer lung metastases, 4T1-luc cells were implanted orthotopically into the mammary fat pad. When the tumor reached ~500 mm³ on day 14, the primary tumor was surgically removed. On day 18, after lung signals were detected by bioluminescence imaging (BLI; FIG. 10A), indicating establishment of lung metastases, the mice were randomly grouped and treated with radiotherapy alone (right lung), inhalation of NP-cGAMP, or both, with the same dose and schedule as in the previous B16-OVA studies. Both BLI and MRI were applied to monitor the growth of lung metastases up to 3 wks post treatment.

Compared to the control group, the mice treated with radiotherapy or the inhaled NP-cGAMP alone exhibited significantly lower BLI signals on day 32 and 39, indicating delayed tumor growth (FIG. 10A,B). However, the combination of radiotherapy and inhalation of NP-cGAMP led to complete regression of lung metastases in both lungs. MRI quantitatively evaluated tumor volume change by measuring individual lung metastases in both lungs and summing to obtain the total tumor volume for each animal. Consistent with the BLI data, the total tumor volume was significantly smaller in the combination group than radiotherapy or inhalation alone (FIG. 10C,D). The imaging data were validated by ex vivo examination of lung metastases of individual lungs from each treatment group (FIG. 10E). For the long term survival study, as presented in the Kaplan-Meier survival curves, the mice treated with inhalation of NP-cGAMP plus radiotherapy survived significantly longer (p<0.001; FIG. 10F), 50% of them (n=4) were completely cured, showing no sign of disease for at least 150 days (FIG. 10F). Similar to the B16-OVA study, it was found that the survival benefit from the combination treatment was abrogated after depletion of pulmonary APCs with NP-Clod (FIG. 10F), supporting the indispensable role of APCs in the observed antitumor immunity.

Mechanistic studies were also conducted by sacrificing a subset of the 4T1-luc mice from each treatment group at 24 h post the last inhalation of NP-cGAMP. Consistent with previous observations in the B16-OVA lung metastases, FACS analysis revealed that inhalation of NP-cGAMP activated APCs in both of the 4T1-luc metastases-bearing lungs, as evidenced by significantly increased expression of CD86 and MHC-II on CD103⁺ DCs, CD11b⁺ DCs and AMs (FIG. 11). Inhalation of NP-cGAMP also led to drastic increase in IFN-1β and other proinflammatory cytokines in both lungs (FIG. 12). Moreover, inhalation of NP-cGAMP with/without radiotherapy increased the number of tumor-infiltrating CD4⁺ and CD8⁺ T cells (FIG. 13) as well as activated CD8⁺ T cells that were positively stained for intracellular IFNγ in both lungs (FIG. 14A,B). As in the B16-OVA study, radiotherapy alone induced a significant increase in the tumor-infiltrating FoxP3⁺ CD4⁺ Tregs and a decrease in the ratio of CD8⁺ T/Tregs in the irradiated right lung (FIG. 14C,D). However, inhalation of NP-cGAMP offset the negative impact of radiotherapy, resulting in a significant increase in the CD8⁺ T/Tregs ratio (p<0.01; FIG. 14C,D). Immunohistochemical staining of CD8⁺ T cells and FoxP3⁺ Tregs in metastases-bearing lung tissues coincided with the FACS data (FIG. 14E,F). Together with previous studies in the B16-OVA model, inhalation of NP-cGAMP in combination with radiotherapy effectively control lung metastases both locally and by inducing the abscopal effect in non-irradiated lung metastases.

Example 9. Inhalation of NP-cGAMP is Safe

Liposomes and other lipid-based particles are biocompatible and safe, and most clinically approved nanoparticle drugs are formulated in this manner. Inhalation of NP-cGAMP was well-tolerated by the unanaesthetized mice. To investigate whether inhalation of NP-cGAMP potentially induces systemic immune toxicity, systematic studies were conducted by measuring cytokine levels in blood and examining major organs histopathologically. For evaluation of possible acute effects, blood samples of healthy mice with/without inhalation of NP-cGAMP and the B16-OVA metastases-bearing mice in different treatment groups were obtained 24 h after 3 consecutive daily inhalations of NP-cGAMP.

As shown in FIG. 15, a slight increase in serum IFNγ, IL-6, IL-12p40 and IL-10, but not IFN-1β and TNFα, was observed in healthy mice. Similar cytokine profiles without drastic increase were detected in the lung metastases-bearing mice treated with inhalation with/without radiotherapy. There was no significant difference in the blood levels of liver enzymes, aspartate aminotransferase (AST) and alanine aminotransferase (ALT) at 24 h or 3 wks. H&E staining of liver, kidney and heart showed no visible morphological change in the mice treated with inhalation alone or with inhalation and radiotherapy. We further investigated whether the combination treatment caused any long term toxicity to lungs. The 4 mice that were cured with the combination treatment were sacrificed on day 150. Visual examinations of major organs including lungs, liver and kidney under a dissecting microscope revealed no obvious lesions; histological examinations also found no microscopic lesions in lungs, confirming no residual metastases. Moreover, the shape of alveolar sacs, alveolar wall thickness and microvasculature in the non-irradiated left lung all looked similar to the healthy counterpart. While a few small regions in the irradiated lung were seen to contain clustering macrophage-like cells and some slightly thickened alveolar walls, there was no obvious pathological change, e.g., fibrosis. The lack of local and systemic toxicity may be attributed to the low inhaled dose of NP-cGAMP and its APC-targeting property, which led to negligible amounts of cGAMP taken up by other types of lung cells or entering blood circulation, as shown by HPLC analysis (FIG. 5C). Besides the intratumoral APCs, uptake by APCs in normal lungs may also contribute to anti-cancer immunity by creating pro-inflammatory response in tumor margins as well as DLNs. Nevertheless, inhalation of NP-cGAMP in combination with radiotherapy is safe and effective against lung metastases.

Demonstrated herein is a new nanotechnological approach to enhance innate immune sensing of immunogenic radiation treatment and tumor-specific adaptive immunity, and importantly, remodel the tumor microenvironment by converting 'cold' into 'hot' tumors in both the irradiated and non-irradiated tumors. The nanoplatform developed in this study can be extended to deliver other types of immunostimulants such as CpG ODN or TLR7/TLR8 agonist R848, which are only effective when bound to their cytosolic TLRs. In terms of clinical disease relevance, in addition to lung metastases, this combination approach may also be applicable to primary lung cancer which has spread to local lymph nodes, different regions of lungs, or even the trachea or esophagus. With a similar strategy of using hypofractionated stereotactic body radiation therapy (SBRT) to treat a single lesion or a few lesions in lung, and combined with inhalation of NP-cGAMP to activate antitumor immunity in both the irradiated tumor and non-irradiated tumors, potent local and abscopal antitumor effects can be expected.

Example 10. Treatment of Non-Small Cell Lung
Cancer (NSCLC) in an Orthotopic Model by
NP-cGAMP Inhalation Combined with
Radiotherapy and Anti-PD-L1

An orthotopic NSCLC model of Lewis lung carcinoma
(LLC) was established in immunocompetent mice by intra-
tracheal instillation of LLC cells. Fourteen days later, mul-
tifocal primary lung carcinomas in both sides of lungs were
confirmed by MRI and H&E staining (FIG. 16).

After inhalation of the fluorescence dye DiR labeled
NP-DiR, the mice with established LLC-luc orthotopic lung
cancer were sacrificed at 24 and 48 h, respectively, and
major organs were dissected and imaged ex vivo with IVIS.
As shown in FIG. 17A,B, fluorescence signals were
observed exclusively in lungs with essentially no DiR signal
seen in any other organs during the time course of 48 h.
Concurring with the IVIS data, quantitative HPLC analysis
of Rhod-b labeled NPs revealed predominant accumulation
of the NPs in lungs with a negligible amount in blood and
other tissues (FIG. 17C). Immunohistochemical studies of
lung tissues post inhalation of NP-DiR clearly showed that
the DiR signals were located primarily within CD11c+ AMs
or DCs; and co-staining with anti-luciferase to label the
luciferase-expressing tumor cells further revealed that the
NP-DiRs were distributed well in individual lung tumor and
engulfed by intratumoral CD11c+ AMs or DCs (FIG. 17D).
These data demonstrate the ability of PS-NPs to penetrate
tumor tissues and target intratumoral AMs and DCs.

PD-L1, also known as CD274 and B7-H1, is a transmem-
brane protein commonly expressed on the surface of antigen
presenting cells and tumor cells. PD-L1 specifically binds to
its receptor, PD-1, which is expressed on the surface of
immune-related lymphocytes, mainly T cells. The binding of
PD-L1 to PD-1 is able to inhibit the proliferation, cytokine
generation and release, and cytotoxicity of T cells. PD-L1
can be induced exogenously by stimuli-molecules such as a
STING agonist or radiation in tumor microenvironment in
many cells including tumor cells and APCs. On Day 18,
mice with LLC lung cancer were treated with NP-cGAMP
inhalation with/without irradiation (IR). 24 h after the last
inhalation of NP-cGAMP, expression of PD-L1 in tumor
cells, AMs, and DCs were determined by FACS. As shown
in FIG. 18, PD-L1 positive population was significantly
induced by inhalation of NP-cGAMP and further increased
with combination of IR.

Studies were then conducted to investigate whether NP-
cGAMP inhalation improves the immunosuppressive tumor
microenvironment in orthotopic NSCLC. As shown in
FIGS. 19A, B, and C, inhalation of NP-cGAMP promoted a
significant increase in the number of tumor-infiltrating CD4$^+$
T and CD8$^+$ T cells in lung, reduced the number of FoxP3$^+$
CD4$^+$ Tregs, and consequently provided a significantly
increased ratio of CD8$^+$ T/Tregs. Upon combination with
PD-L1 antibody, more tumor-infiltrating effector T cells
leading to a higher ratio of CD8$^+$ T/Tregs were observed.
Inhalation of NP-cGAMP with anti-PD-L1 also induced an
increased number of activated CD8$^+$ T cells as determined
by FACS measurements of intracellular IFN-γ staining, as
shown in FIG. 19D. These findings are in agreement with the
findings in lung metastases of breast cancer and melanoma
models, as described above in Examples 6-8.

The ability of NP-cGAMP inhalation to enhance anti-PD-
L1 immunotherapy was therefore investigated. On day 14,
when tumors were confirmed by MRI and IVIS, mice were
randomly grouped and treated with IR alone (right lung),
NP-cGAMP inhalation, anti-PD-L1, NP-cGAMP inhalation plus anti-PD-L1, or NP-cGAMP inhalation plus anti-PD-L1
plus IR. The dose of NP-cGAMP and IR were consistent
with breast cancer and melanoma models as described
above. The PD-L1 dose was 100 μg per mice (3 times per
week, every other day). A long term survival study, as
summarized in Kaplan-Meier survival curves, showed that
the mice treated with inhalation of NP-cGAMP plus radio-
therapy and anti-PD-L1 survived significantly longer
(p<0.001; FIG. 20), and 80% of them (n=8) were completely
cured, showing no sign of disease for at least 90 days (FIG.
20).

V. EXEMPLARY EMBODIMENTS

Exemplary embodiments provided in accordance with the
presently disclosed subject matter include, but are not lim-
ited to, the claims and the following embodiments:

1. A composition comprising a lipid nanoparticle that
targets antigen presenting cells.

2. The composition of embodiment 1, wherein the lipid
nanoparticle comprises a lipid bilayer containing anionic
phosphatidylserine, and wherein the anionic phosphatidyl-
serine is present in both layers of the lipid bilayer.

3. The composition of embodiment 2, wherein the anionic
phosphatidylserine targets the antigen presenting cells.

4. The composition of embodiment 1, wherein the lipid
nanoparticle comprises a nucleic acid therapeutic agent.

5. A composition comprising a lipid nanoparticle com-
prising a nucleic acid therapeutic agent.

6. The composition of embodiment 5, wherein the lipid
nanoparticle comprises phosphatidylserine.

7. The composition of embodiment 6, wherein the phos-
phatidylserine targets the lipid nanoparticle to antigen pre-
senting cells upon administration to a subject.

8. The composition of any one of embodiments 1-7,
wherein the lipid nanoparticle is a calcium phosphate nan-
oparticle having a lipid coating comprising phosphatidyl-
serine, wherein the calcium phosphate nanoparticle com-
prises the nucleic acid therapeutic agent, and wherein the
nucleic acid therapeutic agent is a cyclic dinucleotide.

9. The composition of embodiment 8, wherein the ratio of
the lipid to cyclic dinucleotide ranges from about 10:1 to
about 1000:1 by weight.

10. The composition of embodiment 8 or embodiment 9,
wherein the ratio of the lipid to cyclic dinucleotide ranges
from about 20:1 to about 40:1 by weight.

11. The composition of any one of embodiments 8-10,
wherein the cyclic dinucleotide is 2'3' cyclic guanosine
monophosphate-adenosine monophosphate (2'3' cGAMP).

12. The composition of any one of embodiments 8-11,
wherein the amount of phosphatidylserine ranges from about
10 mol % to about 80 mol % based on the total amount of
lipids in the lipid coating.

13. The composition of any one of embodiments 8-12,
wherein the amount of phosphatidylserine ranges from about
45 mol % to about 55 mol % based on the total amount of
lipids in the lipid coating.

14. The composition of any one of embodiments 8-13,
wherein the phosphatidylserine comprises a stearoyl (18:0)
moiety, an oleoyl (18:1) moiety, an eicosatetraenoyl (20:4)
moiety, a docosahexaenoyl (22:06) moiety, or a combination
thereof.

15. The composition of any one of embodiments 8-14,
wherein the lipid coating further comprises a phosphatidyl-
choline, a sterol, or a combination thereof.

16. The composition of any one of embodiments 8-15, wherein the size of the lipid nanoparticle, inclusive of the lipid coating, ranges from about 50 nm to about 150 nm in diameter.

17. The composition of any one of embodiments 8-16, wherein the composition is formulated for administration to the lungs of a subject via inhalation.

18. The composition of embodiment 5, wherein the lipid nanoparticle comprises a component that targets the lipid nanoparticle to antigen presenting cells upon administration to a subject.

19. The composition of embodiment 18, wherein the component that targets the lipid nanoparticle to antigen presenting cells is phosphatidylserine.

20. The composition of any one of embodiments 1-7 and 18-19, wherein the lipid nanoparticle is a liposome comprising a lipid membrane and an aqueous core.

21. The composition of embodiment 20, wherein the liposome comprises a nucleic acid therapeutic in the aqueous core.

22. The composition of embodiment 20 or embodiment 21, wherein the diameter of the liposome is in the range of 50 nm and 200 nm.

23. The composition of any one of embodiments 4-22, wherein the nucleic acid therapeutic is a STING agonist.

24. The composition of embodiment 23, wherein the STING agonist is a cyclic dinucleotide.

25. The composition of any one of embodiments 4-7, wherein the nucleic acid therapeutic comprises a plasmid.

26. A method for treating cancer, the method comprising administering to a subject in need thereof a therapeutically effective amount of a composition as provided herein.

27. The method of embodiment 26, wherein the composition comprises a lipid nanoparticle that targets antigen presenting cells.

28. The method of embodiment 26, wherein:
   the lipid nanoparticle comprises a nucleic acid therapeutic agent,
   the lipid nanoparticle is a calcium phosphate nanoparticle having a lipid coating,
   the calcium phosphate nanoparticle comprises the nucleic acid therapeutic agent, and
   the nucleic acid therapeutic agent is a cyclic dinucleotide.

29. The method of embodiment 28, wherein the composition is administered to the subject via inhalation.

30. The method of any one of embodiments 26-29, wherein the cancer is a lung cancer, a head and neck cancer, or an esophageal cancer.

31. The method of any one of embodiments 26-30, wherein the cancer comprises one or more metastatic tumors.

32. The method of any one of embodiments 26-31, further comprising administering radiotherapy to the subject.

33. The method of any one of embodiments 26-32, further comprising administering an immune checkpoint inhibitor to the subject.

34. The method of embodiment 33, wherein the immune checkpoint inhibitor is a PD-L1 antibody.

35. The method of any one of embodiments 28-34, wherein the cyclic dinucleotide is 2'3' cyclic guanosine monophosphate-adenosine monophosphate (cGAMP).

36. The method of any one of embodiments 28-35, wherein the ratio of the lipids to the cyclic dinucleotide ranges from about 10:1 to about 1000:1 by weight.

37. The method of any one of embodiments 28-36, wherein the lipid coating comprises phosphatidylserine.

38. The method of any one of embodiments 28-37, wherein the lipid coating comprises a phosphatidylcholine, a sterol, or a combination thereof.

39. The method of any one of embodiments 26-38, wherein the size of the lipid nanoparticle ranges, inclusive of the lipid coating, from about 50 nm to about 150 nm in diameter.

40. The method of any one of embodiments 26-39, wherein the composition is aerosolized during administration.

Although the foregoing has been described in some detail by way of illustration and example for purposes of clarity and understanding, one of skill in the art will appreciate that certain changes and modifications can be practiced within the scope of the appended claims. In addition, each reference provided herein is incorporated by reference in its entirety to the same extent as if each reference was individually incorporated by reference.

What is claimed is:

1. A composition comprising a calcium phosphate nanoparticle having a lipid coating, wherein the lipid coating comprises a bilayer containing anionic phosphatidylserine, a phosphatidylcholine, and a sterol, wherein the anionic phosphatidylserine is present in both layers of the bilayer, wherein the calcium phosphate nanoparticle targets antigen presenting cells, and wherein the composition can be used as an inhalable nanoparticle immunotherapy that can be aerosolized during use, wherein the calcium phosphate nanoparticle comprises a nucleic acid therapeutic agent, and wherein the nucleic acid therapeutic agent is 2'3' cyclic guanosine monophosphate-adenosine monophosphate (2'3' cGAMP).

2. The composition of claim 1, wherein the composition has a ratio of the total lipids to 2'3' cGAMP that ranges from about 10:1 to about 1000:1 by weight.

3. The composition of claim 1, wherein the composition has a ratio of the total lipids to 2'3' cGAMP that ranges from about 20:1 to about 40:1 by weight.

4. The composition of claim 1, wherein the phosphatidylserine is present in an amount that ranges from about 10 mol % to about 80 mol % based on a total amount of lipids in the lipid coating.

5. The composition of claim 1, wherein the phosphatidylserine comprises a stearoyl (18:0) moiety, an oleoyl (18:1) moiety, an eicosatetraenoyl (20:4) moiety, a docosahexaenoyl (22:06) moiety, or a combination thereof.

6. The composition of claim 1, wherein the calcium phosphate nanoparticle, inclusive of the lipid coating, has a size range from about 50 nm to about 200 nm in diameter.

7. The composition of claim 1, wherein the composition is formulated for administration to the lungs of a subject.

8. A method for treating cancer, the method comprising:
   administering to a subject in need thereof a therapeutically effective amount of a composition of claim 1 wherein administering comprises inhalation of the composition;
   co-administering to the subject in need thereof one or more immune checkpoint inhibitors; and
   administering radiotherapy to the subject following administration of the therapeutically effective amount of the composition and the immune checkpoint inhibitor.

9. The method of claim 8, wherein the cancer is a lung cancer, a head and neck cancer, or an esophageal cancer.

10. The method of claim 8, wherein the cancer comprises one or more metastatic tumors.

11. The method of claim 8, wherein the composition has a ratio of the total lipids to the 2'3' cGAMP that ranges from about 10:1 to about 1000:1 by weight.

12. The method of claim 8, wherein the calcium phosphate nanoparticle, inclusive of the lipid coating, has a size range from about 50 nm to about 150 nm in diameter.

13. The method of claim 8, wherein the composition is aerosolized during administration.

14. A liquid composition comprising a calcium phosphate nanoparticle having a lipid coating, wherein the lipid coating comprises a bilayer containing anionic phosphatidylserine, phosphatidylcholine, and a sterol, wherein the anionic phosphatidylserine is present in both layers of the bilayer, wherein the calcium phosphate nanoparticle targets antigen presenting cells, wherein the liquid composition can be aerosolized prior to administration, wherein the calcium phosphate nanoparticle comprises a nucleic acid therapeutic agent, and wherein the nucleic acid therapeutic agent is 2'3' cyclic guanosine monophosphate-adenosine monophosphate (2'3' cGAMP).

15. The composition of claim 1, wherein the anionic phosphatidylserine, the phosphatidylcholine, and the sterol are present in a molar ratio of 5:4:1.

\* \* \* \* \*